(12) United States Patent
Suda et al.

(10) Patent No.: US 9,963,692 B2
(45) Date of Patent: May 8, 2018

(54) THERMOSTABLE CELLOBIOHYDROLASE

(71) Applicants: HONDA MOTOR CO., LTD, Minato-ku, Tokyo (JP); Kazusa DNA Research Institute, Kisarazu-shi, Chiba (JP)

(72) Inventors: Migiwa Suda, Kisarazu (JP); Jiro Ohkuma, Wako (JP); Asuka Yamaguchi, Tokyo (JP); Yoshitsugu Hirose, Wako (JP); Yasuhiro Kondo, Kawagoe (JP); Tomohiko Kato, Kisarazu (JP); Daisuke Shibata, Kisarazu (JP)

(73) Assignees: Honda Motor Co., Ltd., Tokyo (JP); Kazusa DNA Research Institute, Chiba (JP)

( * ) Notice: Subject to any disclaimer, the term of this patent is extended or adjusted under 35 U.S.C. 154(b) by 0 days. days.

(21) Appl. No.: 14/759,740

(22) PCT Filed: Mar. 27, 2014

(86) PCT No.: PCT/JP2014/058798
§ 371 (c)(1),
(2) Date: Jul. 8, 2015

(87) PCT Pub. No.: WO2014/157492
PCT Pub. Date: Oct. 2, 2014

(65) Prior Publication Data
US 2016/0053246 A1 Feb. 25, 2016

(30) Foreign Application Priority Data
Mar. 27, 2013 (WO) ............... PCT/JP2013/059028

(51) Int. Cl.
*C12N 9/42* (2006.01)
*C12P 19/02* (2006.01)
*C12P 19/14* (2006.01)

(52) U.S. Cl.
CPC ............ *C12N 9/2437* (2013.01); *C12P 19/02* (2013.01); *C12P 19/14* (2013.01); *C12Y 302/01091* (2013.01)

(58) Field of Classification Search
CPC .................................................. C12N 9/2437
See application file for complete search history.

(56) References Cited

U.S. PATENT DOCUMENTS

2010/0255542 A1* 10/2010 Arnold .................. C12P 19/14
435/72

FOREIGN PATENT DOCUMENTS

| JP | 2005-237233 A | 9/2005 |
|---|---|---|
| JP | 2006-515506 A | 6/2006 |
| JP | 2007-053994 A | 3/2007 |
| JP | 2008-526236 A | 7/2008 |
| JP | 2008-193953 A | 8/2008 |
| JP | 2010-516296 A | 5/2010 |
| JP | 2012-039967 A | 3/2012 |
| WO | 2004/016760 A2 | 2/2004 |
| WO | 2006/074435 A2 | 7/2006 |
| WO | 2008/095033 A2 | 7/2008 |
| WO | 2008/095033 A2 | 8/2008 |
| WO | 2013016207 A2 | 1/2013 |

OTHER PUBLICATIONS

Ganju et al., "Purification and characterization of two cellobiohydrolases from *Chaetomium thermophile* var. *coprophile*", Biochim. Biophys. Acta, 1989, vol. 993, p. 266-274.
Hong et al., "Cloning of a gene encoding thermostable cellobiohydrolases from Thermoascus aurantiacus and its expression in yeast", Appl Microbiol Biotechnol., 2003, vol. 63, p. 42-50.
Zverlov et al., "A newly described cellulosomal cellobiohydrolase, CelO, from Clostridium thermocellum: investigation of the exo-mode of hydrolysis, and binding capacity to crystalline cellulose", Microbiology, 2002, vol. 148, p. 247-255.
Zverlov et al. "Thermotoga neapolitana bglB gene, upstream of lamA, encodes a highly thermostable beta-glucosidase that is a laminaribiase", Microbiology, 1997, vol. 143, p. 3537-3542.
Kataeva et al., "Cloning and Sequence Analysis of a New Cellulase Gene Encoding CelK, a Major Cellulosome Component of Clostridium thermocellum: Evidence for Gene Duplication and Recombination", Journal of Bacteriology, 1999, vol. 181, p. 5288-5295.
Zhang et al., "Characterization of a Thermomonospora fusca Exocellulase" Biochemistry, 1995, vol. 34, p. 3386-3395.
Irwin et al., "Cloning, expression and characterization of a Family 48 exocellulase, Cel48A, from Thermobifida fusca", Eur J Biochem., 2000, vol. 267, p. 4988-4997.
Ruttersmith et al., "Thermostable cellobiohydrolase from the thermophilic *Eubacterium thermotoga* sp. strain FjSS3-B.1", Biochemical Journal, 1991, vol. 277, p. 887-890.
Herai, et al., "Hyper-inducible expression system for streptomycetes", Proc. Natl. Acad. Sci. USA, 2004, vol. 101, p. 14031-14035.
Ogino et al., "Over-expression system for secretory phospholipase D by Streptomyces lividans", Appl. Microbiol. Biotechnol., 2004, vol. 64, p. 823-828.
Tamura et al., "Development of a Host-Vector System in *Rhodococcus* Species", J. Environmental Biotechnol., 2007, vol. 7, p. 3-10.
Bolam et al., "Pseudomonas cellulose-binding domains mediate their effects by increasing enzyme substrate proximity", Biochem. J., 1998, vol. 331, p. 775-781.

(Continued)

Primary Examiner — Sheridan Swope
(74) Attorney, Agent, or Firm — Carrier Blackman & Associates, P.C.; Joseph P. Carrier; Fulchand P. Shende

(57) ABSTRACT

The thermostable cellobiohydrolase of the present invention is a polypeptide which has cellobiohydrolase activity at least under conditions of a temperature of 75° C. and a pH of 5.5, and which includes a polypeptide including an amino acid sequence represented by SEQ ID NO: 1, 3, 5, or 7, a polypeptide including an amino acid sequence in which one or several amino acids are deleted, substituted, or added in an amino acid sequence represented by SEQ ID NO: 1, 3, 5, or 7, or a polypeptide including an amino acid sequence having 80% or greater but less than 100% sequence identity with an amino acid sequence represented by SEQ ID NO: 1, 3, 5, or 7.

3 Claims, 28 Drawing Sheets

(56) References Cited

OTHER PUBLICATIONS

Din et al., "C1-CX revisited: Intramolecular synergism in a cellulase", Proc. Natl. Acad. Sci. USA, 1994, vol. 91, p. 11383-11387.
Riedel et al., "The modular cellulase CelZ of the thermophilic bacterium Clostridium stercorarium contains a thermostabilizing domain", FEMS Microbiology Letters, 1998, vol. 164, p. 261-267.
Mahadevan et al., "Site-directed mutagenesis and CBM engineering of Cel5A (Thermotoga maritima)" FEMS Microbiol Lett., 2008, vol. 287, p. 205-211.
Wang et al., "Production of biologically active GM-CSF in sugarcane: a secure biofactory", Transgenic Research, 2005, vol. 14, p. 167-178.
Quinlan et al., "Pyrobayes: an improved base caller for SNP discovery in pyrosequences", Nature Methods, 2008, vol. 5, p. 179-181.
Kanehisa, M., "Toward Pathway Engineering: A New Database of Genetic and Molecular Pathways", Science & Technology Japan, 1996, No. 59, p. 34-38, http://www.genome.jp/kegg/, (searched in May 11, 2011).
Handelsman et al., "Molecular biological access to the chemistry of unknown soil microbes: a new frontier for natural products", Chem Biol., 1998, vol. 5, p. R245-R249.
Hoff et al., "Orphelia: predicting genes in metagenomic sequencing reads", Nucleic Acids Research, 2009, 37 (Web Server issue: W101-W105).
Noguchi et al., "MetaGeneAnnotator: Detecting Species-Specific Patterns of Ribosomal Binding Site for Precise Gene Prediction in Anonymous Prokaryotic and Phage Genomes", DNA Research, 2008, 15(6).
Finn et al., "The Pfam protein families database", Nucleic Acids Research Database, 2010, vol. 38, p. D211-222.
Durbin et al., "The theory behind profile HMMs. Biological sequence analysis: probabilistic models of proteins and nucleic acids", 1998, Cambridge University Press.; hmmpfam (Ver.2.3.2).
Daniell et al., "Chloroplast genetic engineering to improve agronomic traits", Methods in Molecular Biology, 2005, vol. 286, p. 111-138.
Verma and Daniell, "Chloroplast Vector Systems for Biotechnology Applications", Plant Physiol., 2007, vol. 145, p. 1129-1143.
Svab et al., "Stable transformation of plastids in higher plants", Proc. Natl. Acad. Sci. U.S.A., 1990, vol. 87, p. 8526-8530.
Geng et al., "Expression and characterization of a novel metagenome-derived cellulase Exo2b and its application to improve cellulose activity in Trichoderma reesei", Applied Microbiology and Biotechnology, 2012, vol. 96, pp. 951-962.
Wang et al., "Characterization of a novel thermostable beta-glucosidase from a metagenomic library of termite gut", Enzyme and Microbial Technology, 2012, vol. 51, pp. 319-324.
Wang et al., "Cloning and characterization of a thermostable and pH-stable cellobiohydrolase from Neocallimastix patriciarum J11", Protein Expression and Purification, Jun. 13, 2013, vol. 90, pp. 153-159.
International Search Report of International PCT/JP2014/058798 dated Apr. 22, 2014.
International Search Report of International PCT/JP2013/059028 dated May 7, 2013.
Search Report dated Nov. 3, 2016 for corresponding European Application No. 14772592.3.
Wu et al., "Engineered Thermostable Fungal Cel6A and Cel7A Cellobiohydrolases Hydrolyze Cellulose Efficiently at Elevated Temperatures," Biotechnology and Bioengineering, Jul. 2013, pp. 1874-1883, vol. 110, No. 7.
Database Uniprot [Online], "RecName: Full=Glucanase {ECO:0000256 RuleBase: RU361186}; EC=3.2.1.-{ECO:0000256 RuleBase: RU361186}," Jan. 15, 2008.

* cited by examiner

THERMOSTABLE CELLOBIOHYDROLASE

TECHNICAL FIELD

The present invention relates to the thermostability of cellobiohydrolase enzymes. Cellobiohydrolase is one of the glycoside hydrolases associated with the process of hydrolyzing lignocelluloses such as cellulose and hemicellulose to produce monosaccharides. In more detail, the present invention relates to novel thermostable cellobiohydrolases, polynucleotides that encode the thermostable cellobiohydrolases, expression vectors for expressing the thermostable cellobiohydrolases, transformants incorporated with the expression vectors, and methods for producing cellulose degradation products using the thermostable cellobiohydrolases.

Priority is claimed on International Patent Application No. PCT/JP2013/059028, filed Mar. 27, 2013, the content of which is incorporated herein by reference.

BACKGROUND ART

Recently, the development of alternative energy to oil is a very important issue, because of the concern related to transportation energy supply, such as large increases in oil prices and the petroleum depletion prediction in the near future (peak oil), as well as environmental problems such as global warming and aerial pollution. Plant biomass, or lignocellulose, is the most plentiful renewable energy source on earth, which is expected to serve as an alternative source to oil. The main components in the dry weight of biomass are polysaccharides such as celluloses and hemicelluloses, and lignin. For example, polysaccharides are used as a biofuel or a raw material of chemical products, after being hydrolyzed into monosaccharides such as glucose or xylose by glycoside hydrolases which are collectively referred to as cellulase enzymes.

Lignocellulose is recalcitrant due to its highly complicated structures, and is hard to degrade with a single cellulolytic enzyme. Lignocellulose degradation to sugar requires at least three types of enzymes: endoglucanases (cellulase or endo-1,4-β-D-glucanase, EC 3.2.1.4) which randomly cut internal sites on cellulose chain, cellobiohydrolases (1,4-β-cellobiosidase or cellobiohydrolase, EC 3.2.1.91) which act as an exo-cellulase on the reducing or non-reducing ends of cellulose chain and release cellobiose as major products, and β-glucosidases (EC 3.2.1.21) which hydrolyze cellobiose to glucose. Besides, it is thought to be necessary to have an appropriate blending of a plurality of enzymes including xylanase (endo-1,4-β-xylanase, EC 3.2.1.8) which is a hemicellulase and other plant cell wall degrading enzymes.

In the lignocellulose to ethanol conversion process, high-solid loading up to 30-60% in initial substrate concentration has been attempted for the purpose of higher energy efficiency and less water usage. The enzymatic reaction in the high-solid loading processes is, however, hardly progressed because of high viscosity of slurries. It is clear that thermostable enzymes have an advantage to allow the use of increased substrate concentrations, because the substrate viscosity decreases as the temperature increases. Moreover, high temperatures generally accelerate catalytic reaction according to the van't Hoff Arrhenius law, and promote better enzyme penetration and cell-wall disorganization of the raw materials. Thus, if lignocellulose hydrolysis is processed at higher temperatures than the conventional temperature by using thermostable enzymes, more efficient biomass to sugar conversion will be achieved, resulting in largely cutting down of the enzyme amount and the time for hydrolysis so as to largely reduce the cost of the enzymes.

The temperature limit of living for thermophilic filamentous fungi, which are eukaryotic, is lower at about 55° C., than those of thermophilic bacteria and hyperthermophilic archaea, which are prokaryotic. For this reason, the thermostability of glycoside hydrolases expressed or secreted from thermophilic filamentous fungi is generally not so high. The filamentous fungus-derived CBH (cellobiohydrolases) so far reported to have the highest thermostability are cellobiohydrolases CBHI and CBHII from a thermophilic filamentous fungus *Chaetomium thermophihum*, respectively showing the optimum temperatures of 75° C. and 70° C. (for example, see Non-patent document 1), and cellobiohydrolase CBHI from *Thermoascus aurantiacus* showing the optimum temperature of 65° C. (for example, see Non-patent document 2). There is also a method to enhance the thermostability by substituting one or a plurality of amino acids in cellobiohydrolase (for example, see Patent Documents 1 or 2). However, the thermostability of mutated cellobiohydrolase obtained in such a manner is not yet sufficient.

On the other hand, thermophiles which proliferate in extreme environments such as hot springs, hydrothermal vents, oil fields, or metalliferous mines, at 55° C. or higher, or hyperthermophiles which proliferate at 80° C. or higher, have been isolated and cultured. The thermostable glycoside hydrolases derived from these thermophilic bacteria and hyperthermophilic archaea are mostly enzymes having endoglucanase activity, xylanase activity, xylosidase activity, or glucosidase activity. Regarding cellobiohydrolases which play the most important role in the lignocellulose hydrolysis process, there have been only several cellobiohydrolases isolated from three kinds of thermophilic bacteria belonging to the genus *Clostridium*, the genus *Thermobifida*, and the genus *Thermotoga*. For example, a thermophilic anaerobic bacterium *Clostridium thermocellum*, presents an enzyme complex termed cellulosome which has high lignocellulose hydrolysis activity, to outside the bacterial body. The main enzyme of the cellulosome is cellobiohydrolase, and three types thereof, namely. CelO belonging to the GH5 family, and CbhA and CelK belonging to the GH19 family, have been isolated. All of them have the optimum temperatures ($T_{opt}$) of 60 to 65° C. (for example, see Non-patent documents 3 to 5). From a thermophilic actinobacterium *Thermobifida fusca*, there have been two different types of cellobiohydrolase genes isolated: E3 belonging to the GH6 family (for example, see Non-patent document 6), and Cel48A belonging to the GH48 family (for example, see Non-patent document 7). These cellobiohydrolases have relatively high thermostability. The temperature range at which they exhibit 50% activity of the maximum value is from 40 to 60° C. and a stable activity is held at 55° C. for at least 16 hours. However, these two types of cellobiohydrolases have insufficient activity at a temperature of 70° C. or higher. If an enzymatic hydrolysis process of cellulose is conducted using these two types of cellobiohydrolases, the upper limit temperature for the process would be 60 to 65° C. The cellobiohydrolase derived from a thermophilic bacterium belonging to the genus *Thermotoga* has the highest thermostability, and it has been reported to have the $T_{opt}$ of 105° C. and the activity half-life time ($T_{half}$) of 70 minutes at 108° C. (for example, see Non-patent document 8). However, the enzyme shows an endoglucanase-like substrate specificity, and exhibits the degradation activity only to amorphous structured cellulose and carboxymethyl cellulose (CMC). Furthermore, because of a weak hydrolysis activity to a filter paper, efficient hydrolysis of crystalline lignocellulose cannot be expected with this enzyme.

PRIOR ART DOCUMENTS

Patent Documents

Patent document 1: Published Japanese Translation No. 2006-515506 of PCT International Publication
Patent document 2: Japanese Unexamined Patent Application, First Publication No. 2012-39967
Patent document 3: Japanese Unexamined Patent Application, First Publication No. 2005-237233
Patent document 4: Japanese Unexamined Patent Application. First Publication No. 2007-53994
Patent document 5: Japanese Unexamined Patent Application, First Publication No. 2008-193953
[Non-patent Documents]
Non-patent document 1: Ganju et al., Biochim. Biophys. Acta, 1989, vol. 993, p.266-274.
Non-patent document 2: Hong et al., Appl Microbiol Biotechnol., 2003, vol. 63, p.4250.
Non-patent document 3: Zverlov et al., Microbiology, 2002, vol. 148, p.247-255.
Non-patent document 4: Zverlov et al., Microbiology, 1997, vol. 143, p.3537-3542.
Non-patent document 5: Kataeva et al., Journal of Bacteriology, 1999, vol. 181, p.5288-5295.
Non-patent document 6: Zhang et al., Biochemistry, 1995, vol. 34, p.3386-3395.
Non-patent document 7: Irwin et al., Eur J Biochem., 2000, vol. 267, p.4988-4997.
Non-patent document 8: Ruttersmith and Daniel, Biochemical Journal, 1991, vol. 277, p.887-890.
Non-patent document 9: Herai, S. et al., Proc. Natl. Acad. Sci. USA, 2004, vol. 101, p. 14031-14035
Non-patent document 10: Ogino, C., Appl. Microbiol. Biotechnol., 2004, vol. 64, p. 823-828
Non-patent document 11: Tamura, T. et al., J. Environmental Biotechnol., 2007, vol. 7, p.
3-10
Non-patent document 12: DN. Bolam et al., Biochem. J., 1998, vol. 331, p. 775-781
Non-patent document 13: N. DIN et al., 1994, Proc. Natl. Acad. Sci. USA, vol. 91, p. 11383-11387
Non-patent document 14: K. Riedel et al., FEMS Microbiology Letters, 1998, vol. 164, p. 261-267
Non-patent document 15: Mahadevan SA, Wi SG, Lee DS, Bae HJ: Site-directed mutagenesis and CBM engineering of Cel5A (Thermotoga maritima). FEMS Microbiol Lett., 2008, vol. 287, p. 205-211

SUMMARY OF THE INVENTION

Problems to be Solved by the Invention

It is an object of the present invention to provide a novel thermostable cellobiohydrolase which exhibits cellobiohydrolase activity at least at a temperature of 75° C. a polynucleotide that encodes the thermostable cellobiohydrolase, an expression vector for expressing the thermostable cellobiohydrolase, a transformant incorporated with the expression vector, and a method for producing a cellulose degradation product using the thermostable cellobiohydrolase.

Means for Solving the Problem

In order to solve the above-mentioned problems, the inventors of the present invention have successfully obtained thermostable cellobiohydrolases having novel amino acid sequences by extracting DNA directly from hot spring high temperature soils and conducting large-scale metagenome sequencing of hardly culturable microbiota. This has led to the completion of the present invention.

A thermostable cellobiohydrolase, a polynucleotide, an expression vector, a transformant, a method for producing a thermostable cellobiohydrolase, a cellulase mixture, a method for producing a cellulose degradation product, a method for producing a polynucleotide and a primer according to the present invention have the aspects [1] to [17] described below.

[1] A first aspect of the present invention is a thermostable cellobiohydrolase including a cellobiohydrolase catalytic domain which includes:
(A) a polypeptide including the amino acid sequence represented by SEQ ID NO: 1,
(B) a polypeptide including an amino acid sequence in which one or several amino acids are deleted, substituted, or added in the amino acid sequence represented by SEQ ID NO: 1, and having cellobiohydrolase activity at least under conditions of a temperature of 75° C. and a pH of 5.5,
(C) a polypeptide including an amino acid sequence having 80% or greater sequence identity with the amino acid sequence represented by SEQ ID NO: 1, and having cellobiohydrolase activity at least under conditions of a temperature of 75° C. and a pH of 5.5,
(D) a polypeptide including the amino acid sequence represented by SEQ ID NO: 3,
(E) a polypeptide including an amino acid sequence in which one or several amino acids are deleted, substituted, or added in the amino acid sequence represented by SEQ ID NO: 3, and having cellobiohydrolase activity at least under conditions of a temperature of 75° C. and a pH of 5.5,
(F) a polypeptide including an amino acid sequence having 80% or greater sequence identity with the amino acid sequence represented by SEQ ID NO: 3, and having cellobiohydrolase activity at least under conditions of a temperature of 75° C. and a pH of 5.5,
(G) a polypeptide including the amino acid sequence represented by SEQ ID NO: 5,
(H) a polypeptide including an amino acid sequence in which one or several amino acids are deleted, substituted, or added in the amino acid sequence represented by SEQ ID NO: 5, and having cellobiohydrolase activity at least under conditions of a temperature of 75° C. and a pH of 5.5,
(I) a polypeptide including an amino acid sequence having 80% or greater sequence identity with the amino acid sequence represented by SEQ ID NO: 5, and having cellobiohydrolase activity at least under conditions of a temperature of 75° C. and a pH of 5.5,
(J) a polypeptide including the amino acid sequence represented by SEQ ID NO: 7,
(K) a polypeptide including an amino acid sequence in which one or several amino acids are deleted, substituted, or added in the amino acid sequence represented by SEQ ID NO: 7, and having cellobiohydrolase activity at least under conditions of a temperature of 75° C. and a pH of 5.5, or
(L) a polypeptide including an amino acid sequence having 80% or greater sequence identity with the amino acid sequence represented by SEQ ID NO: 7, and having cellobiohydrolase activity at least under conditions of a temperature of 75° C. and a pH of 5.5.

[2] It is preferable that the above-mentioned thermostable cellobiohydrolase of [1] further includes a cellulose-binding module.

[3] A second aspect of the present invention is a polynucleotide including a region that encodes a cellobiohydrolase catalytic domain which includes:

(a) a nucleotide sequence that encodes a polypeptide including the amino acid sequence represented by SEQ ID NO: 1, (b) a nucleotide sequence that encodes a polypeptide including an amino acid sequence in which one or several amino acids are deleted, substituted, or added in the amino acid sequence represented by SEQ ID NO: 1, and having cellobiohydrolase activity at least under conditions of a temperature of 75° C. and a pH of 5.5, (c) a nucleotide sequence that encodes a polypeptide including an amino acid sequence having 80% or greater sequence identity with the amino acid sequence represented by SEQ ID NO: 1, and having cellobiohydrolase activity at least under conditions of a temperature of 75° C. and a pH of 5.5, (d) a nucleotide sequence that encodes a polypeptide including the amino acid sequence represented by SEQ ID NO: 3, (e) a nucleotide sequence that encodes a polypeptide including an amino acid sequence in which one or several amino acids are deleted, substituted, or added in the amino acid sequence represented by SEQ ID NO: 3, and having cellobiohydrolase activity at least under conditions of a temperature of 75° (and a pH of 5.5, (f) a nucleotide sequence that encodes a polypeptide including an amino acid sequence having 80% or greater sequence identity with the amino acid sequence represented by SEQ ID NO: 3, and having cellobiohydrolase activity at least under conditions of a temperature of 75° C. and a pH of 5.5, (g) a nucleotide sequence that encodes a polypeptide including the amino acid sequence represented by SEQ ID NO: 5, (h) a nucleotide sequence that encodes a polypeptide including an amino acid sequence in which one or several amino acids are deleted, substituted, or added in the amino acid sequence represented by SEQ ID NO: 5, and having cellobiohydrolase activity at least under conditions of a temperature of 75° C. and a pH of 5.5, (i) a nucleotide sequence that encodes a polypeptide including an amino acid sequence having 80% or greater sequence identity with the amino acid sequence represented by SEQ ID NO: 5, and having cellobiohydrolase activity at least under conditions of a temperature of 75° C. and a pH of 5.5, (j) a nucleotide sequence that encodes a polypeptide including the amino acid sequence represented by SEQ ID NO: 7, (k) a nucleotide sequence that encodes a polypeptide including an amino acid sequence in which one or several amino acids are deleted, substituted, or added in the amino acid sequence represented by SEQ ID NO: 7, and having cellobiohydrolase activity at least under conditions of a temperature of 75° C. and a pH of 5.5, (l) a nucleotide sequence that encodes a polypeptide including an amino acid sequence having 80% or greater sequence identity with the amino acid sequence represented by SEQ ID NO: 7, and having cellobiohydrolase activity at least under conditions of a temperature of 75° C. and a pH of 5.5, (m) a nucleotide sequence having 80% or greater sequence identity with a nucleotide sequence represented by SEQ ID NO: 2, 4, 6, or 8, and encoding a polypeptide having cellobiohydrolase activity at least under conditions of a temperature of 75° C. and a pH of 5.5, or (n) a nucleotide sequence of a polynucleotide which hybridizes with a polynucleotide including a nucleotide sequence represented by SEQ ID NO: 2, 4, 6, or 8 under a stringent condition, and being a nucleotide sequence that encodes a polypeptide having cellobiohydrolase activity at least under conditions of a temperature of 75° C. and a pH of 5.5.

[4] It is preferable that the above-mentioned polynucleotide of [3] further includes a region that encodes a cellulose-binding module.

[5] A third aspect of the present invention is an expression vector, which is incorporated with the above-mentioned polynucleotide of [3] or [4], and which is able to express a polypeptide having cellobiohydrolase activity at least under conditions of a temperature of 75° C. and a pH of 5.5, in a host cell.

[6] A fourth aspect of the present invention is a transformant, which is introduced with the above-mentioned expression vector of [5].

[7] It is preferable that the above-mentioned transformant of [6] is a eukaryotic microbe.

[8] It is preferable that the above-mentioned transformant of [6] is a plant.

[9] A fifth aspect of the present invention is a method for producing a thermostable cellobiohydrolase, including generating a thermostable cellobiohydrolase in the above-mentioned transformant of any one of [6] to [8].

[10] A sixth aspect of the present invention is a cellulase mixture, including the above-mentioned thermostable cellobiohydrolase of [1], the above-mentioned thermostable cellobiohydrolase of [2], or a thermostable cellobiohydrolase produced by the above-mentioned method for producing a thermostable cellobiohydrolase of [9], and at least one or more types of other cellulases.

[11] It is preferable in the above-mentioned cellulase mixture of [10] that the above-mentioned other cellulases are one or more types of cellulases selected from the group consisting of hemicellulase and endoglucanase.

[12] A seventh aspect of the present invention is a method for producing a cellulose degradation product, including generating a cellulose degradation product by contacting a cellulose-containing material to the above-mentioned thermostable cellobiohydrolase of [1], the above-mentioned thermostable cellobiohydrolase of [2], the above-mentioned transformant of any one of [6] to [8], or a thermostable cellobiohydrolase produced by the above-mentioned method for producing a thermostable cellobiohydrolase of [9].

[13] It is preferable in the above-mentioned method for producing a cellulose degradation product of [12] that at least one or more types of other cellulases are further contacted to the above-mentioned cellulose-containing material.

[14] It is preferable in the above-mentioned method for producing a cellulose degradation product of [13] that the above-mentioned other cellulases are one or more types of cellulases selected from the group consisting of hemicellulase and endoglucanase.

[15] An eighth aspect of the present invention is a method for producing a polynucleotide that encodes a thermostable cellobiohydrolase, including conducting PCR using DNA derived from a biological organism or a reverse transcription product of RNA derived from a biological organism as a template, with a forward primer including the nucleotide sequence represented by SEQ ID NO: 12 or a nucleotide sequence in which one or several nucleotides are added to the 5' end of the nucleotide sequence represented by SEQ ID NO: 12, and a reverse primer including the nucleotide sequence represented by SEQ ID NO: 13 or a nucleotide sequence in which one or several nucleotides are added to the 5' end of the nucleotide sequence represented by SEQ ID) NO: 13, and obtaining a polynucleotide including a nucleotide sequence that encodes a thermostable cellobiohydrolase as an amplification product.

[16] A ninth aspect of the present invention is a primer including the nucleotide sequence represented by SEQ ID NO: 12, or a nucleotide sequence in which one or several nucleotides are added to the 5' end of the nucleotide sequence represented by SEQ ID NO: 12.

[17] A tenth aspect of the present invention is a primer including the nucleotide sequence represented by SEQ ID NO: 13, or a nucleotide sequence in which one or several nucleotides are added to the 5' end of the nucleotide sequence represented by SEQ ID NO: 13.

Furthermore, the present invention includes the following aspects.

(1) A thermostable cellobiohydrolase having a cellobiohydrolase catalytic domain which includes:
(A) a polypeptide including the amino acid sequence represented by SEQ ID NO: 1,
(B) a polypeptide including an amino acid sequence in which one or several amino acids are deleted, substituted, or added in the amino acid sequence represented by SEQ ID NO: 1, and having cellobiohydrolase activity at least under conditions of a temperature of 75° C. and a pH of 5.5,
(C) a polypeptide including an amino acid sequence having 80% or greater but less than 100% sequence identity with the amino acid sequence represented by SEQ ID NO: 1, and having cellobiohydrolase activity at least under conditions of a temperature of 75° C. and a pH of 5.5,
(D) a polypeptide including the amino acid sequence represented by SEQ ID NO: 3,
(E) a polypeptide including an amino acid sequence in which one or several amino acids are deleted, substituted, or added in the amino acid sequence represented by SEQ ID NO: 3, and having cellobiohydrolase activity at least under conditions of a temperature of 75° C. and a pH of 5.5,
(F) a polypeptide including an amino acid sequence having 80% or greater but less than 100% sequence identity with the amino acid sequence represented by SEQ ID NO: 3, and having cellobiohydrolase activity at least under conditions of a temperature of 75° C. and a pH of 5.5,
(G) a polypeptide including the amino acid sequence represented by SEQ ID NO: 5,
(H) a polypeptide including an amino acid sequence in which one or several amino acids are deleted, substituted, or added in the amino acid sequence represented by SEQ ID) NO: 5, and having cellobiohydrolase activity at least under conditions of a temperature of 75° C. and a pH of 5.5,
(I) a polypeptide including an amino acid sequence having 80% or greater but less than 100% sequence identity with the amino acid sequence represented by SEQ ID NO: 5, and having cellobiohydrolase activity at least under conditions of a temperature of 75° C. and a pH of 5.5,
(J) a polypeptide including the amino acid sequence represented by SEQ ID NO: 7,
(K) a polypeptide including an amino acid sequence in which one or several amino acids are deleted, substituted, or added in the amino acid sequence represented by SEQ ID NO: 7, and having cellobiohydrolase activity at least under conditions of a temperature of 75° C. and a pH of 5.5, or
(L) a polypeptide including an amino acid sequence having 80% or greater but less than 100% sequence identity with the amino acid sequence represented by SEQ ID NO: 7, and having cellobiohydrolase activity at least under conditions of a temperature of 75° C. and a pH of 5.5.

(2) The thermostable cellobiohydrolase according to (1), further including a cellulose-binding module.

(3) A polynucleotide including a region that encodes a cellobiohydrolase catalytic domain which includes:
(a) a nucleotide sequence that encodes a polypeptide including the amino acid sequence represented by SEQ ID NO: 1,
(b) a nucleotide sequence that encodes a polypeptide including an amino acid sequence in which one or several amino acids are deleted, substituted, or added in the amino acid sequence represented by SEQ ID NO: 1, and having cellobiohydrolase activity at least under conditions of a temperature of 75° C. and a pH of 5.5,
(c) a nucleotide sequence that encodes a polypeptide including an amino acid sequence having 80% or greater but less than 100% sequence identity with the amino acid sequence represented by SEQ ID NO: 1, and having cellobiohydrolase activity at least under conditions of a temperature of 75° C. and a pH of 5.5,
(d) a nucleotide sequence that encodes a polypeptide including the amino acid sequence represented by SEQ ID NO: 3,
(e) a nucleotide sequence that encodes a polypeptide including an amino acid sequence in which one or several amino acids are deleted, substituted, or added in the amino acid sequence represented by SEQ ID NO: 3, and having cellobiohydrolase activity at least under conditions of a temperature of 75° C. and a pH of 5.5,
(f) a nucleotide sequence that encodes a polypeptide including an amino acid sequence having 80% or greater but less than 100% sequence identity with the amino acid sequence represented by SEQ ID NO: 3, and having cellobiohydrolase activity at least under conditions of a temperature of 75° C. and a pH of 5.5,
(g) a nucleotide sequence that encodes a polypeptide including the amino acid sequence represented by SEQ ID NO: 5,
(h) a nucleotide sequence that encodes a polypeptide including an amino acid sequence in which one or several amino acids are deleted, substituted, or added in the amino acid sequence represented by SEQ ID NO: 5, and having cellobiohydrolase activity at least under conditions of a temperature of 75° C. and a pH of 5.5,
(i) a nucleotide sequence that encodes a polypeptide including an amino acid sequence having 80% or greater but less than 100% sequence identity with the amino acid sequence represented by SEQ ID NO: 5, and having cellobiohydrolase activity at least under conditions of a temperature of 75° C. and a pH of 5.5,
(j) a nucleotide sequence that encodes a polypeptide including the amino acid sequence represented by SEQ ID NO: 7,
(k) a nucleotide sequence that encodes a polypeptide including an amino acid sequence in which one or several amino acids are deleted, substituted, or added in the amino acid sequence represented by SEQ ID NO: 7, and having cellobiohydrolase activity at least under conditions of a temperature of 75° C. and a pH of 5.5, (l) a nucleotide sequence that encodes a polypeptide including an amino acid sequence having 80% or greater but less than 100% sequence identity with the amino acid sequence represented by SEQ ID NO: 7, and having cellobiohydrolase activity at least under conditions of a temperature of 75° C. and a pH of 5.5, (m) a nucleotide sequence having 80% or greater but less than 100% sequence identity with a nucleotide sequence represented by SEQ ID NO: 2, 4, 6 or 8, and encoding a polypeptide having cellobiohydrolase activity at least under conditions of a temperature of 75° C. and a pH of 5.5, or (n) a nucleotide sequence of a polynucleotide which hybridizes with a polynucleotide including a nucleotide sequence represented by SEQ ID NO: 2, 4, 6 or 8 under a stringent condition, and being a nucleotide sequence that encodes a polypeptide having cellobiohydrolase activity at least under conditions of a temperature of 75° C. and a pH of 5.5.

(4) The polynucleotide according to (3), further including a region that encodes a cellulose-binding module.

(5) An expression vector, which is incorporated with the polynucleotide according to (3) or (4), and which is able to express, in a host cell, a polypeptide having cellobiohydrolase activity at least under conditions of a temperature of 75° C. and a pH of 5.5.

(6) A transformant, which is introduced with the expression vector according to (5).

(7) The transformant according to (6), which is a prokaryote.

(8) The transformant according to (6), which is a eukaryote.

(9) The transformant according to (6), which is a plant.

(10) A method for producing a thermostable cellobiohydrolase, the method including generating the thermostable cellobiohydrolase in the transformant according to any one of (6) to (9).

(11) A cellulase mixture, including the thermostable cellobiohydrolase according to (1), the thermostable cellobiohydrolase according to (2), or a thermostable cellobiohydrolase produced by the method for producing a thermostable cellobiohydrolase according to (10), and at least one type of other cellulase.

(12) The cellulase mixture according to (11), wherein the other cellulase is one or more types of cellulase selected from the group consisting of hemicellulase and endoglucanase.

(13) A method for producing a cellulose degradation product, the method including generating a cellulose degradation product by bringing a cellulose-containing material into contact with the thermostable cellobiohydrolase according to (1), the thermostable cellobiohydrolase according to (2), the transformant according to any one of (6) to (9), or a thermostable cellobiohydrolase produced by the method for producing a thermostable cellobiohydrolase according to (10).

(14) The method for producing a cellulose degradation product according to (13), wherein at least one type of other cellulase is also brought into contact with the cellulose-containing material.

(15) The method for producing a cellulose degradation product according to (14), wherein the other cellulase is one or more types of cellulase selected from the group consisting of hemicellulase and endoglucanase.

(16) A method for producing a polynucleotide that encodes a thermostable cellobiohydrolase, the method including conducting PCR using DNA derived from a biological organism or a reverse transcription product of RNA derived from a biological organism as a template, with a forward primer including the nucleotide sequence represented by SEQ ID NO: 12 or a nucleotide sequence in which one or several nucleotides are added to the 5' end of the nucleotide sequence represented by SEQ ID NO: 12, and a reverse primer including the nucleotide sequence represented by SEQ ID NO: 13 or a nucleotide sequence in which one or several nucleotides are added to the 5' end of the nucleotide sequence represented by SEQ ID) NO: 13, and obtaining a polynucleotide including a nucleotide sequence that encodes a thermostable cellobiohydrolase as an amplification product.

(17) A primer including the nucleotide sequence represented by SEQ ID NO: 12, or a nucleotide sequence in which one or several nucleotides are added to the 5' end of the nucleotide sequence represented by SEQ ID NO: 12.

(18) A primer including the nucleotide sequence represented by SEQ ID NO: 13, or a nucleotide sequence in which one or several nucleotides are added to the 5' end of the nucleotide sequence represented by SEQ ID NO: 13.

Effects of the Invention

The thermostable cellobiohydrolase according to the present invention has cellobiohydrolase activity at least at a temperature of 75° C. and a pH of 5.5. For this reason, the thermostable cellobiohydrolase is suitable for the enzymatic degradation of celluloses under high temperature conditions.

Moreover, the polynucleotide according to the present invention, an expression vector incorporated with the polynucleotide, and a transformant introduced with the expression vector therein are suitably used for the production of the thermostable cellobiohydrolase according to the present invention.

BRIEF DESCRIPTION OF THE DRAWINGS

FIG. 2A is an alignment representation of the amino acid sequences predicted by the open reading frames (AR19G-166, AR19G-12, and OJ1-1), and the amino acid sequence of the catalytic domain of the family 6 glycoside hydrolase of a mesophilic aerobic bacterium in the phylum Chloroflexi, *Herpetosiphon aurantiacus* DSM 785, which has the highest sequence identity with these amino acid sequences.

FIG. 2B is an alignment representation of the amino acid sequence predicted by the open reading frame OJ1-1, and the amino acid sequence of the cellulose-binding module CBM3 of a thermophilic aerobic bacterium *Caldibacillus cellulovorans*.

Figure 3A:
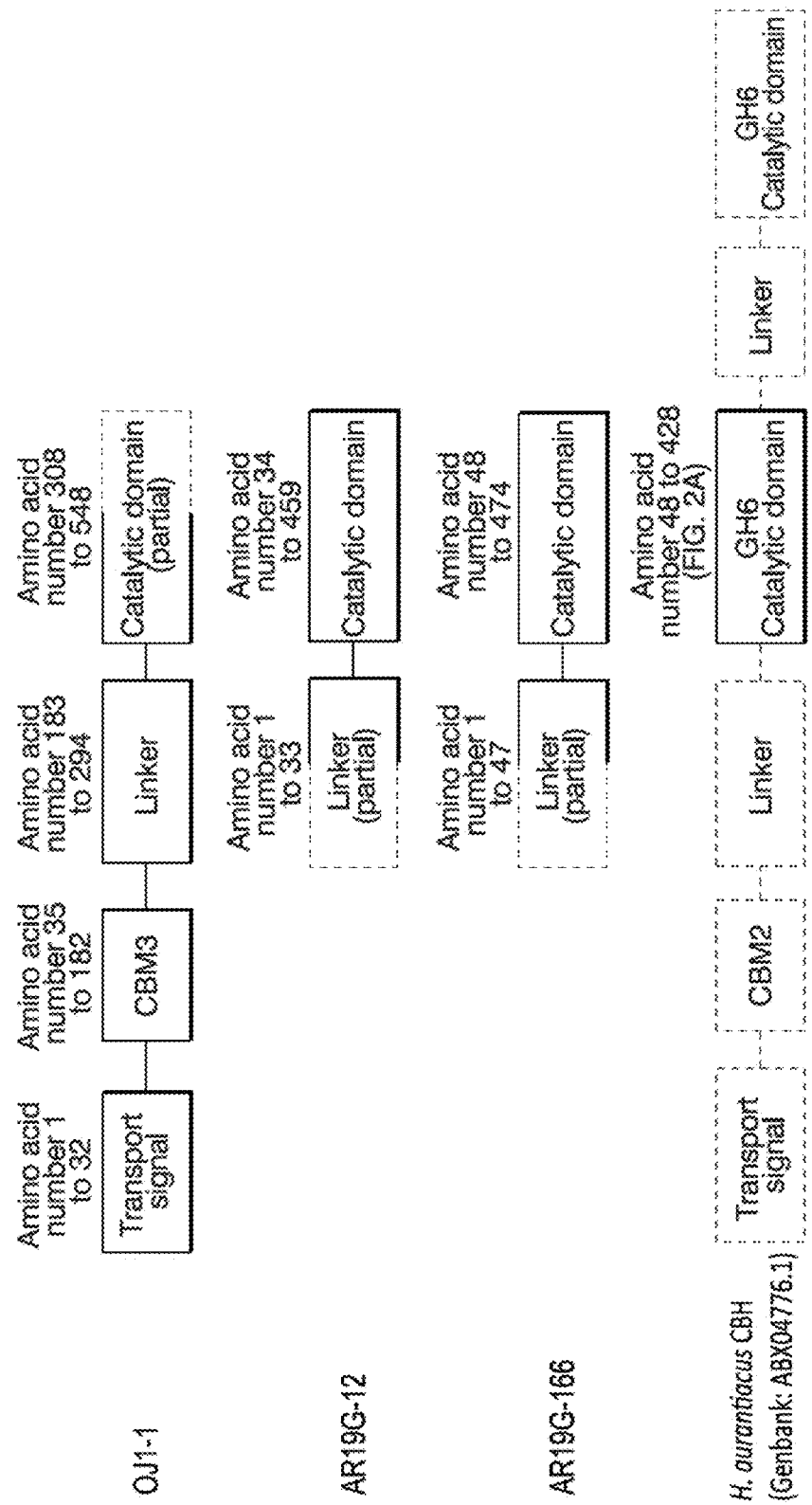
FIG. 3A is a schematic diagram of the amino acids of the polypeptides including the amino acid sequences predicted by the open reading frames (AR19G-166, AR19G-12, and OJ1-1), and the polypeptide predicted by the nucleotide sequence of the family 6 glycoside hydrolase of the mesophilic aerobic bacterium in the phylum Chloroflexi, *Herpe-* tosiphon aurantiacus DSM 785, which has the highest sequence identity with these amino acid sequences.
Figure 3B:
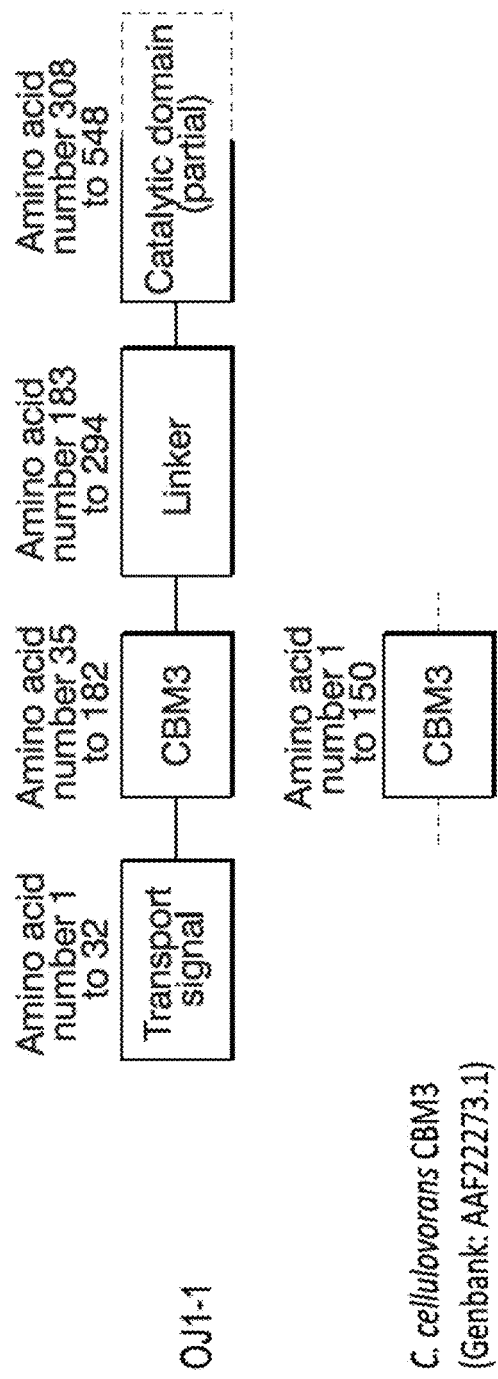

FIG. 3B is a schematic diagram of the amino acids of the polypeptide including the amino acid sequence predicted by the open reading frame OJ1-1 and the cellulose-binding module CBM3 of a thermophilic aerobic bacterium *Caldibacillus cellulovorans*.

Figure 4:
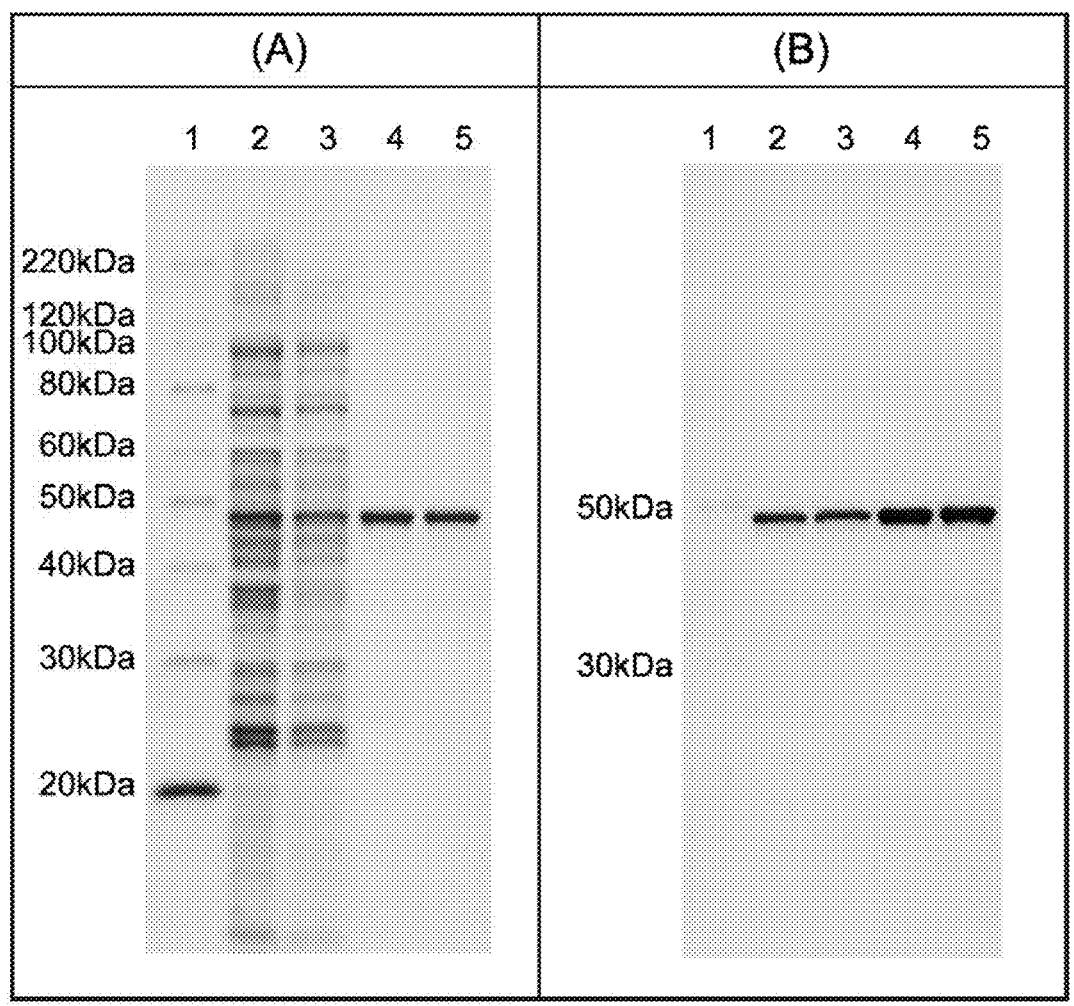

FIG. 4 shows the SDS-PAGE analysis result (A) and the Western blot analysis result (B) of the AR19G-166-RA protein and the AR19G-166-QV protein expressed by *E. coli* in Example 1. The lane 1 is a molecular weight marker for proteins, the lanes 2 and 3 show the electrophoresis patterns of the AR19G-166-RA and AR19G-166-QV gene recombinant *E. coli* homogenate supernatants, and the lanes 4 and 5 show the electrophoresis patterns of the purified AR19G-166-RA protein and AR19G-166-QV protein.

Figure 5A:
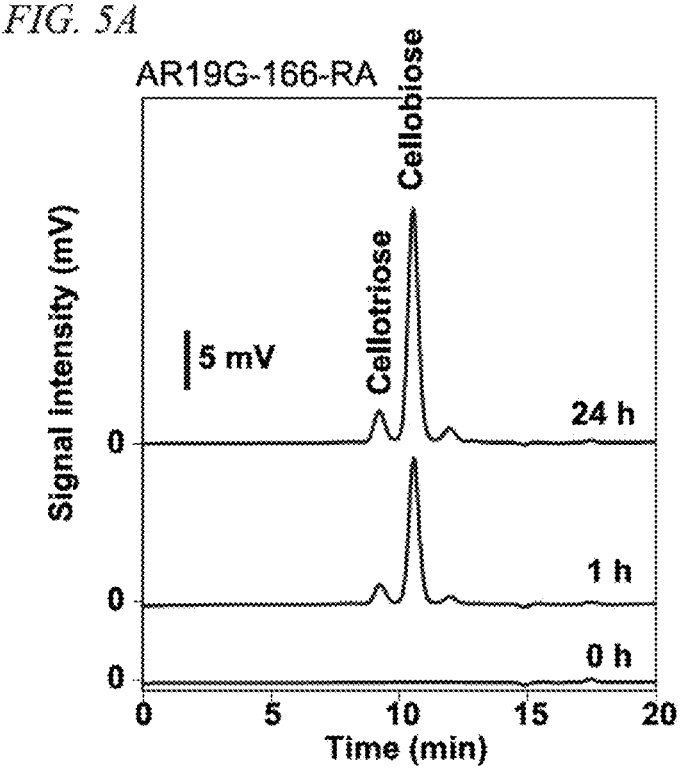

FIG. 5A shows the analysis result of the PSA hydrolysis reaction product of the AR19G-166-RA protein expressed by *E. coli*, by high-performance liquid chromatography (HPLC), in Example 1.

Figure 5B:
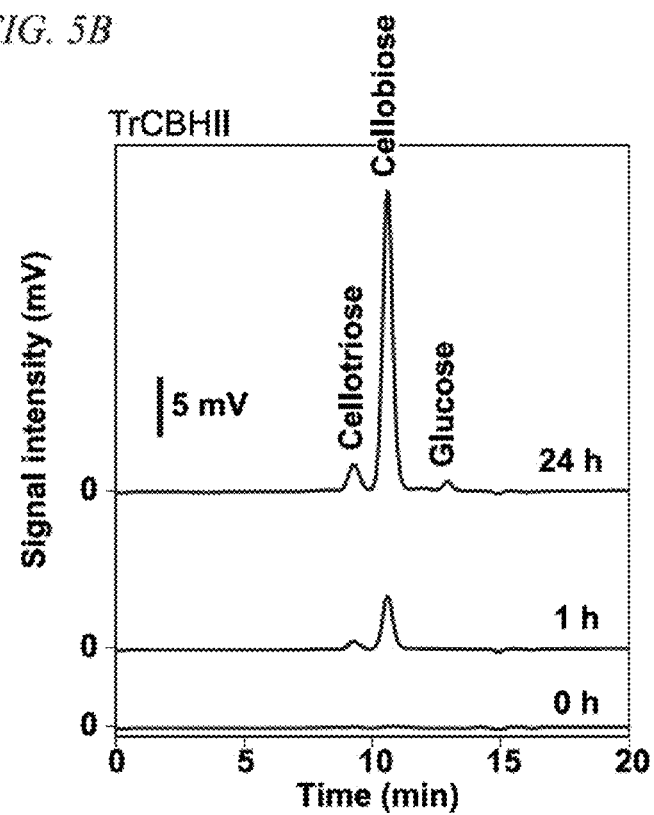

FIG. 5B shows the analysis result of the PSA hydrolysis reaction product of the family 6 cellobiohydrolase TrCBHII of a filamentous fungus *Trichoderma reesei*, by high-performance liquid chromatography (HPLC), in Example 1.

Figure 6A:
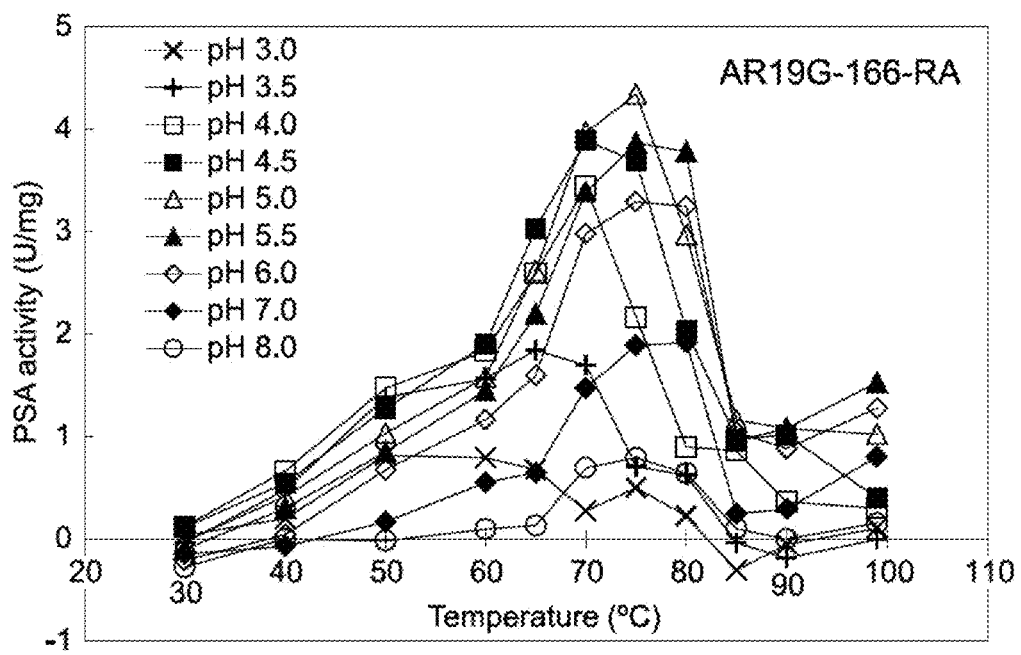

FIG. 6A is a graph showing the results of the PSA hydrolysis activity of the AR19G-166-RA protein expressed by *E. coli* measured at respective temperatures in Example 1.

Figure 6B:
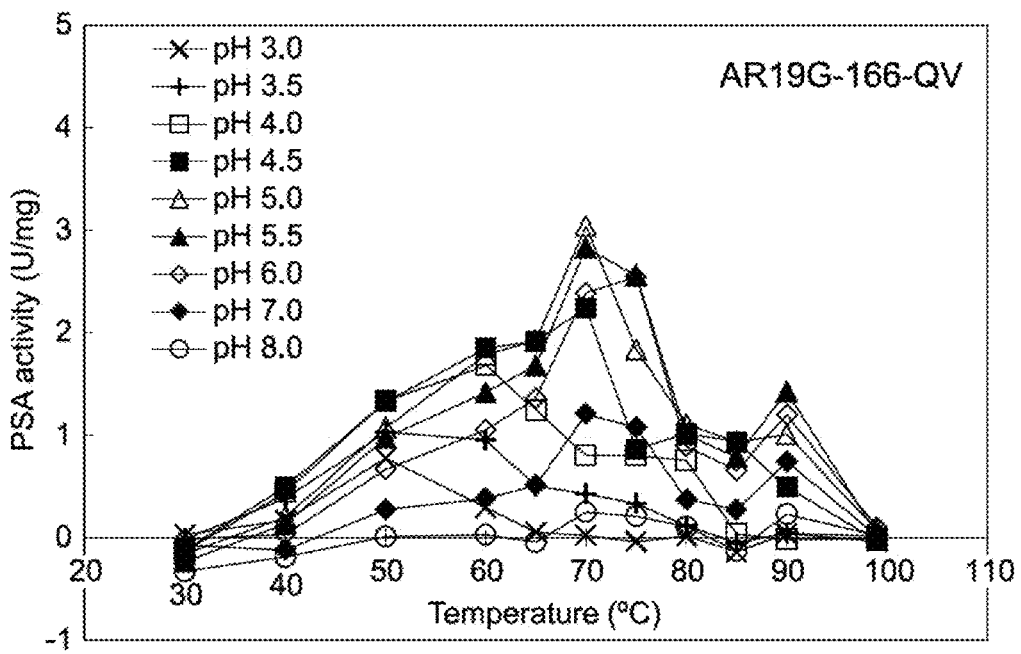

FIG. 6B is a graph showing the results of the PSA hydrolysis activity of the AR19G-166-H
QV protein expressed by *E. coli* measured at respective temperatures in Example 1.

Figure 7A:
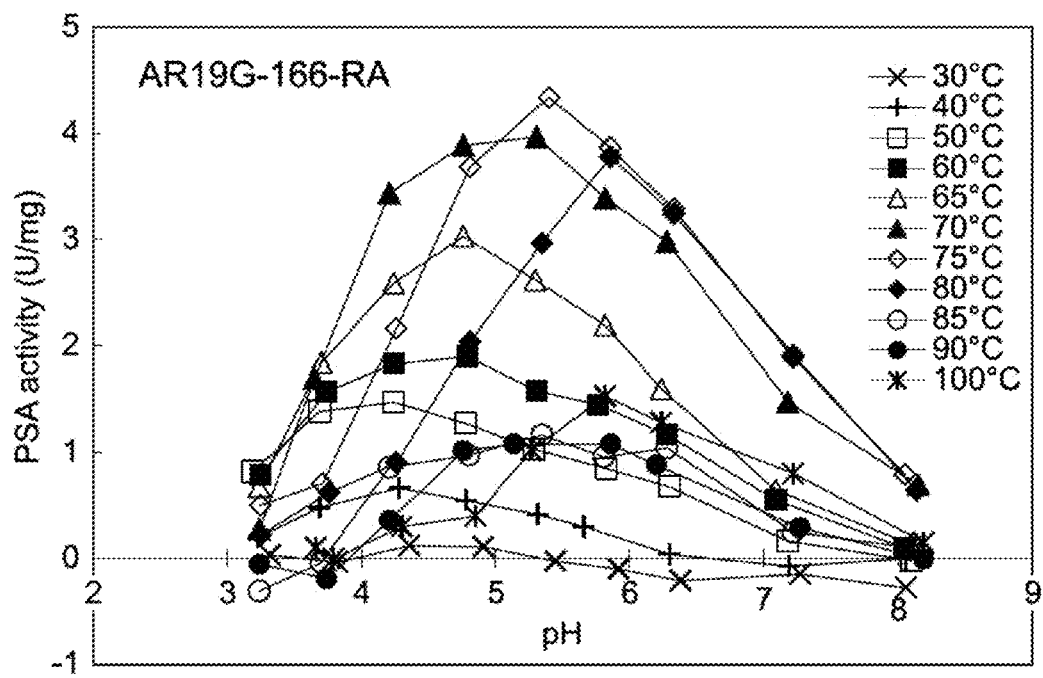

FIG. 7A is a graph showing the results of the PSA hydrolysis activity of the AR19G-166-RA protein expressed by *E. coli* measured at respective pH values in Example 1.

Figure 7B:
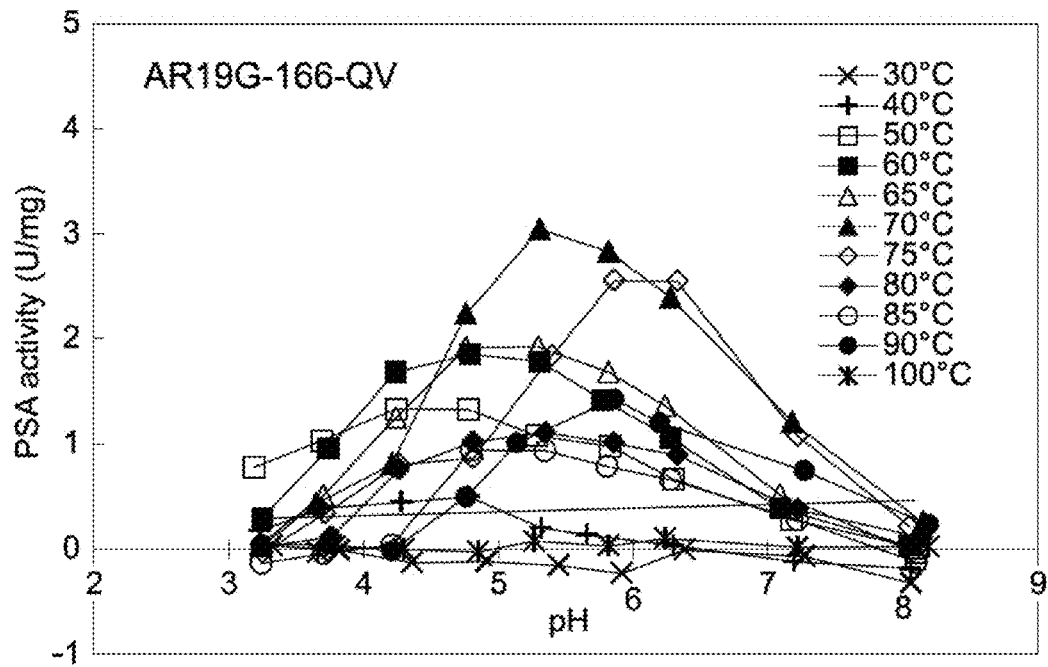

FIG. 7B is a graph showing the results of the PSA hydrolysis activity of the AR19G-166-QV protein expressed by *E. coli* measured at respective pH values in Example 1.

Figure 8A:
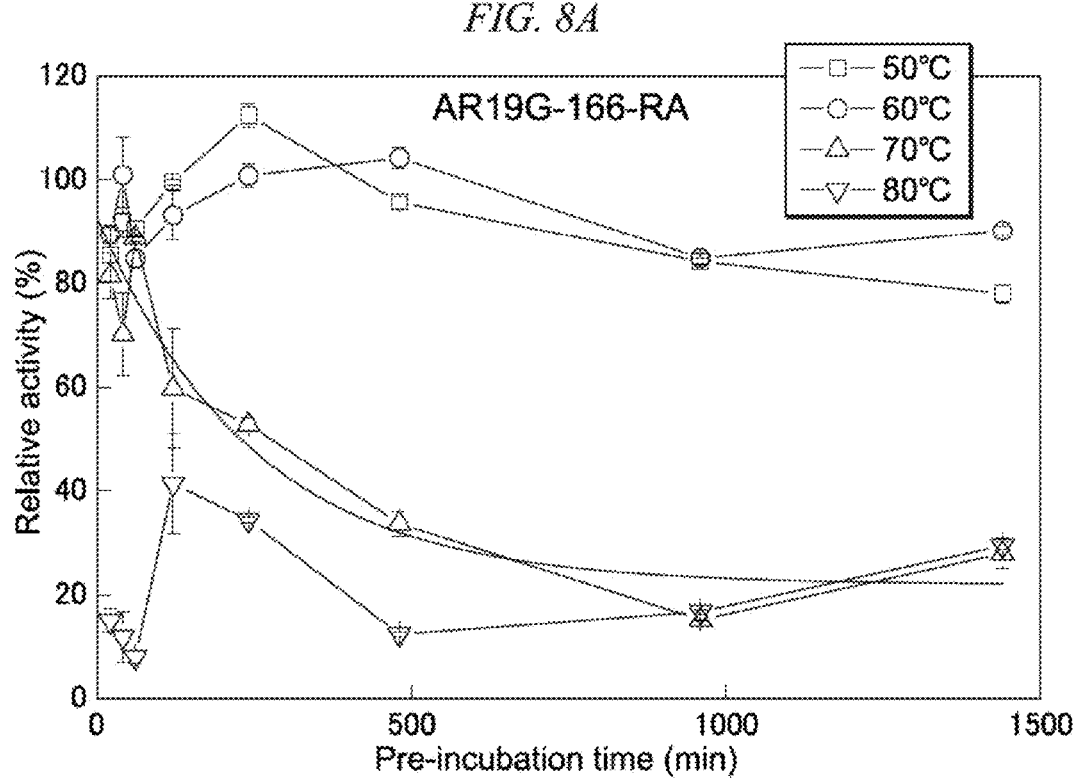

FIG. 8A is a graph showing the results of the influence of the preincubation time on the AR19G-166-RA protein expressed by *E. coli* measured in Example 1.

Figure 8B:
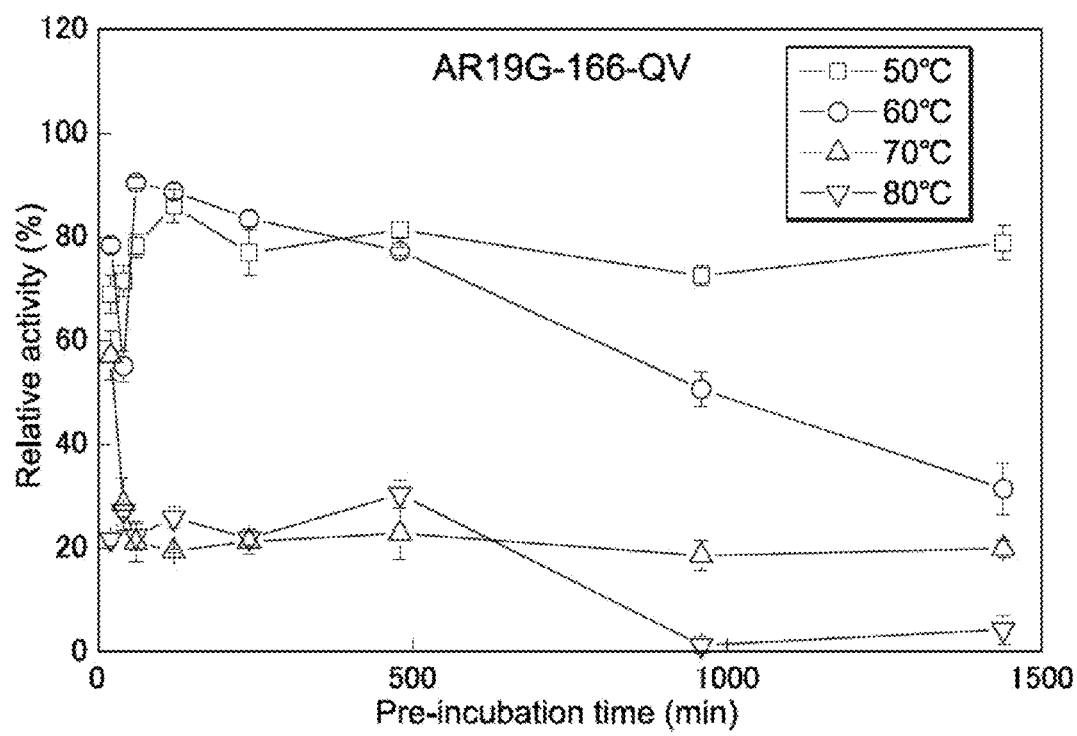

FIG. 8B is a graph showing the results of the influence of the preincubation time on the AR19G-66-QV protein expressed by *E. coli* measured in Example 1.

Figure 9A:
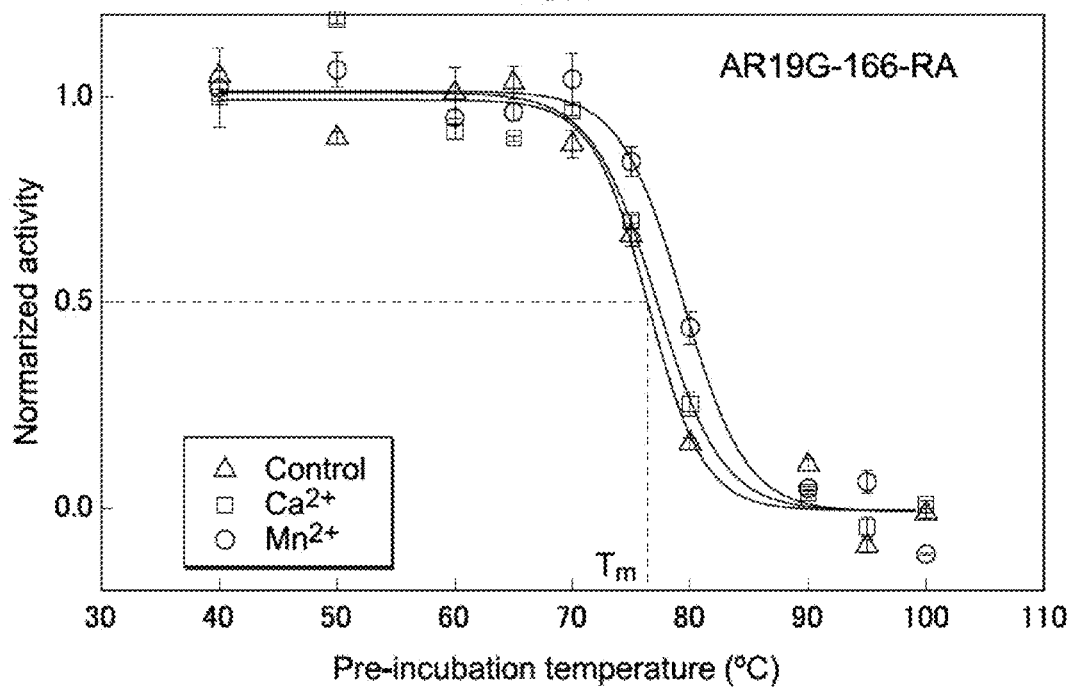

FIG. 9A is a graph showing the results of the influence of the preincubation temperature on the AR19G-166-RA protein expressed by *E. coli* measured in Example 1.

Figure 9B:
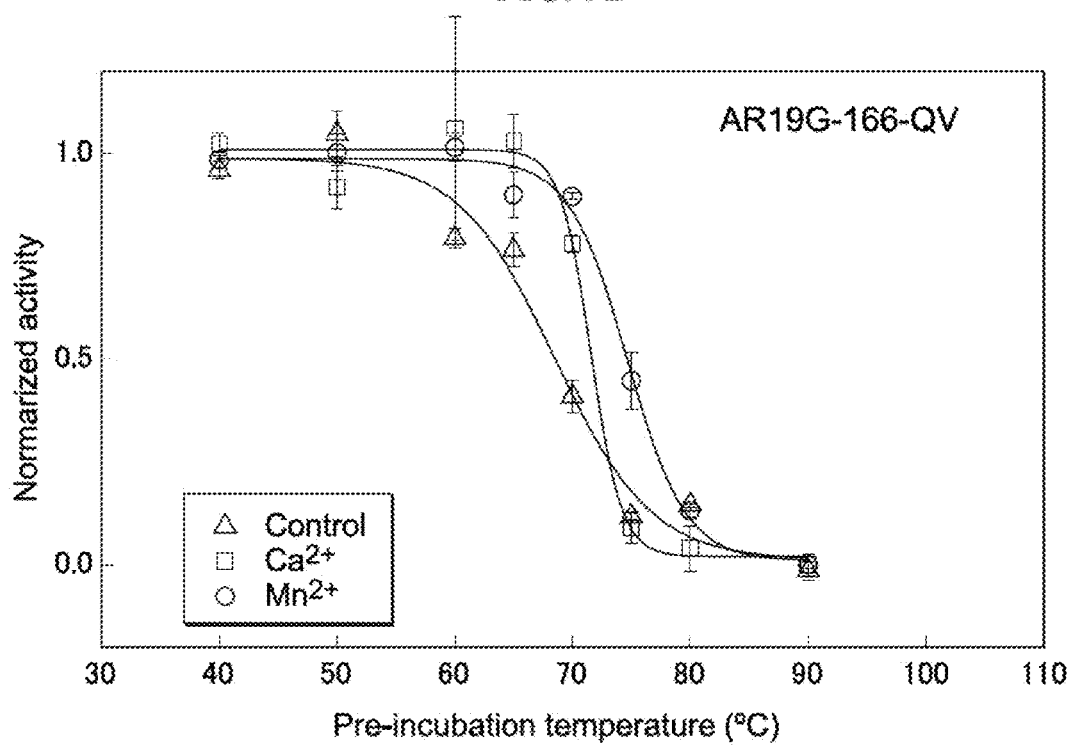

FIG. 9B is a graph showing the results of the influence of the preincubation temperature on the AR19G-166-QV protein expressed by *E. coli* measured in Example 1.

Figure 10:
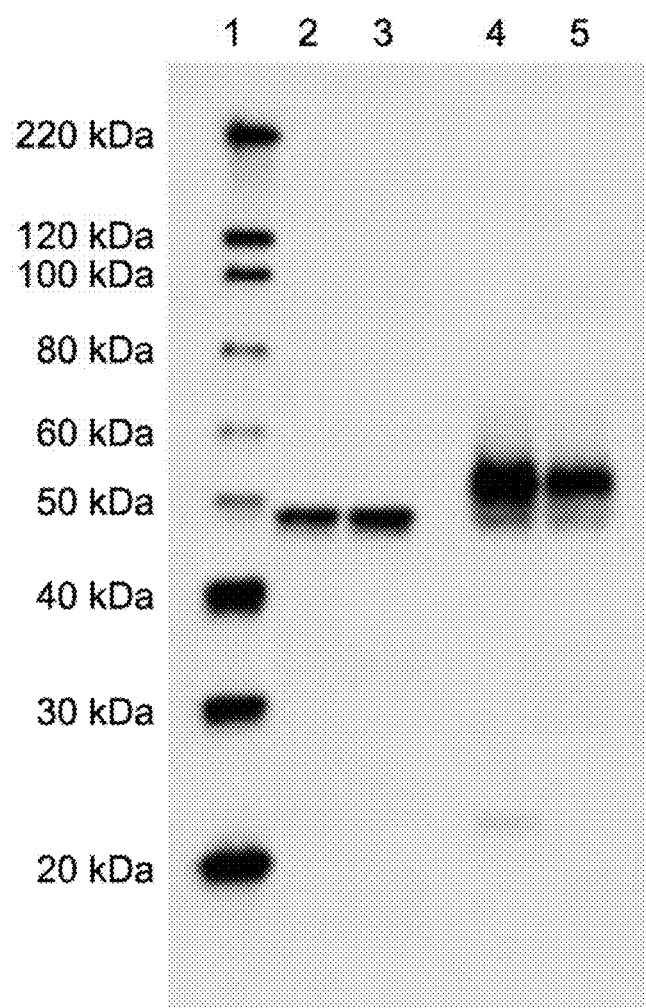

FIG. 10 shows the Western blot analysis result of medium supernatants of AR19G-166-RW gene-introduced *Aspergillus* transformant and R19G-166-QW gene-introduced *Aspergillus* transformant in Example 2, and AR19G-166-RA gene and AR19G-166-QV gene recombinant *E. coli* homogenate supernatants prepared in Example 1. The lanes 2 and 3 show very weak bands corresponding to the single bands of the AR19G-166 gene recombinant *E. coli* homogenate supernatant at 46.7kD, and strong and broad bands at 50 to 55 kDa.

Figure 11A:
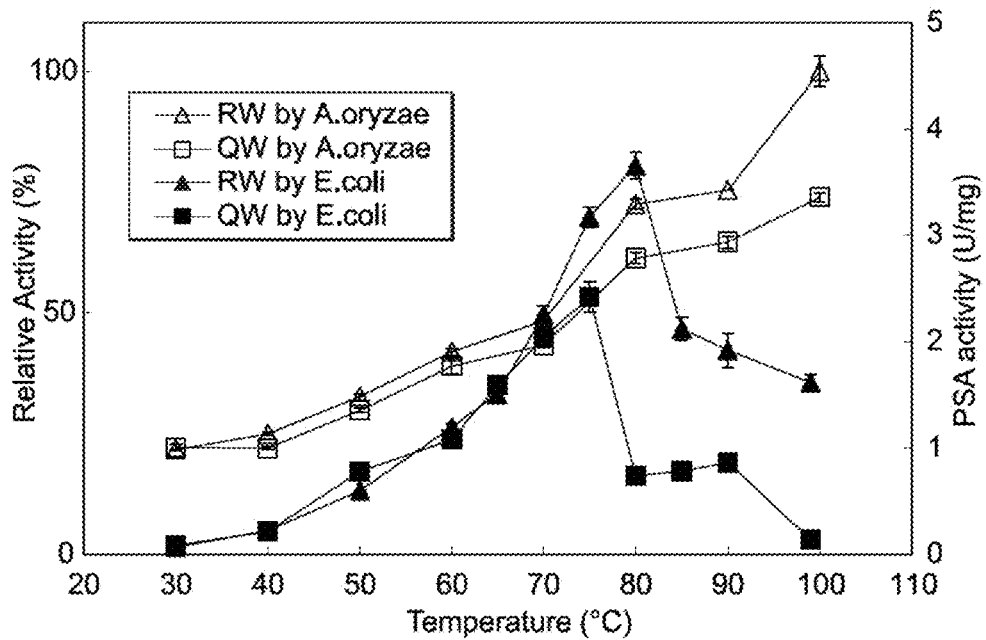

FIG. 11A shows the results of the PSA hydrolysis activity (U/mg) of the AR19G-166-RW protein and the AR19G-166-QW protein expressed by *E. coli* in Example 1, and the PSA hydrolysis activity (relative value (%)) of the AR19G-166-RW protein and the AR19G-166-QW protein expressed by *Aspergillus* in Example 2, at respective temperatures.

Figure 11B:
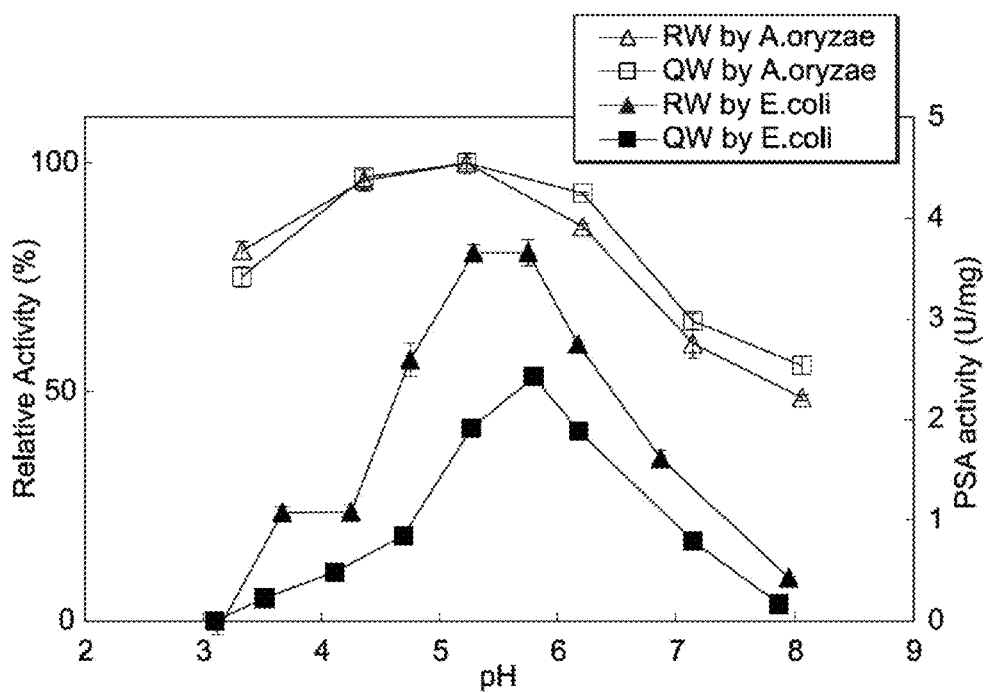

FIG. 11B shows the results of the PSA hydrolysis activity (U/mg) of the AR19G-166-RW protein and the AR19G-166-QW protein expressed by *E. coli* in Example 1, and the PSA hydrolysis activity (relative value (%)) of the AR19G-166-RW protein and the AR19G-166-QW protein expressed by *Aspergillus* in Example 2, at respective pH values.

Figure 12A:
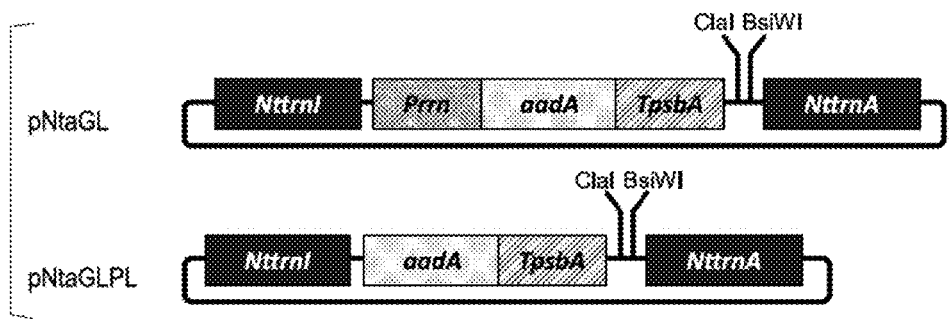

FIG. 12A is a schematic diagram of cassette vectors pNtaGL and pNtaGLPL for tobacco chloroplast transformation, used for the production of tobacco chloroplast transformants in Example 3.

Figure 12B:
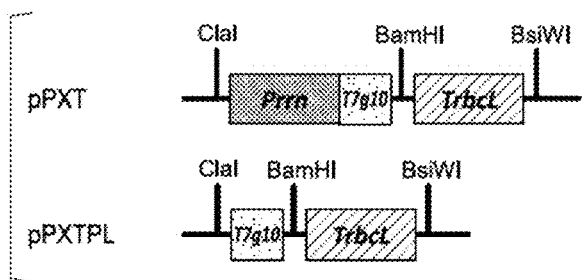

FIG. 12B is a schematic diagram of cassettes pPXT and pPXTPL for tobacco chloroplast transformation, used for the production of tobacco chloroplast transformants in Example 3.

Figure 12C:
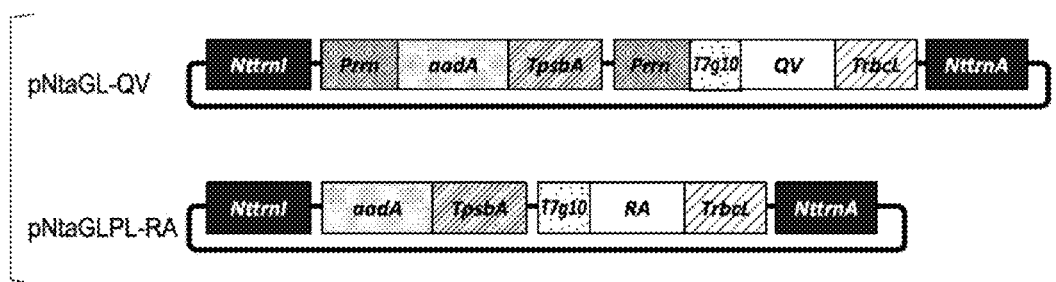

FIG. 12C is a schematic diagram of expression vectors pNtaGL-QV and pNtaGLPL-RA incorporated with expression cassettes for tobacco chloroplast transformation, used for the production of tobacco chloroplast transformants in Example 3.

Figure 13A:
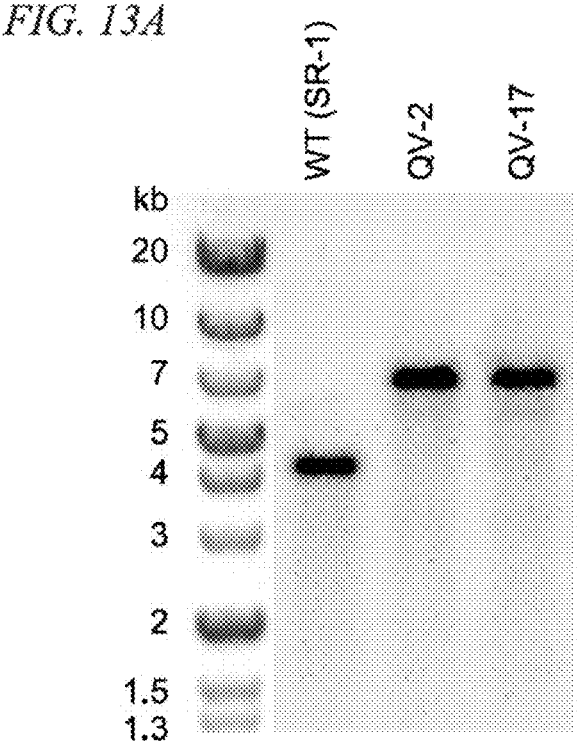

FIG. 13A shows a result of Southern hybridization of two lines of chloroplast transformant tobacco obtained by the introduction of pNTaGL-QV (QV-2 and QV-17) and wild-type tobacco (WT(SR-1)) in Example 3.

Figure 13B:
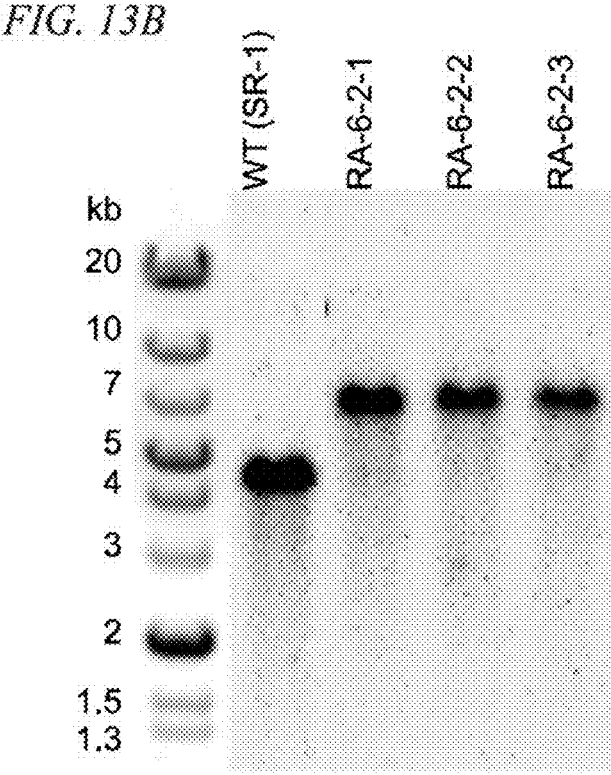

FIG. 13B shows a result of Southern hybridization of three lines of chloroplast transformant tobacco obtained by the introduction of pNtaGLPL-RA (RA-6-2-1, RA-6-2-2, and RA-6-2-3) and wild-type tobacco (WT(SR-1)) in Example 3.

Figure 13C:
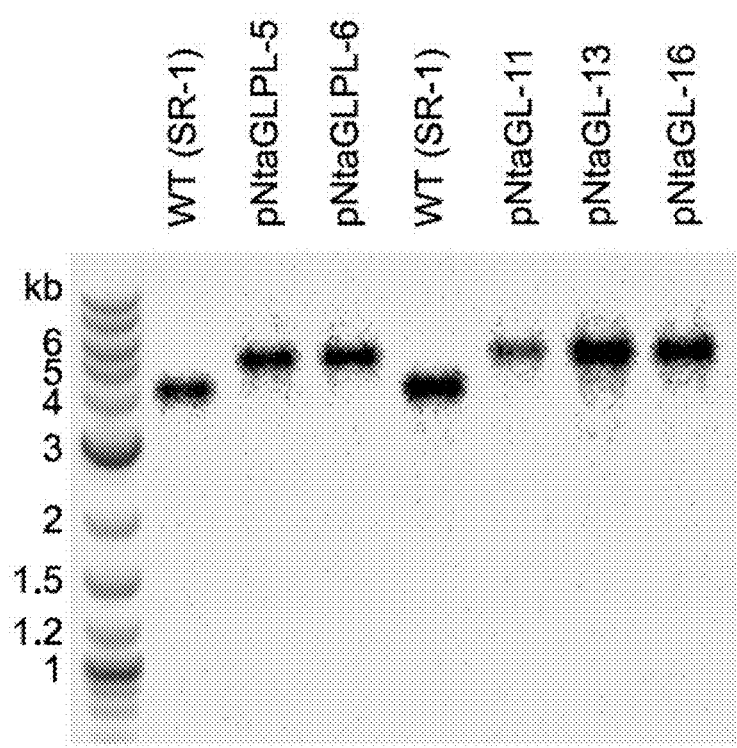

FIG. 13C is a diagram showing the results of Southern hybridization of chloroplast transgenic tobacco obtained by the introduction of pNtaGL and pNtaGLPL vectors in Example 3.

Figure 14A:
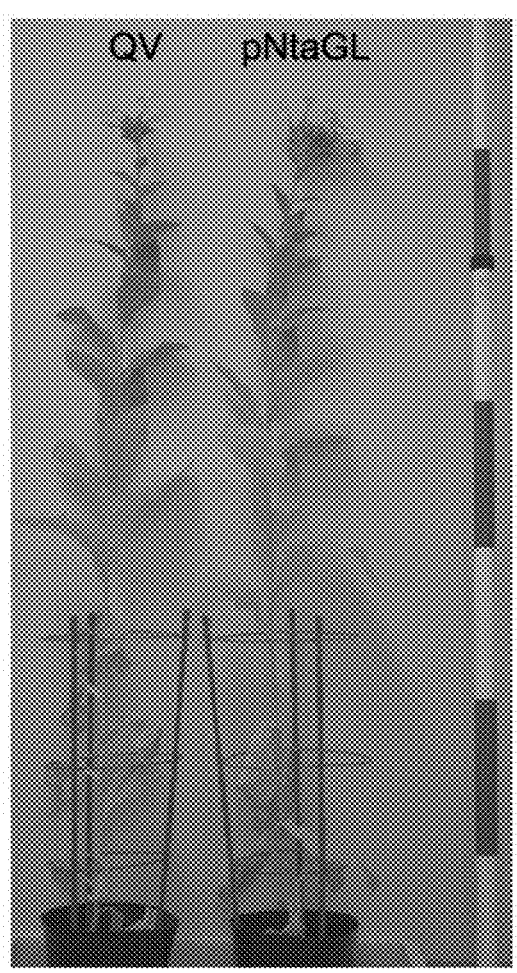
Figure 14B:

FIG. 14A is a photograph of a chloroplast transgenic tobacco plant ($T_1$ generation) obtained by the introduction of AR19G-166-QV and a wild-type tobacco (SR-1) on the FIG. 14B is a photograph of a chloroplast transgenic tobacco plant ($T_1$ generation), in the flowering period, obtained by the introduction of AR19G-166-RA, in Example 3.

Figure 15A:
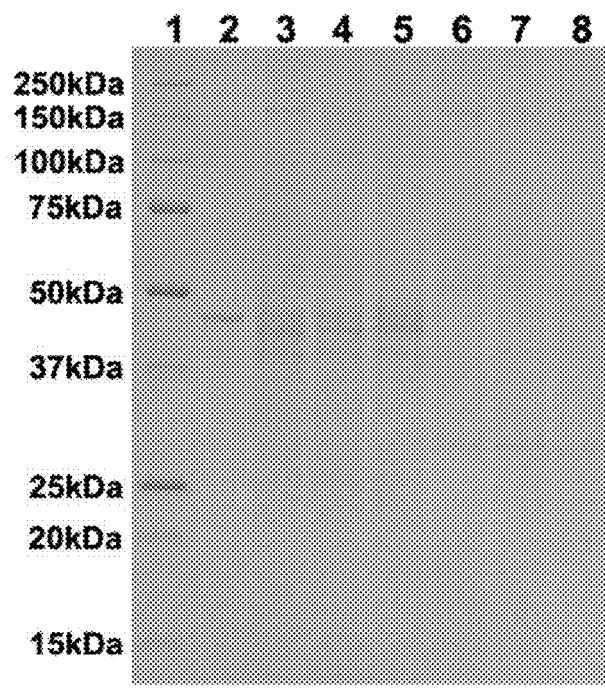

FIG. 15A is a diagram showing the results of SDS-PAGE analysis of soluble protein extracts extracted from the chloroplast transgenic tobacco plant obtained by the introduction of AR19G-166-QV and the chloroplast transgenic tobacco plant obtained by the introduction of pNtaGL in Example 3.

Figure 15B:
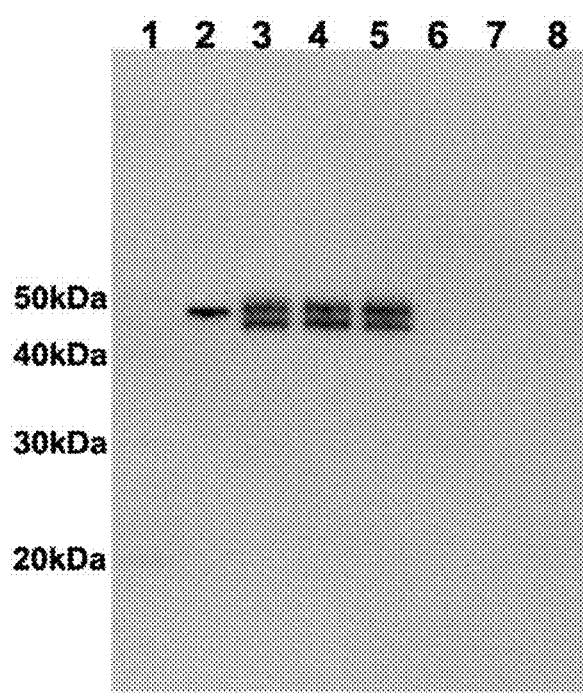

FIG. 15B is a diagram showing the results of Western blot analysis of soluble protein extracts extracted from the chloroplast transgenic tobacco plant obtained by the introduction of AR19G-166-QV and the chloroplast transgenic tobacco plant obtained by the introduction of pNtaGL in Example 3.

Figure 15C:
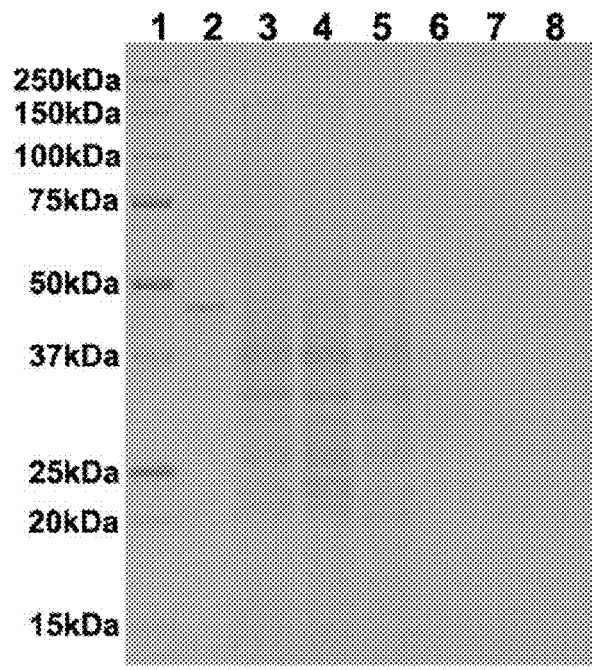

FIG. 15C is a diagram showing the results of SDS-PAGE analysis of soluble protein extracts extracted from the chloroplast transgenic tobacco plant obtained by the introduction of AR19G-166-RA and the chloroplast transgenic tobacco plant obtained by the introduction of pNtaGLPL in Example 3.

Figure 15D:
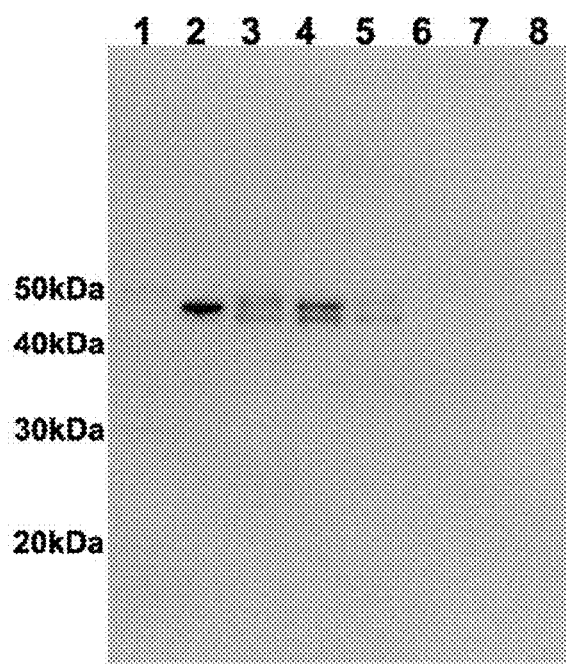

FIG. 15D is a diagram showing the results of Western blot analysis of soluble protein extracts extracted from the chloroplast transgenic tobacco plant obtained by the introduction of AR19G-166-RA and the chloroplast transgenic tobacco plant obtained by the introduction of pNtaGLPL in Example 3.

In each of FIG. 15A to FIG. 15D, lane 1 is a molecular weight marker for proteins, lane 2 is the purified enzymatic protein, lanes 3 to 5 are soluble protein extracts obtained from 3 individual chloroplast transgenic tobacco plants into which AR19G-166-QV or AR19G-166-RA has been introduced, and lanes 6 to 8 are soluble protein extracts obtained from 3 individual chloroplast transgenic tobacco plants into which pNtaGL or pNtaGLPL has been introduced.

Figure 16A:
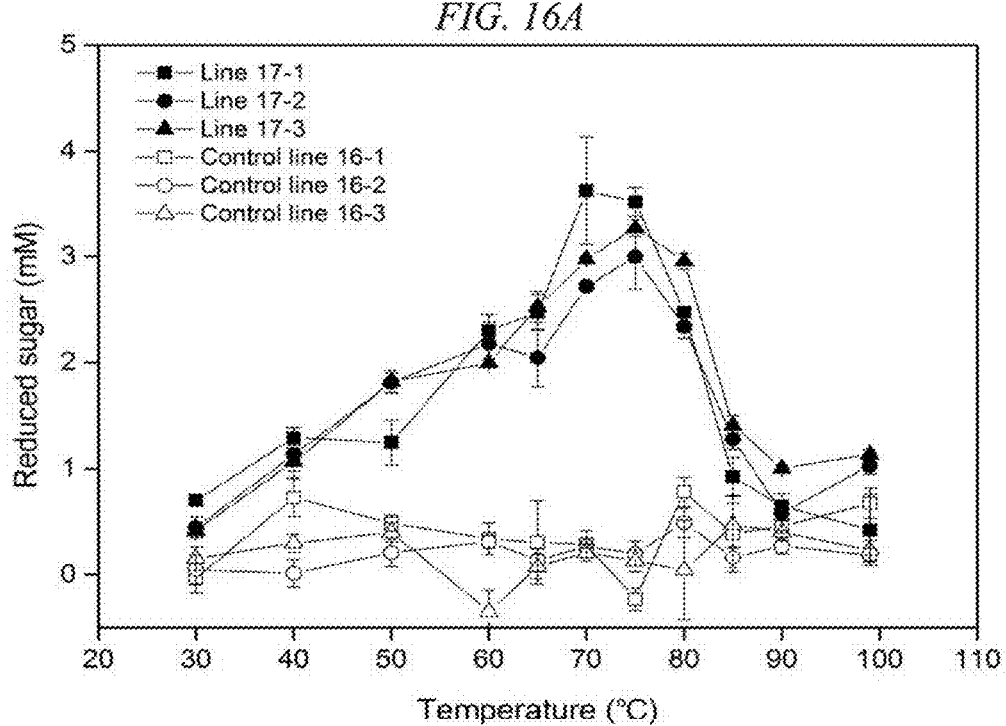

FIG. 16A is a diagram in which the PSA hydrolysis activity of the AR19G-166-QV protein expressed in the tobacco chloroplast in Example 3 is represented by the amount of reduced sugar (mM) at various temperatures.

Figure 16B:
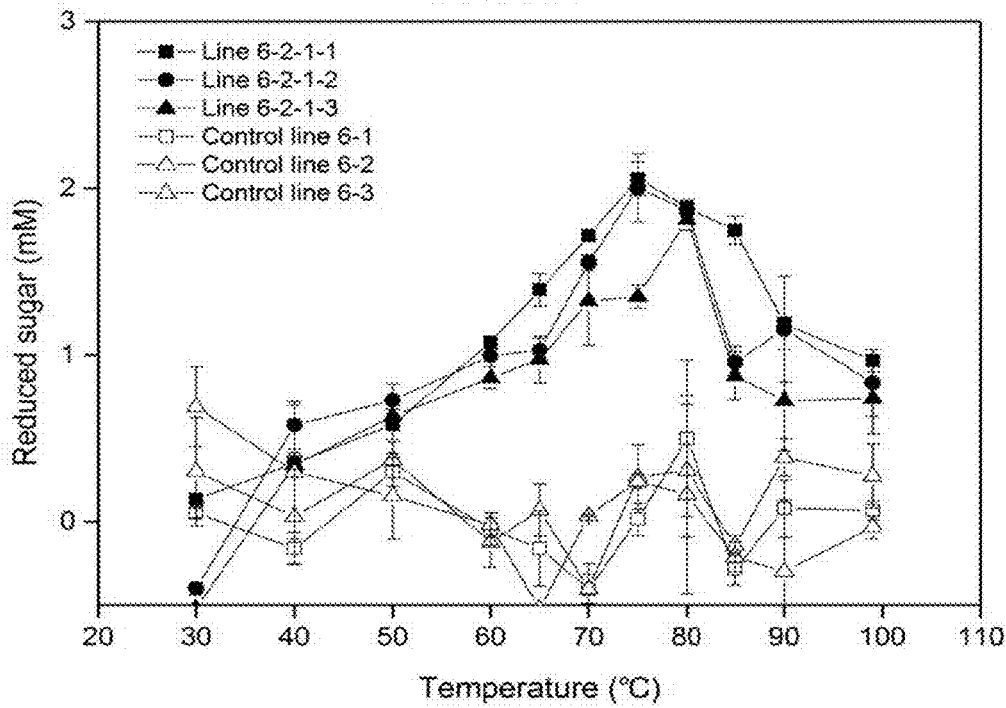

FIG. 16B is a diagram in which the PSA hydrolysis activity of the AR19G-166-RA protein expressed in the tobacco chloroplast in Example 3 is represented by the amount of reduced sugar (mM) at various temperatures.

Figure 17:
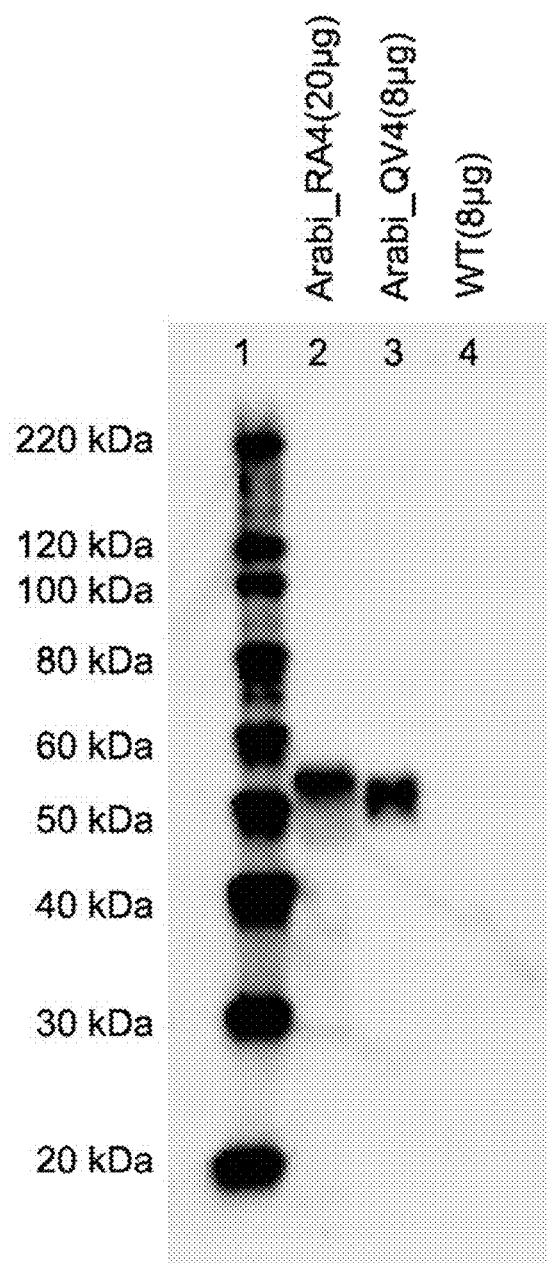

FIG. 17 is a diagram showing the results of Western blot analysis of the AR19G-166-RA protein and the AR19G-166-QV protein expressed in Arabidopsis thaliana in Example 4.

Figure 18:
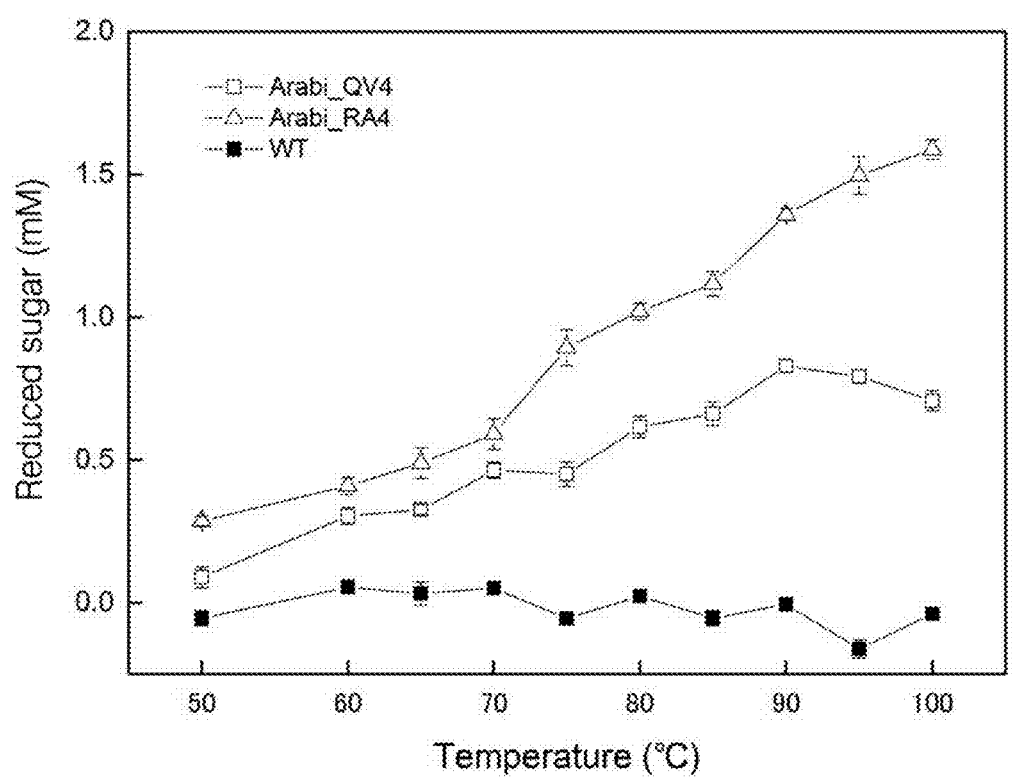

FIG. 18 is a diagram showing the temperature dependency of the PSA hydrolysis activities (mM of reduced sugar/20 min) of the AR19G-166-RA protein and the AR19G-166-QV protein expressed in Arabidopsis thaliana in Example 4.

Figure 19:
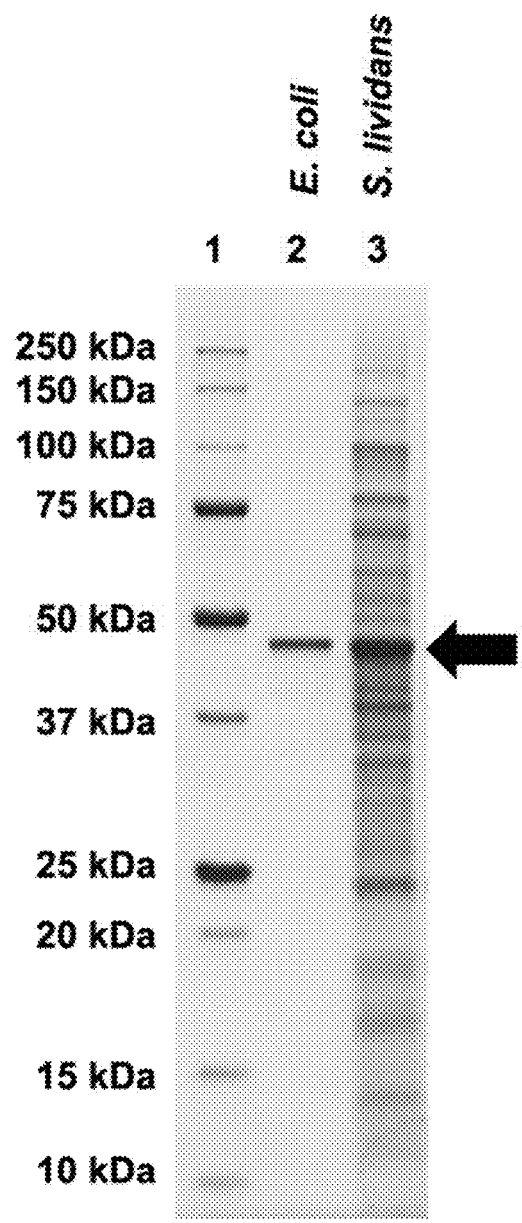

FIG. 19 is a diagram showing the results of SDS-PAGE analysis of cell-free extracts extracted from gene recombinant actinobacteria obtained by the introduction of AR19G-166-RA in Example 5.

Figure 20:
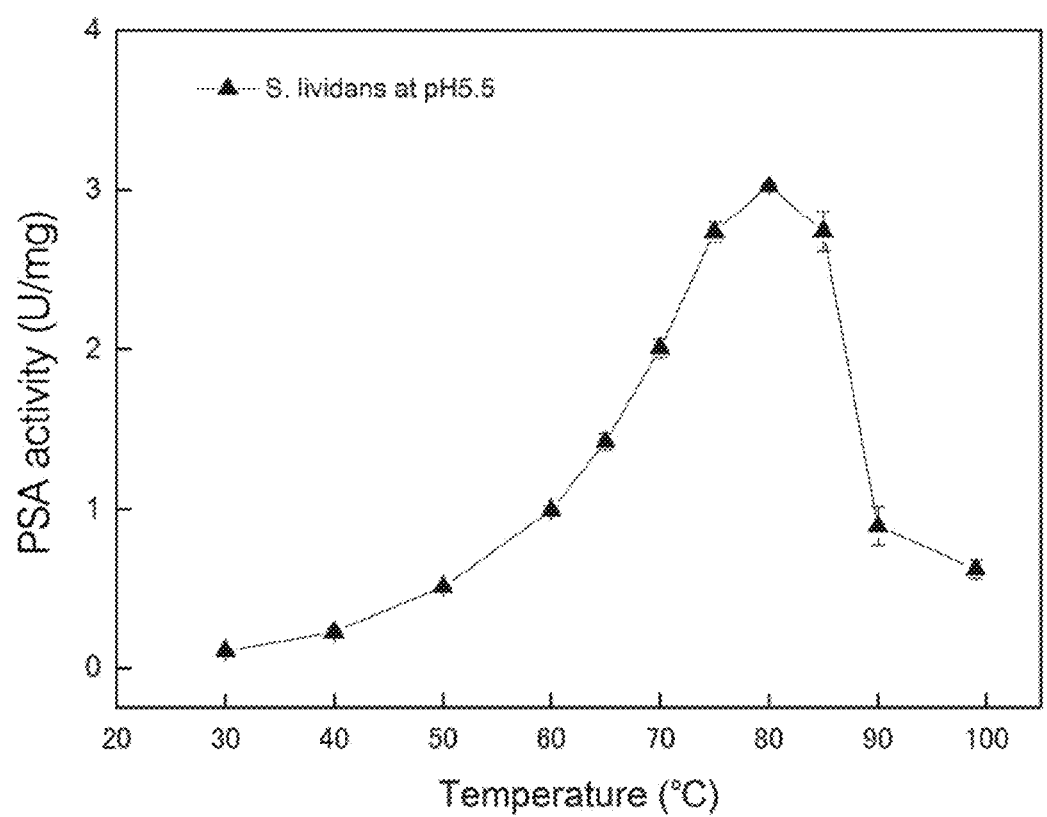

FIG. 20 is a diagram showing the temperature dependency of the phosphoric acid swollen Avicel (PSA) hydrolysis activity of the enzymatic protein (cell-free extract) encoded by the AR19G-166-RA gene, expressed in the actinobacterium Streptomyces lividans in Example 5.

Figure 21A:
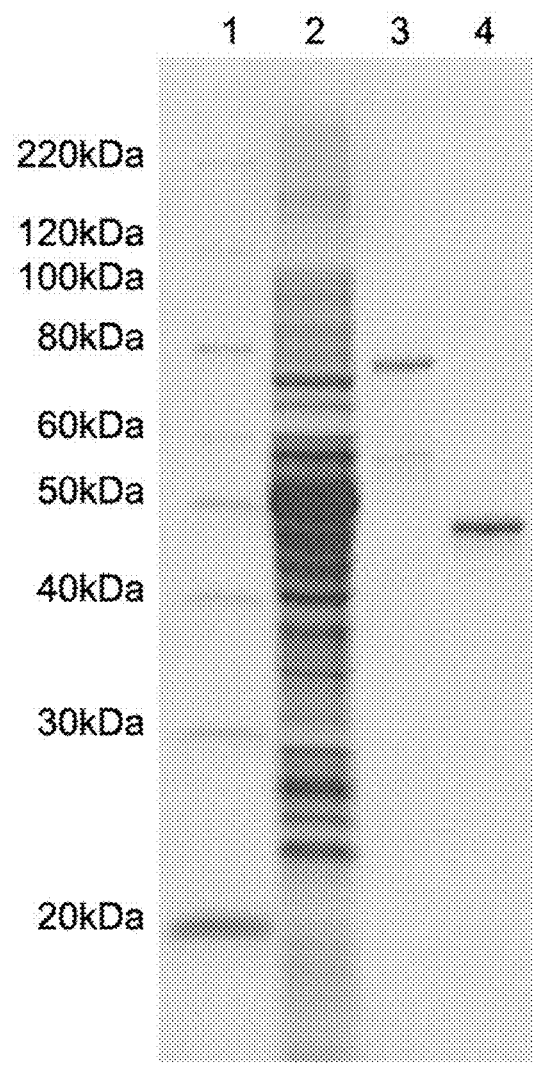

FIG. 21A is a diagram showing the results of SDS-PAGE analysis of the enzymatic protein obtained by expressing a CBM-added AR19G-166-RA protein in E. coli in Example 6.

Figure 21B:
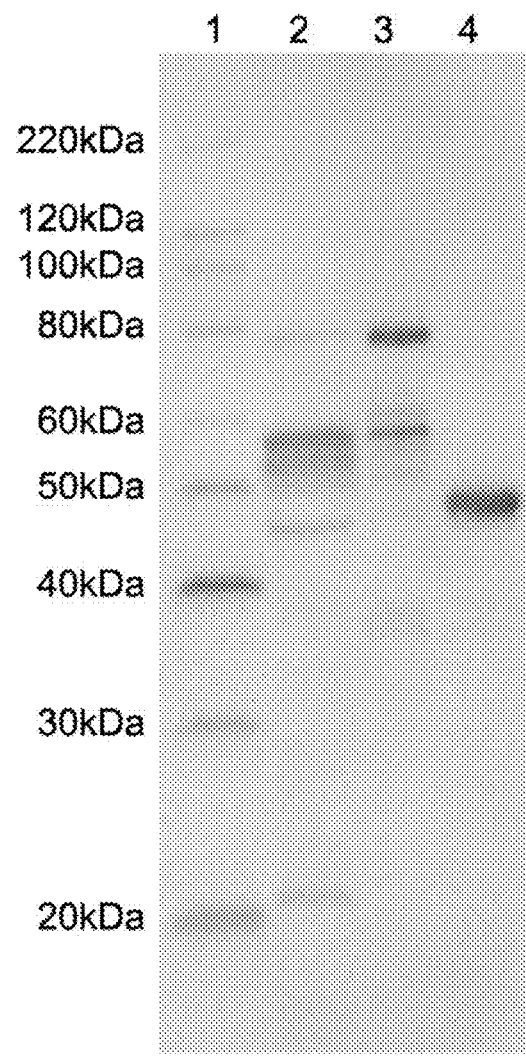

FIG. 21B is a diagram showing the results of Western blot analysis of the enzymatic protein obtained by expressing a CBM-added AR19G-166-RA protein in E. coli in Example 6.

In each FIG. 21A and FIG. 21B, lane 1 is a molecular weight marker for proteins, lane 2 is the gene recombinant E. coli homogenate supernatant, lane 3 is the purified CBM-added AR19G-166-RA protein, and lane 4 is the electrophoretic pattern of the cellobiohydrolase enzymatic protein purified in Example 1 <9>.

Figure 22A:
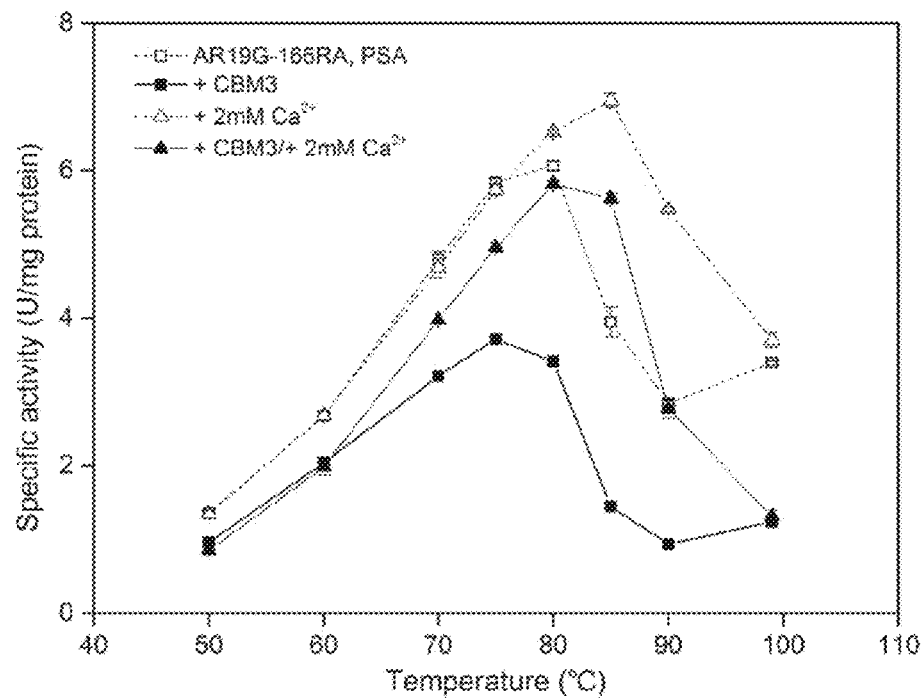

FIG. 22A is a diagram showing the temperature dependency of the PSA hydrolysis activity (U/mg) of the CBM-added AR19G-166-RA protein expressed in E. coli in Example 6.

Figure 22B:
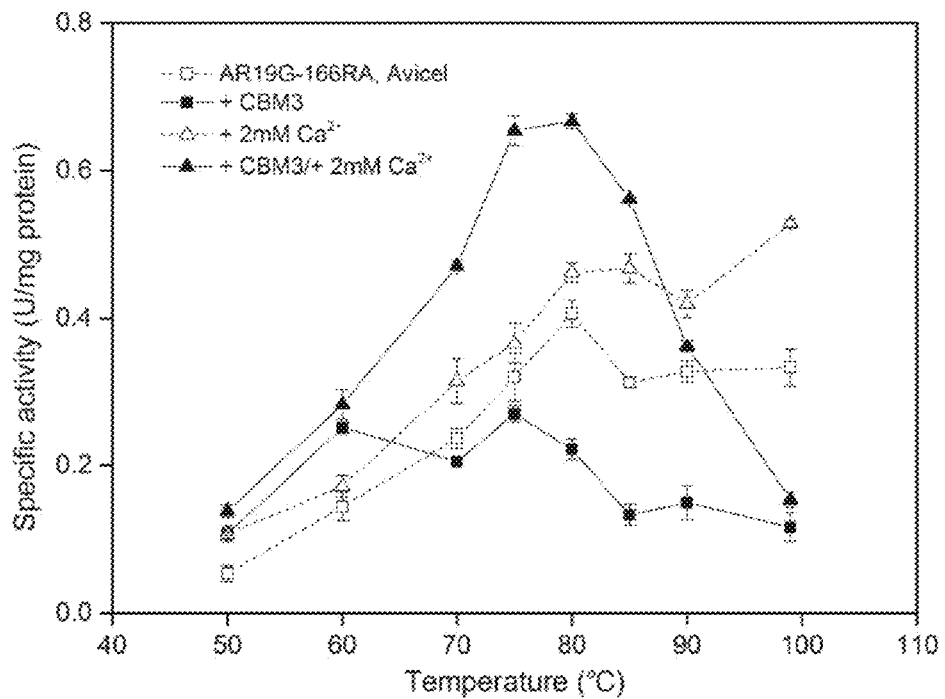

FIG. 22B is a diagram showing the temperature dependency of the Avicel degradation activity (U/mg) of the CBM-added AR19G-166-RA protein expressed in E. coli in Example 6.

DESCRIPTION OF THE EMBODIMENT

[Thermostable Cellobiohydrolase]

Many microorganisms including filamentous fungi, bacteria, and archaea are hardly culturable. It is said that 99% of fungi living in the microbial environment such as soil are unknown fungi. In particular, the culture of microorganisms living in high temperature environments is quite difficult, and it is thought that 0.1% or less population of the entire microorganisms living in soils have been only isolated and cultured with the current technology of microbial culture. This difficulty to culture such microorganisms living in high temperature soils is one factor to hinder the development of thermostable cellobiohydrolase.

Recently, it has become possible to conduct the whole genome sequencing of microbiota contained in soil and the like, because of the development of the next generation giga-sequencer enabling large amount sequencing of giga base pairs. Using this analysis technology, the metagenomic analysis method has been proposed in which the genome DNA of a microbial group is prepared from an environmental sample such as soil, the genomes of the miscellaneous group having nonuniform genomic compositions are directly and comprehensively sequenced, and the sequenced data are assembled by a parallel computer, so as to thereby reconstruct the genomic sequences of the microbiota. This has contributed to the rapid progress in the genome sequencing of hardly culturable microorganisms.

As shown in Example 1 described later, the inventors of the present invention prepared the genome DNA (metagenome DNA) of microbial groups from high temperature hot spring soils collected from five locations in Japan, and conducted shotgun sequencing and annotation of the metagenome DNA. By so doing, 44 open reading frames (ORFs) having amino acid sequences similar to known cellobiohydrolase enzymes were obtained. Primers were designed based on the nucleotide sequence information of these ORFs, and gene candidates were cloned from the metagenome DNA of the high temperature hot spring soils by the PCR method. The PCR-cloned DNAs were incorporated in E. coli, and proteins encoded by these nucleotide sequences were expressed. These were subjected to functional screenings by assays on the phosphoric acid swollen Avicel (PSA) degradation activity and the carboxymethyl cellulose (CMC) degradation activity. In the end, thermostable cellobiohydrolases having PSA degradation activity were obtained from a single ORF.

Two types of thermostable cellobiohydrolases in which two amino acids are substituted were obtained from the concerned ORF by PCR cloning. Of these two types of genotypes, one type in which the amino acid at position 299 is arginine (R) and the amino acid at position 351 is alanine (A) was referred to as AR19G-166-RA, and the other type in which the amino acid at position 299 is glutamine (Q) and the amino acid at position 351 is valine (V) was referred to as AR19G-166-QV. The nucleotide sequence of AR19G-166-RA is shown in SEQ ID NO: 2, and the amino acid sequence of AR19G-166-RA is shown in SEQ ID NO: 1. Moreover, the nucleotide sequence of AR19G-166-QV is shown in SEQ ID NO: 4, and the amino acid sequence of AR19G-166-QV is shown in SEQ ID NO: 3. AR19G-166-RA and AR19G-166-QV obtained by the PCR cloning had no initiating methionine. Therefore, these were suggested to be partial genes having only the cellobiohydrolase catalytic domain of the cellobiohydrolase gene, which had been of a microorganism contained in the above-mentioned high temperature hot spring soil.

As shown in Example 1 described later and the like, AR19G-166-RA and AR19G-166-QV exhibited high hydrolysis activity for PSA, and exhibited degradation activity, although it was weak, for lichenan composed of β-1,3 and β-1,4 linked glucans and Avicel which is a crystalline cellulose. On the other hand, they exhibited almost no degradation activity for CMC and laminarin composed of β-1,3 and β-1,6 linked glucans. High-performance liquid chromatography (HPLC) analysis was performed, in which AR19G-166-RA hydrolyzed PSA and generated cellobiose and a small amount of cellotriose. Moreover, the amino acid sequences of AR19G-166-RA and AR19G-166-QV were searched in publicly known amino acid sequence databases, resulting that the amino acid sequence showing the highest sequence identity was of a glycoside hydrolase (SEQ ID NO: 15) belonging to the GH6 family of an already known mesophilic aerobic bacterium in the phylum Chloroflexi,

*Herpetosiphon aurantiacus* DSM 785, with sequence identity of only 66%. It was elucidated from the substrate specificity, the HPLC analysis of the PSA hydrolysis reaction product, and the amino acid sequence identity (homology) with the already known cellobiohydrolase, that AR19G-166-RA and AR19G-166-QV were novel cellobiohydrolases belonging to the GH6 family.

Both of AR19G-166-RA and AR19G-166-QV have cellobiohydrolase activities at least under conditions of a temperature of 75° C. and a pH-1 of 5.5. Actually, as shown in Example 1 <13> described later, both AR19G-166-RA and AR19G-166-QV exhibit cellobiohydrolase activities in wide temperature ranges from 30 to 100° C. However, the optimum temperature ranges of these cellobiohydrolase activities were different. The cellobiohydrolase activity of AR19G-166-RA expressed by *E. coli* as a host tended to be increased as the temperature was increased within a range from 30 to 80° C., and the cellobiohydrolase activity tended to be decreased as the temperature was increased within a range from 80 to 100° C. On the other hand, the cellobiohydrolase activity of AR19G-166-QV tended to be increased as the temperature was increased within a range from 30 to 70° C., reaching to the peak around 70° C., and tended to be decreased as the temperature was increased within a range from 70 to 100° C.

In the present invention and the description of this application, the term "cellobiohydrolase activity" describes an activity wherein by using at least one compound selected from the group consisting of glucans containing β-1,3 and β-1,4 linkages and crystalline cellulose, and phosphoric acid swollen Avicel as the substrate, and performing hydrolysis of the substrate from the non-reducing end, cellobiose can be produced.

In the present invention and the description of this application, the expression "polypeptide having cellobiohydrolase activity at least under conditions of a temperature of 75*C and a pH of 5.5" means that when the pH of a solution containing the polypeptide is 5.5, the highest cellobiohydrolase activity is obtained at a temperature of 75° C. In other words, even if a solution containing the polypeptide lacks cellobiohydrolase activity under conditions other than a pH of 5.5 and a temperature of 75° C., provided the solution exhibits cellobiohydrolase activity when the conditions are set to a pH of 5.5 and a temperature of 75° C., the polypeptide is included within the scope of the present invention.

In the present invention and the description of this application, the "thermostable cellobiohydrolase" is preferably an enzyme having the aforementioned cellobiohydrolase activity at 55 to 80° C. and a pH of 3.5 to 7.0, and is more preferably an enzyme having the cellobiohydrolase activity at 70 to 100° C. and a pH of 4.0 to 6.0.

AR19G-166-RW in which the amino acid residue at position 351 is substituted with tryptophan (W) in AR19G-166-RA, and AR19G-166-QW in which the amino acid residue at position 351 is substituted with tryptophan (W) in AR19G-166-QV also have cellobiohydrolase activities at least under conditions of a temperature of 75° C. and a pH of 5.5, similarly to AR19G-166-RA and AR19G-166-QV. The amino acid sequence of AR19G-166-RW is shown in SEQ ID NO: 5, and the nucleotide sequence that encodes the same is shown in SEQ ID NO: 6. The amino acid sequence of AR19G-166-QW is shown in SEQ ID NO: 7, and the nucleotide sequence that encodes the same is shown in SEQ ID NO: 8. The cellobiohydrolase activities of AR19G-166-RW and AR19G-166-QW expressed by *Aspergillus* as a host were increased as the temperature was increased within a range from 30 to 100° C., and showed the highest cellobiohydrolase activity at 100° C.

Generally, in a protein having some kind of bioactivity, one or a plurality of amino acids can be deleted, substituted, or added, without deteriorating the bioactivity. That is, in AR19G-166-RA, AR19G-166-QV, AR19G-166-RW, or AR19G-166-QW, one or a plurality of amino acids can also be deleted, substituted, or added without deteriorating their cellobiohydrolase activities.

That is, the thermostable cellobiohydrolase serving as the first aspect of the present invention is a thermostable cellobiohydrolase having a cellobiohydrolase catalytic domain which includes any one of the followings (A) to (L).

(A) A polypeptide including the amino acid sequence represented by SEQ ID NO: 1.

(B) A polypeptide including an amino acid sequence in which one or several amino acids are deleted, substituted, or added in the amino acid sequence represented by SEQ ID NO: 1, as well as having cellobiohydrolase activity at least under conditions of a temperature of 75° C. and a pH of 5.5.

(C) A polypeptide including an amino acid sequence having 80% or greater but less than 100% sequence identity with the amino acid sequence represented by SEQ ID NO: 1, as well as having cellobiohydrolase activity at least under conditions of a temperature of 75° C. and a pH of 5.5.

(D) A polypeptide including the amino acid sequence represented by SEQ ID NO: 3.

(E) A polypeptide including an amino acid sequence in which one or several amino acids are deleted, substituted, or added in the amino acid sequence represented by SEQ ID NO: 3, as well as having cellobiohydrolase activity at least under conditions of a temperature of 75° C. and a pH of 5.5.

(F) A polypeptide including an amino acid sequence having 80% or greater but less than 100% sequence identity with the amino acid sequence represented by SEQ ID NO: 3, as well as having cellobiohydrolase activity at least under conditions of a temperature of 75° C. and a pH of 5.5.

(G) A polypeptide including the amino acid sequence represented by SEQ ID NO: 5.

(H) A polypeptide including an amino acid sequence in which one or several amino acids are deleted, substituted, or added in the amino acid sequence represented by SEQ ID NO: 5, as well as having cellobiohydrolase activity at least under conditions of a temperature of 75° C. and a pH of 5.5.

(I) A polypeptide including an amino acid sequence having 80% or greater but less than 100% sequence identity with the amino acid sequence represented by SEQ ID NO: 5, as well as having cellobiohydrolase activity at least under conditions of a temperature of 75° C. and a pH of 5.5.

(J) A polypeptide including the amino acid sequence represented by SEQ ID NO: 7.

(K) A polypeptide including an amino acid sequence in which one or several amino acids are deleted, substituted, or added in the amino acid sequence represented by SEQ ID NO: 7, as well as having cellobiohydrolase activity at least under conditions of a temperature of 75° C. and a pH of 5.5.

(L) A polypeptide including an amino acid sequence having 80% or greater but less than 100% sequence identity with the amino acid sequence represented by SEQ ID NO: 7, as well as having cellobiohydrolase activity at least under conditions of a temperature of 75° C. and a pH of 5.5.

In the present invention and the description of this application, a "polypeptide in which an amino acid is deleted" means that a portion of the amino acids which constitute the polypeptide is missing (removed).

In the present invention and the description of this application, a "polypeptide in which an amino acid is substituted" means that an amino acid which constitutes the polypeptide is replaced with a different amino acid.

In the present invention and the description of this application, a "polypeptide in which an amino acid is added" means that a new amino acid is inserted within the polypeptide.

In the above-mentioned polypeptides of (B), (E), (H), and (K), the number of amino acids to be deleted, substituted, or added in the amino acid sequence represented by the SEQ ID NO: 1, 3, 5, or 7 is preferably 1 to 20, more preferably 1 to 10, and yet more preferably 1 to 5. The position(s) of the amino acid(s) to be deleted, substituted, or added in each amino acid sequence is(are) not specifically limited, although it is preferable that the amino acid at position 299 is arginine.

In the above-mentioned polypeptides of (C), (F), (I), and (L), the sequence identity with the amino acid sequence represented by the SEQ ID NO: 1, 3, 5, or 7 is not specifically limited as long as it is 80% or greater but less than 100%, although it is preferable to be 85% or greater but less than 100%, more preferably 90% or greater but less than 100%, and yet more preferably 95% or greater.

Note that, the sequence identity (homology) between a pair of amino acid sequences is obtained such that: two amino acid sequences are juxtaposed while having gaps in some parts accounting for insertion and deletion so that the largest numbers of corresponding amino acids can be matched, and the sequence identity is deemed to be the proportion of the matched amino acids relative to the whole amino acid sequences excluding the gaps, in the resulting alignment. The sequence identity between a pair of amino acid sequences can be obtained by using a variety of homology search software publicly known in the art. The sequence identity value between amino acid sequences in the present invention is obtained by calculation on the basis of an alignment obtained from a publicly known homology search software BLASTP.

The above-mentioned polypeptides of (B), (C), (E), (F), (H), (I), (K), and (L) may be artificially designed, or may also be homologs of AR19G-166-QV and the like, or partial proteins thereof.

The above-mentioned polypeptides of (A) to (L) may be respectively synthesized in a chemical manner based on the amino acid sequence, or may also be produced by a protein expression system using the polynucleotide according to the second aspect of the present invention that will be described later. Moreover, the above-mentioned polypeptides of (B), (C), (E), (F), (H), (I), (K), and (L) can also be respectively synthesized artificially based on a polypeptide including the amino acid sequence represented by the SEQ ID NO: 1, 3, 5, or 7, by using a gene recombination technique to introduce amino acid mutation(s).

The above-mentioned polypeptides of (A) to (L) have cellobiohydrolase activities at least under conditions of a temperature of 75° C. and a pH of 5.5. For this reason, a thermostable cellobiohydrolase can be obtained by having any above-mentioned polypeptide of (A) to (L) as the cellobiohydrolase catalytic domain. Of these, a polypeptide of any one of (D) to (L) is preferably used as the cellobiohydrolase catalytic domain because they exhibit higher cellobiohydrolase activities even at a temperature of 70 to 100° C.

The thermostable cellobiohydrolase according to the present invention uses the phosphoric acid swollen Avicel (PSA) as a substrate. The thermostable cellobiohydrolase may also use another β glucan than PSA as a substrate. Such another β glucan can be exemplified by lichenan composed of β-1,3 and β-1,4 linkages, a crystalline cellulose such as Avicel, a bacterial crystalline cellulose (bacterial microcrystalline cellulose, BMCC) and a filter paper, carboxymethyl cellulose (carboxymethyl cellulose, CMC), a glucan composed of β-1,3 and β-1,6 linkages, a glucan composed of β-1,3 linkages, a glucan composed of β-1,6 linkages, xylan, and the like. The thermostable cellobiohydrolase according to the present invention preferably uses, in addition to PSA, at least either one of a glucan composed of β-1,3 and β-1,4 linkages and a crystalline cellulose as a substrate, and more preferably uses PSA, a glucan composed of β-1,3 and β-1,4 linkages, and a crystalline cellulose as substrates.

Although the optimum pH of the thermostable cellobiohydrolase according to the present invention varies depending on the reaction temperature, it is within a range from pH14.5 to 6.0. The thermostable cellobiohydrolase according to the present invention preferably exhibits cellobiohydrolase activity at least within a range from pH4.5 to 6.0, more preferably exhibits cellobiohydrolase activity within a range from pH4.0 to 6.5, and yet more preferably exhibits cellobiohydrolase activity within a range from pH3.5 to 7.0.

The thermostable cellobiohydrolase according to the present invention may also have another cellulose hydrolysis activity than cellobiohydrolase activity. Such another cellulose hydrolysis activity can be exemplified by endoglucanase activity, xylanase activity, β-glucosidase activity, or the like.

The thermostable cellobiohydrolase according to the present invention may be an enzyme solely consisting of a cellobiohydrolase catalytic domain which includes any above-mentioned polypeptide of (A) to (L), or may also include another domain. Such another domain can be exemplified by other domains of publicly known cellobiohydrolases, but for cellobiohydrolase catalytic domains. For example, the thermostable cellobiohydrolase according to the present invention also includes enzymes obtained by substituting a cellobiohydrolase catalytic domain in a publicly known cellobiohydrolase with the above-mentioned polypeptide of (A) to (L).

If the thermostable cellobiohydrolase according to the present invention includes another domain than the cellobiohydrolase catalytic domain, it is preferable to include a cellulose-binding module. The cellulose-binding module may be either on the upstream (N-end side) or the downstream (C-end side) of the cellobiohydrolase catalytic domain. In addition, the cellulose-binding module and the cellobiohydrolase catalytic domain may be directly linked, or linked via a linker domain of an appropriate length. The thermostable cellobiohydrolase according to the present invention is preferably such that the cellulose-binding module is present on the upstream or the downstream of the cellobiohydrolase catalytic domain via a linker domain, more preferably such that the cellulose-binding module is present on the upstream of the cellobiohydrolase catalytic domain via a linker domain.

The cellulose-binding module contained in the thermostable cellobiohydrolase according to the present invention may suffice if it is a domain having an ability to bind to cellulose, for example, a domain having an ability to bind to PSA or a crystalline Avicel. The amino acid sequence thereof is not particularly limited. As the cellulose-binding module, for example, a cellulose-binding module of an already known protein or appropriately modified product thereof may be used. In the present invention, the cellulose-binding module is preferably a polypeptide including 148 amino acids (T35-P182) from threonine (T) at position 35 to proline (P) at position 182 the amino acid sequence represented by SEQ ID NO: 11, or a polypeptide including an amino acid sequence in which one or several amino acids are deleted, substituted, or added in the polypeptide, as well as having an ability to bind to cellulose.

If the thermostable cellobiohydrolase according to the present invention has a cellobiohydrolase catalytic domain and a cellulose-binding module, it is preferable that these are linked via a linker sequence. The amino acid sequence, the length, and the like, of the linker sequence are not particularly limited. Such a linker sequence can be specifically exemplified by a polypeptide including 112 amino acids (S183-T294) from serine (S) at position 183 to threonine (T) at position 294 of the amino acid sequence represented by SEQ ID NO: 11, or a polypeptide including an amino acid sequence in which one or several amino acids are deleted, substituted, or added in the polypeptide.

Note that, the amino acid sequence represented by SEQ ID NO: 11 is the amino acid sequence of the polypeptide encoded by the open reading frame OJ1-1 obtained from the metagenome DNA of high temperature hot spring soils and the novel gene OJ1-1-11 obtained from the concerned ORF by PCR cloning, which will be described later in Example 1. The 148 amino acids (T35-P182) from threonine at position 35 to proline at position 182 of OJ1-1-11 is thought to be a cellulose-binding module CBM3, and the 112 amino acids (S183-T294) from serine at position 183 to threonine at position 294 is thought to be a linker sequence.

Besides, the thermostable cellobiohydrolase according to the present invention may also have a signal peptide enabling to transport it to a specific region to effect localization within a cell, or a signal peptide to effect extracellular secretion, at the N end or the C end. Such a signal peptide can be exemplified by an apoplastic transport signal peptide, an endoplasmic reticulum retention signal peptide, a nuclear transport signal peptide, a secretory signal peptide, and the like. By adding such a signal peptide to the N end or the C end, the thermostable cellobiohydrolase expressed in the transgenic plant can be localized in the apoplast, the intracellular endoplasmic reticulum, or the like, The apoplastic transport signal peptide is not particularly limited, as long as it is a peptide enabling to transport the polypeptide to apoplast, and a publicly known apoplastic transport signal peptide can be appropriately used. The apoplastic transport signal peptide can be exemplified by, for example, the signal peptide of potato protease inhibitor II (for example, see Wang et al., Transgenic Research, 2005, vol. 14, p 167-178), or the like. Moreover, the endoplasmic reticulum retention signal peptide is not particularly limited, as long as it is a peptide enabling to retain the polypeptide within the endoplasmic reticulum, and a publicly known endoplasmic reticulum retention signal peptide can be appropriately used. The endoplasmic reticulum retention signal peptide can be exemplified by, for example, a signal peptide including a HDEL amino acid sequence, or the like.

In addition, the thermostable cellobiohydrolase according to the present invention may also be added with, for example, various types of tags at the N end or the C end, so as to enable easy and convenient purification in a case of the production using an expression system. Regarding such a tag, it is possible to use a tag for usual use in the expression/purification of a recombinant protein, such as a His tag, a HA (hemagglutinin) tag, a Myc tag, and a Flag tag.

[Polynucleotide that Encodes Thermostable Cellobiohydrolase]

The polynucleotide serving as the second aspect of the present invention encodes the thermostable cellobiohydrolase serving as the first aspect of the present invention. The thermostable cellobiohydrolase can be generated by using the expression system of a host made by introducing an expression vector incorporated with the polynucleotide into the host.

Specifically, the polynucleotide serving as the second aspect of the present invention is a polynucleotide having a region that encodes a cellobiohydrolase catalytic domain which includes any one of the following nucleotide sequences (a) to (n).

(a) A nucleotide sequence that encodes a polypeptide including the amino acid sequence represented by SEQ ID NO: 1.

(b) A nucleotide sequence that encodes a polypeptide including an amino acid sequence in which one or several amino acids are deleted, substituted, or added in the amino acid sequence represented by SEQ ID NO: 1, as well as having cellobiohydrolase activity at least under conditions of a temperature of 75° C. and a pH of 5.5.

(c) A nucleotide sequence that encodes a polypeptide including an amino acid sequence having 80% or greater but less than 100% sequence identity with the amino acid sequence represented by SEQ ID NO: 1, as well as having cellobiohydrolase activity at least under conditions of a temperature of 75° C. and a pH of 5.5.

(d) A nucleotide sequence that encodes a polypeptide including the amino acid sequence represented by SEQ ID NO: 3.

(e) A nucleotide sequence that encodes a polypeptide including an amino acid sequence in which one or several amino acids are deleted, substituted, or added in the amino acid sequence represented by SEQ ID NO: 3, as well as having cellobiohydrolase activity at least under conditions of a temperature of 75° C. and a pH of 5.5.

(f) A nucleotide sequence that encodes a polypeptide including an amino acid sequence having 80% or greater but less than 100% sequence identity with the amino acid sequence represented by SEQ ID NO: 3, as well as having cellobiohydrolase activity at least under conditions of a temperature of 75° C. and a pH of 5.5.

(g) A nucleotide sequence that encodes a polypeptide including the amino acid sequence represented by SEQ ID NO: 5.

(h) A nucleotide sequence that encodes a polypeptide including an amino acid sequence in which one or several amino acids are deleted, substituted, or added in the amino acid sequence represented by SEQ ID NO: 5, as well as having cellobiohydrolase activity at least under conditions of a temperature of 75° C. and a pH of 5.5.

(i) A nucleotide sequence that encodes a polypeptide including an amino acid sequence having 80% or greater but less than 100% sequence identity with the amino acid sequence represented by SEQ ID NO: 5, as well as having cellobiohydrolase activity at least under conditions of a temperature of 75° C. and a pH of 5.5.

(j) A nucleotide sequence that encodes a polypeptide including the amino acid sequence represented by SEQ ID NO: 7.

(k) A nucleotide sequence that encodes a polypeptide including an amino acid sequence in which one or several amino acids are deleted, substituted, or added in the amino acid sequence represented by SEQ ID NO: 7, as well as having cellobiohydrolase activity at least under conditions of a temperature of 75° C. and a pH of 5.5.

(l) A nucleotide sequence that encodes a polypeptide including an amino acid sequence having 80% or greater but less than 100% sequence identity with the amino acid sequence represented by SEQ ID NO: 7, as well as having cellobiohydrolase activity at least under conditions of a temperature of 75° C. and a pH of 5.5.

(m) A nucleotide sequence having 80% or greater but less than 100% sequence identity with a nucleotide sequence represented by SEQ ID NO: 2, 4, 6, or 8, as well as encoding a polypeptide having cellobiohydrolase activity at least under conditions of a temperature of 75° C. and a pH of 5.5.

(n) A nucleotide sequence of a polynucleotide which hybridizes with a polynucleotide including a nucleotide sequence represented by SEQ ID NO: 2, 4, 6, or 8 under a stringent condition, as well as being a nucleotide sequence that encodes a polypeptide having cellobiohydrolase activity at least under conditions of a temperature of 75° C. and a pH1 of 5.5.

Note that, in the present invention and the description of this application, the term "under a stringent condition" can be exemplified by the method described in Molecular Cloning—A Laboratory Manual Third Edition (Sambrook et al., Cold Spring Harbor Laboratory Press). The example thereof includes a condition in which hybridization is performed by incubation in a hybridization buffer including 6×SSC (composition of 20×SSC: 3M sodium chloride, 0.3M citric acid solution, and pH7.0), 5×Denhardt's solution (composition of 100×Denhardt's solution: 2 mass % bovine serum albumin, 2 mass % ficoll, 2 mass % polyvinylpyrrolidone), 0.5 mass % SDS, 0.1 mg/mL salmon sperm DNA, and 50% formamide, at a temperature of 42 to 70° C. for several hours to overnight. The washing buffer for use in the washing after the incubation is preferably 1×SSC solution containing 0.1 mass % SDS, and more preferably 0.1×SSC solution containing 0.1 mass % SDS.

In the above-mentioned nucleotide sequences of (a) to (l), it is preferable to select a degenerate codon having high frequency of usage in the host. For example, the above-mentioned nucleotide sequence of (a) may be either the nucleotide sequence represented by SEQ ID NO: 2, or a nucleotide sequence altered to have a codon having high frequency of usage in the host without changing the amino acid sequence to be encoded by the nucleotide sequence represented by SEQ ID NO: 2. Similarly, the above-mentioned nucleotide sequences of (d), (g), and (j) may also be respectively either the nucleotide sequences represented by SEQ ID NO: 4, 6, and 8, or nucleotide sequences in which degenerate codons in these nucleotide sequences are altered to codons having high frequency of usage in the host. Note that, these codons can be altered by a publicly known gene recombination technique.

The polynucleotide including the nucleotide sequence represented by SEQ ID NO: 2, 4, 6, or 8 may be synthesized in a chemical manner based on the nucleotide sequence information, or may be obtained as a full length of a gene that encodes AR19G-166-RA, AR19G-166-QV and the like (may be referred to as "AR19G-166 gene") or a partial region thereof including the cellobiohydrolase catalytic domain from the natural world by using a gene recombination technique. The full length of the AR19G-166 gene or the partial region thereof can be obtained by, for example, collecting a microbe-containing sample from the natural world, and conducting PCR using the genome DNA recovered from the sample as a template, with a forward primer and a reverse primer designed on the basis of the nucleotide sequence represented by SEQ ID NO: 2, 4, 6, or 8 by a usual method. The cDNA synthesized by a reverse transcription reaction using mRNA recovered from the sample as a template may also be used as a template. Note that, it is preferable that the sample for recovering the nucleic acid serving as a template is a sample collected from a high temperature environment such as hot spring soil.

In the above-mentioned nucleotide sequence of (m), the sequence identity with the nucleotide sequence represented by SEQ ID NO: 2, 4, 6, or 8 is not particularly limited as long as it is 80% or greater but less than 100%, although it is preferable to be 85% or greater but less than 100%, more preferably 90% or greater but less than 100%, and yet more preferably 95% or greater but less than 100%.

Note that, the sequence identity (homology) between a pair of nucleotide sequences is obtained such that: two nucleotide sequences are juxtaposed while having gaps in some parts accounting for insertion and deletion so that the largest numbers of corresponding nucleotides can be matched, and the sequence identity is deemed to be the proportion of the matched nucleotides relative to the whole nucleotide sequences excluding gaps, in the resulting alignment. The sequence identity between a pair of nucleotide sequences can be obtained by using a variety of homology search software publicly known in the art. The sequence identity value between nucleotide sequences in the present invention is obtained by calculation on the basis of an alignment obtained from a publicly known homology search software BLASTN.

For example, the polynucleotide including the above-mentioned nucleotide sequence of (b), (c), (e), (f), (h), (i), (k), (l), or (m) can be respectively synthesized artificially by deleting, substituting, or adding one or a plurality of nucleotides in a polynucleotide including the nucleotide sequence represented by SEQ ID) NO: 2, 4, 6, or 8. Moreover, the above-mentioned nucleotide sequence of (b), (c), (e), (f), (h), (i), (k), or (l) may also be a full length sequence of a homologous gene of the AR19G-166 gene or a partial sequence thereof. The homologous gene of the AR19G-166 gene can be obtained by a gene recombination technique for use in obtaining a homologous gene of a gene whose nucleotide sequence has been already known.

In the present invention and the description of this application, a "polynucleotide in which a nucleotide is deleted" means that a portion of the nucleotides which constitute the polynucleotide is missing (removed).

In the present invention and the description of this application, a "polynucleotide in which a nucleotide is substituted" means that a nucleotide which constitutes the polynucleotide is replaced with a different nucleotide.

In the present invention and the description of this application, a "polynucleotide in which nucleotide is added" means that a new nucleotide is inserted within the polynucleotide.

When a polynucleotide including a nucleotide sequence of the aforementioned (b). (c), (e), (f), (h), (i), (k), (l) or (m) is synthesized artificially, there is no particular limitation on the number of nucleotides to be deleted, substituted or added in the amino nucleotide sequence represented by SEQ ID) NO: 2, 4, 6 or 8, provided that the nucleotide sequence of the polynucleotide following the synthesis has 80% or greater but less than 100% sequence identity with the nucleotide sequence represented by SEQ ID NO: 2, 4, 6 or 8, but the number of nucleotides is preferably from 1 to 256, more preferably from 1 to 192, still more preferably from 1 to 128, and particularly preferably from 1 to 64.

The polynucleotide serving as the second aspect of the present invention may have only the region that encodes the cellobiohydrolase catalytic domain, or may also have a region that encodes a cellulose-binding module, a linker sequence, various types of signal peptides, various types of tags, or the like, in addition to the region.

[Expression Vector]

The expression vector serving as the third aspect of the present invention is incorporated with the above-mentioned polynucleotide of the second aspect of the present invention, and is able to express a polypeptide having cellobiohydrolase activity at least under conditions of a temperature of 75° C. and a pH of 5.5 in a host cell. That is, it is an expression vector which is incorporated with the above-mentioned polynucleotide of the second aspect of the present invention in a state where the above-mentioned thermostable cellobiohydrolase of the first aspect of the present invention can be expressed.

In the present invention and the description of this application, an "expression vector" is a vector including, from upstream, DNA having a promoter sequence, DNA having a sequence for incorporating foreign DNA, and DNA having a terminator sequence.

Specifically, it is necessary for the expression vector to be incorporated with, as an expression cassette including, from the upstream, DNA having a promoter sequence, the above-mentioned polynucleotide of the second aspect of the present invention, and DNA having a terminator sequence. Note that, the incorporation of the polynucleotide into the expression vector can also be performed by using a well-known gene recombination technique, or may also be done by using a commercially available expression vector production kit.

The expression vector may be a vector to be introduced into a prokaryotic cell such as *E. coli* or actinobacteria, or to be introduced into a eukaryotic cell such as a yeast, a filamentous fungus, an insect cultured cell, a mammalian cultured cell, or a plant cell. Regarding such an expression vector, an arbitrary expression vector for usual use can be adopted corresponding to the respective host.

The expression vector to be introduced into plant cells can be exemplified by binary vectors such as pIG121 or pIG121Hm. The usable promoter can be exemplified by nopaline synthase promoter, cauliflower mosaic virus 35S promoter, or the like. Moreover, the usable terminator can be exemplified by nopaline synthase terminator, or the like. Besides, a tissue- or organ-specific promoter may also be used. With use of such a tissue- or organ-specific promoter, the thermostable cellobiohydrolase can be expressed not in the entire plant but in the specific tissue or organ only. Thus, for example, it can be expected to be possible to express the thermostable cellobiohydrolase only in inedible parts of an edible plant.

It is preferable that the expression vector according to the present invention is an expression vector incorporated with not only the above-mentioned polynucleotide of the second aspect of the present invention but also a drug resistance gene or the like. This is because it makes it easy to screen plants transformed by the expression vector and untransformed plants. The drug resistance gene can be exemplified by a kanamycin resistance gene, a hygromycin resistance gene, a bialaphos resistance gene, or the like.

[Transformant]

The transformant serving as the fourth aspect of the present invention is introduced with the above-mentioned expression vector of the third aspect of the present invention.

In the transformant, the above-mentioned thermostable cellobiohydrolase of the first aspect of the present invention can be expressed. Many so far known cellobiohydrolases have a narrow range of expression hosts, in other words, it is hard to express many so far known cellobiohydrolases in different species. On the other hand, the thermostable cellobiohydrolase according to the present invention can be expressed in a wide range of expression hosts such as *E. coli*, actinobacteria, yeast, filamentous fungi, or higher plant chloroplasts.

The method to produce the transformant using the expression vector is not particularly limited, and a method for usual use in the production of transformants can be conducted. The concerned method can be exemplified by an *Agrobacterium* method, a particle gun method, an electroporation method, a PEG (polyethylene glycol) method, and the like. Of these, if the host is a plant cell, a particle gun method or an *Agrobacterium* method is preferred.

The host to introduce the expression vector may be a prokaryotic cell such as *E. coli* or an actinobacterium or a eukaryotic cell such as a yeast, a filamentous fungus, an insect cultured cell, a mammalian cultured cell, or a plant cell. By culturing a transformant of *E. coli* or actinobacteria, the thermostable cellobiohydrolase according to the present invention can be produced more easily and conveniently with high yield. On the other hand, because proteins are glycosylated in eukaryotic cells, a thermostable cellobiohydrolase which is more thermostable can be produced by using a transformant of a eukaryotic cell rather than by using a transformant of a prokaryotic cell. In particular, if the concerned transformant is a filamentous fungus such as *Aspergillus* or a eukaryotic microbe (or eukaryote) such as yeast, a thermostable cellobiohydrolase which is more thermostable can be produced relatively easily and conveniently with high yield. Moreover, the transgenic plant introduced with the above-mentioned expression vector of the third aspect of the present invention enables large-scale cultivation by means of outdoor cultivation or the like as well as achieving a relatively large production amount of the thermostable cellobiohydrolase according to the present invention per one plant. Furthermore, because the transgenic plant originally contains thermostable cellobiohydrolase inside the plant body, it is suitable as a biomass resource.

The host cell used for expressing the thermostable cellobiohydrolase according to the present invention is preferably at least one host cell selected from the group consisting of *E. coli*, yeast, filamentous fungi, actinobacteria and plants, is more preferably at least one host cell selected from the group consisting of yeast, filamentous fungi, actinobacteria and plants, and is still more preferably a plant.

If a prokaryotic cell, a yeast, a filamentous fungus, an insect cultured cell, or a mammalian cultured cell is used as a host, the obtained transformant is generally able to be cultured by a usual method in the same manner as that of the untransformed host.

If the transformant according to the present invention is a plant, a plant cultured cell, a plant organ, or a plant tissue may be used as a host. By using a well-known plant tissue culture method or the like, the transgenic plant can be obtained from the transformed plant cells, callus, or the like. For example, the transgenic plant can be obtained by culturing the transformed plant cell using a hormone free redifferentiation medium or the like, transplanting the thus obtained rooted juvenile plant into soil or the like, and cultivating the same.

If the transformant according to the present invention is a plant, the expression cassette for expressing the thermostable cellobiohydrolase according to the present invention derived from the above-mentioned expression vector of the third aspect of the present invention may be incorporated in the nuclear genome of the plant, although it is preferably incorporated in the chloroplast genome. In the chloroplast transformant, the inserted foreign gene is cytoplasmically inherited. Therefore, the leaking of the recombinant gene to the environment through the pollen can be prevented. In the large-scale production by means of outdoor cultivation of the transgenic plant, the leaking of the recombinant gene to the environment is a concern. However, the chloroplast transformant is more advantageous than the nuclear genome transformant in the point of the prevention of leaking of the recombinant gene to the environment.

In addition, if the transformant according to the present invention is a plant, the transformant also includes, in addition to the plant directly obtained from the transformation, a plant which is a progeny of the pertinent plant and which is expressing the thermostable cellobiohydrolase according to the present invention in the same manner as that of the pertinent plant. Here, the term "progeny of a plant" means a plant obtained from germinating a seed from the pertinent plant, a plant obtained from a cutting thereof, or the like.

The type of the plant to be used as a host is not particularly limited, and it may be dicot or monocot, fern or moss, or alga or microalga. For example, plants belonging to the Brassicaceae family, the Poaceae family, the Solanaceae family, the Fabaceae family, the Asteraceae family, the Convolvulaceae family, the Euphorbiaceae family, and the like can be enumerated. Plants belonging to the Solanaceae family, the Brassicaceae family, or the Poaceae family is preferred because they are suitable plants for the transformation via *Agrobacterium*. Plants belonging to the Solanaceae family include, for example, tobacco, eggplant, potato, tomato, bell pepper, and the like. Plants belonging to the Brassicaceae family include, for example, *Arabidopsis thaliana*, brassica, shepherd's-purse, radish, cabbage, wasabi, and the like. Moreover, plants belonging to the Poaceae family include, for example, rice, corn, sorghum, wheat, barley, rye, millet, and the like. In addition, plants belonging to the Fabaceae family include, for example, peanut, chickpea, soybean, frijol, and the like. Plants belonging to the Asteraceae family include, for example, burdock, wormwood, marigold, cornflower, sunflower, and the like. Plants belonging to the Convolvulaceae family include, for example, bellbind, sea bells, the genus *Cuscuta*, field bindweed, and the like. Plants belonging to the Euphorbiaceae family include, for example, wartweed, *E. sieboldiana, E. lasiocaula*, and the like.

When the transformant according to the present invention is a plant, among the various plants, a monocot is preferable, a plant of the Poaceae family is more preferable, and a plant of the Poaceae family having a large amount of biomass is even more preferable.

[Method for Producing a Thermostable Cellobiohydrolase]

The method for producing a thermostable cellobiohydrolase serving as the fifth aspect of the present invention is a method to generate a thermostable cellobiohydrolase in the above-mentioned transformant of the fourth aspect of the present invention. In the transformant produced by using the expression vector incorporated with the above-mentioned polynucleotide of the second aspect of the present invention on the downstream of a promoter which has no ability to regulate the timing of the expression or the like, the thermostable cellobiohydrolase according to the present invention is constantly expressed. On the other hand, for the transformant produced by using a so-called expression inducible promoter to induce the expression by means of a specific compound, temperature condition, or the like, the thermostable cellobiohydrolase is expressed in the concerned transformant by conducting an induction treatment suitable for the respective expression-inducing condition.

The thermostable cellobiohydrolase generated by the transformant may be used in a state of being retained in the transformant, or may be extracted/purified from the transformant.

The method to extract/purify the thermostable cellobiohydrolase from the transformant is not particularly limited as long as the method does not deteriorate the activity of the thermostable cellobiohydrolase, and the extraction can be done by a method for usual use in the extraction of a polypeptide from cells or biological tissue. The method can be exemplified by a method in which the transformant is immersed in an appropriate extraction buffer to extract the thermostable cellobiohydrolase, and thereafter the liquid extract and the solid residue are separated. The extraction buffer preferably contains a solubilizing agent such as a surfactant. If the transformant is a plant, the transformant may be previously shredded or crushed before immersing in an extraction buffer. Moreover, as the method for separating the liquid extract and the solid residue, for example, a publicly known solid-liquid separation treatment such as a filtration method, a compression filtration method, or a centrifugation treatment method may be used, or the transformant immersed in an extraction buffer may be squeezed. The thermostable cellobiohydrolase in the liquid extract can be purified by using a publicly known purification method such as a salting-out method, an ultrafiltration method, or a chromatography method.

If the thermostable cellobiohydrolase according to the present invention is expressed while the secretory signal peptide is held in the transformant, a solution containing the thermostable cellobiohydrolase can be easily and conveniently obtained by culturing the transformant and thereafter recovering a culture liquid supernatant made by removal of the transformant from the obtained culture product. Moreover, if the thermostable cellobiohydrolase according to the present invention has a tag such as a His tag, the thermostable cellobiohydrolase in a liquid extract or in a culture supernatant can be easily and conveniently purified by an affinity chromatography method using the tag.

In other words, the method for producing a thermostable cellobiohydrolase according to the present invention includes the expression of a thermostable cellobiohydrolase within the transformant of the fourth aspect of the present invention, and, according to need, the extraction and purification of the thermostable cellobiohydrolase from the transformant.

[Cellulase Mixture]

The cellulase mixture serving as the sixth aspect of the present invention includes the above-mentioned thermostable cellobiohydrolase of the first aspect of the present invention, or a thermostable cellobiohydrolase produced by the above-mentioned method for producing a thermostable cellobiohydrolase of the fifth aspect, and at least one or more types of other cellulases. The thermostable cellobiohydrolase produced by the above-mentioned method for producing a thermostable cellobiohydrolase of the fifth aspect may be in a state of being included in the transformant, or may be extracted/purified from the transformant. By using the thermostable cellobiohydrolase according to the present invention as a mixture with other cellulases in the reaction to degrade cellulose, persistent lignocelluloses can be more efficiently degraded.

The other cellulase than the above-mentioned thermostable cellobiohydrolase to be contained in the cellulase mixture is not particularly limited as long as it has cellulose hydrolysis activity. For example, the cellulase can be exemplified by xylanase, β-xylosidase, or such a hemicellulose, β-glucosidase, endoglucanase, or the like. The cellulase mixture according to the present invention preferably contains at least either one of a hemicellulase and an endoglucanase, and more preferably contains both a hemicellulase and an endoglucanase. In particular, it is preferable to contain one or more types of cellulases selected from the group consisting of xylanase, β-xylosidase, β-glucosidase, and endoglucanase, and it is more preferable to contain all of xylanase, β-xylosidase, β-glucosidase, and endoglucanase.

The other cellulose to be contained in the cellulase mixture is preferably a thermostable cellulose having cellulase activity at least at a temperature of 70° C., and more preferably a thermostable cellulose having cellulase activity at a temperature of 70 to 90° C. When all the enzymes contained in the cellulase mixture are thermostable, the reaction to degrade celluloses with the cellulase mixture can be efficiently conducted under a high temperature condition. That is, if the cellulase mixture contains only thermostable cellulases, it becomes possible, by using the cellulase mixture for a lignocellulose hydrolysis treatment, to conduct the lignocellulose hydrolysis reaction under a high temperature environment where the hydrolysis temperature is from 70 to 90° C. With this high temperature hydrolysis, the amount of enzymes and the time for hydrolysis can be remarkably reduced, and the cost for hydrolysis can be largely cut out.

[Method for Producing a Cellulose Degradation Product]

The method for producing a cellulose degradation product serving as the seventh aspect of the present invention is a method to obtain a degradation product by degrading cellulose with the thermostable cellobiohydrolase according to the present invention. Specifically, a cellulose degradation product is generated by contacting a cellulose-containing material to the above-mentioned thermostable cellobiohydrolase of the first aspect of the present invention, the above-mentioned transformant of the fourth aspect of the present invention, or a thermostable cellobiohydrolase produced by the above-mentioned method for producing a thermostable cellobiohydrolase of the fifth aspect.

In the present invention and the description of this application, the term "cellulose degradation product" includes cellobiose.

The cellulose-containing material is not particularly limited as long as it contains cellulose. Such a material can be exemplified by a weed, an agricultural waste, or such a cellulosic biomass, used paper, and the like. The cellulose-containing material is preferably subjected to a mechanical treatment such as crushing or shredding, a chemical treatment with acid, alkali or the like, a treatment such as immersing in an appropriate buffer or a dissolution treatment, or the like, before contacting to the thermostable cellobiohydrolase according to the present invention.

The reaction condition of the cellulose hydrolysis reaction by means of the thermostable cellobiohydrolase according to the present invention may suffice if the condition allows the thermostable cellobiohydrolase to exhibit cellobiohydrolase activity. For example, it is preferable to conduct the reaction at a temperature of 55 to 80° C. and a pH of 3.5 to 7.0, and more preferable to conduct the reaction at a temperature of 70 to 100° C. and a pH of 4.0 to 6.0. The reaction time is appropriately adjusted by considering the type, the pretreatment method, the amount, and the like, of the cellulose-containing material to be supplied to the hydrolysis. For example, the reaction time can be 10 minutes to 100 hours if a cellulosic biomass is degraded for 1 to 100 hours.

In the cellulose hydrolysis reaction, it is also preferable to use at least one or more types of other cellulases, in addition to the thermostable cellobiohydrolase according to the present invention. The other cellulase may be the same as the cellulase that can be contained in the above-mentioned cellulase mixture, and it is preferable to be a thermostable cellulase having cellulase activity at least at a temperature of 70° C., and preferably at least at a temperature of 70 to 100° C. In addition, in the method for producing a cellulose degradation product, it is also possible to use the above-mentioned cellulase mixture of the sixth aspect of the present invention instead of, the above-mentioned thermostable cellobiohydrolase of the first aspect of the present invention, the above-mentioned transformant of the fourth aspect of the present invention, or a thermostable cellobiohydrolase produced by the above-mentioned method for producing a thermostable cellobiohydrolase of the fifth aspect.

[Method for Producing a Polynucleotide and Primers for Use Therein]

The method for producing a polynucleotide that encodes a thermostable cellobiohydrolase serving as the eighth aspect of the present invention is a method, including conducting PCR using DNA derived from a biological organism or a reverse transcription product of RNA derived from a biological organism as a template, with a forward primer including the nucleotide sequence represented by SEQ ID NO: 12 or a nucleotide sequence in which one or several nucleotides are added to the 5' end of the nucleotide sequence represented by SEQ ID NO: 12 (a primer serving as the ninth aspect of the present invention), and a reverse primer including the nucleotide sequence represented by SEQ ID NO: 13 or a nucleotide sequence in which one or several nucleotides are added to the 5 end of the nucleotide sequence represented by SEQ ID NO: 13 (a primer serving as the tenth aspect of the present invention), and obtaining a polynucleotide including a nucleotide sequence that encodes a thermostable cellobiohydrolase as an amplification product.

The nucleotide sequence represented by SEQ ID NO: 12 is a nucleotide sequence which is homologous (identical) with a partial sequence including the nucleotides at position 1 to 22 of the nucleotide sequence represented by SEQ ID NO: 2. Moreover, the nucleotide sequence represented by SEQ ID NO: 13 is a nucleotide sequence which is complementary with a partial sequence including the nucleotides at position 1263 to 1284 of the nucleotide sequence represented by SEQ ID NO: 2. For this reason, a polynucleotide that encodes the cellobiohydrolase catalytic domain of the AR19G-166 gene (for example, a polynucleotide including a nucleotide sequence represented by SEQ ID NO: 2, 4, 6, or 8) can be obtained as an amplification product, by conducting PCR with a primer including the nucleotide sequence represented by SEQ ID NO: 12 as a forward primer and a primer including the nucleotide sequence represented by SEQ ID NO: 13 as a reverse primer, using a polynucleotide including the nucleotide sequence represented by SEQ ID NO: 2 as a template.

In PCR, the 5'-end side of the primer may also have an additive nucleotide sequence which is not to be supplied to the hybridization with the template. For example, by using a forward primer including a nucleotide sequence in which one or several nucleotides are added to the 5' end of the nucleotide sequence represented by SEQ ID NO: 12 and a reverse primer including a nucleotide sequence in which one or several nucleotides are added to the 5' end of the nucleotide sequence represented by SEQ ID NO: 13, a polynucleotide in which one or several nucleotides derived from the forward primer are added to the 5' end of the region that encodes the cellobiohydrolase catalytic domain of the AR19G-166 gene and one or several nucleotides derived from the reverse primer are added to the 3' end thereof can be obtained. The nucleotide sequence to be added to the 5' end of each primer can be exemplified by a sequence that is required for incorporating the amplification product to the expression vector, a restriction enzyme site, a nucleotide sequence that encodes a tag, a nucleotide sequence that encodes a signal peptide, or the like. In addition, it is also preferable to add an initiating methionine (ATG) to the 5' end of the nucleotide sequence represented by SEQ ID NO: 12.

The DNA used as a template of PCR is DNA derived from a biological organism or a reverse transcription product (cDNA) of RNA derived from a biological organism. The biological organism may be a microorganism artificially introduced with a plasmid in which a polynucleotide encoding the cellobiohydrolase catalytic domain of the AR19G-166 gene has been incorporated, the above-mentioned transformant, or a biological organism contained in a sample collected from the natural world. In a case where the DNA serving as a template is prepared from a sample collected from the natural world, the sample is preferably collected from a high temperature environment such as hot spring soil.

In the method for producing a polynucleotide according to the present invention, the PCR condition and the like can be appropriately determined with consideration of the type of the polymerase to be used and the like by a person skilled in the art. In a case where the genome DNA of the AR19G-166 gene or cDNA synthesized from mRNA of the gene is contained in the nucleic acid used as a template, a polynucleotide that encodes the cellobiohydrolase catalytic domain of the AR19G-166 gene can be obtained as an amplification product from the PCR.

The amino acid sequence of the cellobiohydrolase catalytic domain is highly conservative between homologous genes. For this reason, in a case where the genome DNA of a homologous gene of the AR19G-166 gene or cDNA synthesized from mRNA of the homologous gene is contained in the nucleic acid used as a template, a polynucleotide that encodes the cellobiohydrolase catalytic domain of the homologous gene of the AR19G-166 gene can be obtained as an amplification product by using the above-mentioned forward primer and the above-mentioned reverse primer with the method for producing a polynucleotide according to the present invention.

In addition, in a case where the genome DNA of a gene which is not a homologous gene of the AR19G-166 gene but has a similar nucleotide sequence to that of the AR19G-166 gene, or cDNA synthesized from mRNA of the homologous gene is contained in the nucleic acid used as a template, a polynucleotide that encodes the whole region or a partial region of the pertinent gene can be obtained as an amplification product with the method for producing a polynucleotide according to the present invention. For this reason, the method for producing a polynucleotide according to the present invention is also useful for cloning a novel cellobiohydrolase including a similar amino acid sequence to that of the AR19G-166 gene.

EXAMPLES

Next is a more detailed description of the present invention with reference to Examples. However, the present invention is not to be limited to the following Examples.

Example 1

Cloning of Novel Thermostable Cellobiohydrolase from Hot Spring Soil

<1> DNA Extraction from Hot Spring Soil and Whole Genome Sequencing (WGS)

With the purpose of searching for genes of thermostable cellobiohydrolase (optimum temperature: 55° C. or higher) and super thermostable cellobiohydrolase (optimum temperature: 80° C. or higher), soil DNA was collected from neutral-to-faintly alkaline hot springs and subjected to nucleotide sequencing of the metagenome DNA of the microbiota constituting the soil.

As the soil sample from neutral-to-faintly alkaline hot springs, hot spring water containing soil, clay, and biomat was collected from five sampling points having gushing high temperature outdoor hot springs in three areas in Japan (metagenome DNA samples N2, AR19, AR15, OJ1, and H1). These hot spring soil samples were within a range of temperature from 58 to 78° C. and a pH of 7.2 to 8 at the time of the collection.

DNA was extracted from 10 g each of the collected hot spring soil samples by using the DNA extraction kit (ISOIL Large for Beads ver. 2, manufactured by NIPPON GENE). 5 μg of each genome sample yielding a DNA amount of 10 μg or more was subjected to metagenome sequencing. That is, the extracted DNA was subjected to shotgun sequencing of the metagenome DNA and 16S rDNA amplicon by using the GS FLX Titanium 454 manufactured by Roche Diagnostics. The remaining DNA was used for PCR cloning of the cellulase gene. On the other hand, samples yielding small (10 μg or smaller) DNA amounts were subjected to genomic amplification using the genome DNA amplification kit (GenomiPhi V2 DNA Amplification Kit, manufactured by GE Healthcare), and the resultant amplification product was subjected to the metagenome DNA sequencing.

The metagenome DNA sequencing was carried out three to four times per each hot spring soil sample, meaning 19 times in total. By so doing, a data set of the whole genome sequence (WGS) with an average read length of 394 bp, a total number of reads of 26,295,463, and a total quantity of sequenced genomes of 10.3 Gbp, was obtained.

<2> Assembling and Statistics of Hot Spring Metagenome Data

The sequence library was constructed using the genome DNA extracted from the hot spring metagenome in accordance with the standard protocol for Roche 454 GS FLX Titanium technology for shotgun sequencing. The output from the Roche 454 (sff file) was rebasecalled with the PyroBayes (Quinlan et al., Nature Methods, 2008, vol. 5, p. 179-81.), by which sequence files and quality files in FASTA format were obtained. After clipping their ends to improve the quality, the obtained sequence reads were assembled with use of the assembly software, Newbler version 2.3 or 2.5.3 of 454 Life Sciences. The assembling was performed by setting "minimum acceptable overlap match (mi)=0.9", and "option:—large (for large or complex genomes, speeds up assembly, but reduces accuracy.)".

The total of the quality filter processed reads and 100 bp or longer assemble contigs was 2.5 Gbp. This data set was used for the cellulase enzyme gene analysis. Out of the total read number of 26,294,193 reads, 17,991,567 reads were assembled into 1 kb or longer contigs in average (595,602 contigs in total). Of these, the longest contig length was 278,185 bp.

The assembled sequences were referred to the KEGG database (Kanehisa, M. Science &

Technology Japan, 1996, No.59, p.34-38, by which all the contigs and singletons were phylogenetically classified into five categories of bacteria, archaea (ancient bacteria), eukaryotes, virus, and those outside any of these. Among 2.5 Gbp of the length of the assembled sequences (=total contig length +total singleton length), the length of the sequences hit to bacteria was 258 Mbp, the length of the sequences hit to archaea was 27 Mbp, the length of the sequences hit to eukaryotes was 193,561 bp (0.008% of the total length of the assembled sequences), and the length of the sequences hit to virus was 685,640 bp (0.027% of the total length of the assembled sequences). The reason why the sequences belonging to eukaryotes were not abundant was thought to reflect the condition in which the temperature of the hot spring soil metagenome was in a range from 58 to 70° C., which was over the temperature limit of living for eukaryotes such as filamentous fungi. From these results, this metagenome database was found to contain no more than 11.3% of the already-known DNA sequences. The length of the sequences of those outside any of these categories was 2.2 Gbp, which accounted for 88.7% of the total of the assembled sequences. These are novel sequences derived from any one of bacteria, archaea, or eukaryotes. This result supports the indication of Handelsman et al. (Handelsman et al., Chem Biol., 1998, vol.5, p.R245-R249) that most of the genome DNA constituting the microbial communities of some specific environments have not been comprehended by the conventional approach of microbial genome researches, that is, a method of culturing and isolating a microorganism and thereafter conducting Sanger sequencing of the whole genome DNA to describe the genome.

<3>Prediction of open reading frames (ORFs) of cellobiohydrolase

The sequences of EC numbers of 3.2.1.4 (cellulose), 3.2.1.37 (β-xylosidase), 3.2.1.91 (cellulose 1,4-β-cellobiosidase), and 3.2.1.8 (endo 1,4-β-xylanase) were downloaded from the UniProtdatabase, and the proteome local database of these glycoside hydrolase genes was constructed. Using the annotation software Orphelia (Hoff et al., Nucleic Acids Research, 2009, 37 (Web Server issue: W101-W105) for the metagenomes AR15 and AR19, and the Metagene (Noguchi et al., DNA Research, 2008, 15(6)) for the metagenomes H1, N2, and OJ1, gene regions (=open reading frames) were predicted from the contig sequences obtained from the above-mentioned process <2>(Orphelia option: default (model =Net700, maxoverlap =60), Metagene option: -m). In order to extract the glycoside hydrolase gene from the predicted ORF, the local database using BLASTP (blastall ver. 2.2.18) was referred to. The optimum condition of BLASTP was set such that: "Filter query sequence =false", "Expectation value (E) <1e$^{-20}$"(hereunder, the defalt values: Cost to open a gap =-1, Cost to extended gap =-1, X dropoff value for gapped alignment =0, Threshold for extending hits =0, and Word size =default), and the hit sequences were collected as glycoside hydrolase genes.

The annotation software Orphelia and the Metagene do not address the frameshift caused by reading error or the like. Thus, the frameshift correction was conducted by the following manner. First, contigs were cut in 2 kbp length by shifting by 1 kbp. For this reason, the cut sequences were overlapped with the forward and following sequences by 1 kbp. The respective cut contig sequences were referred to the above-mentioned proteome local database of the glycoside hydrolase genes (E<1e$^{-20}$) to be subjected to screening by Blastx. For the hit contig sequences, the coding region of glycoside hydrolase was acquired by using the Genewise (Wise2 package. At this time, sequences having 100 bp or shorter coding region were eliminated. With the Genewise software, the frameshift correction of sequences is conducted by referring to enzyme sequences hit to the target contig in the local databases, and inserting or deleting gaps so as to achieve the maximum alignment score.

The thus obtained glycoside hydrolases such as cellulose, endo hemicellulose, or debranching enzyme were subjected to function classification, with reference to the protein functional region sequence database of pfam HMMs (Pfam version 23.0 and HMMER v 2.3; Finn et al., Nucleic Acids Research Database, 2010, Vol. 38, p.D211-222). Specifically, their glycoside hydrolase (GH) families were determined by the homology with the Pfam region database by using the sequence homology search algorithm HMMER to which the hidden Markov model was applied (Durbin et al., "The theory behind profile HMMs. Biological sequence analysis: probabilistic models of proteins and nucleic acids", 1998, Cambridge University Press; hmmpfam (Ver. 2.3.2), E-value cutoff <1e$^{-5}$; Database=Pfam_fs (models that can be used to find fragments of the represented domains in a sequence.)). BLASTP screening was carried out and 44 ORFs hit as the CBH (cellobiohydrolase) sequence were classified in GH families.

<4> Correction of Rare Initiation Codon Found in Orphelia Output

The annotation software Orphelia detects ORFs having not only ATG (methionine), but also rare codons of GTG (valine), TTG (leucine), and ATA (isoleucine), as the initiation codon. For this reason, in cases where the assembled contigs do not include a full-length ORF having ATG as the initiation codon, an error may occur in which the Orphelia recognizes such a rare codon as the initiation codon. In the above-mentioned process <3>, there were eight ORFs having these rare codons of GTG, TTG, and ATA as the initiation codon, among the ORF outputs determined to have full-length from the Orphelia. With reference to the amino acid sequences of the ORF outputs from the genewise and the ORF-including contigs, these ORFs were checked whether these were full-length sequences having such rare codons as the initiation codon or output errors. As a result, it was revealed that these eight ORFs output from the Orphelia having these rare codons as the initiation codon were all output errors, in other words, no-full-length sequences.

TABLE 1

| | GH family classification of cellobiohydrolase genes | | | | | |
|---|---|---|---|---|---|---|
| Metagenome | GH6 | GH7 | GH9 | GH48 | Other GHs | Total |
| AR19 | 2(0) | 0 | 2(2) | 5(1) | 4(3) | 13(6) |
| AR15 | 0 | 0 | 1(1) | 2(1) | 3(2) | 6(4) |
| OJ1 | 2(0) | 0 | 7(2) | 2(1) | 4(2) | 15(5) |
| N2 | 0 | 0 | 5(3) | 3(0) | 2(2) | 10(5) |
| H1 | 0 | 0 | 0 | 0 | 0 | 0 |
| Total number of ORFs | 4(0) | 0(0) | 15(8) | 12(3) | 13(9) | 44(20) |

The result of the GH family classification of 44 ORFs predicted as cellobiohydrolase genes is shown in Table 1. In Table 1, the number in the brackets shows the number of full-length ORFs having methionine as the initiation codon. As shown in Table 1, two cellobiohydrolase ORFs (AR19G-166 and AR19G-12) belonging to the GH6 family were obtained from the metagenome AR19, and two cellobiohydrolase ORFs (OJ1-1 and OJ1-2) belonging to the same were obtained from the metagenome OJ1, meaning four ORFs in total. On the other hand, no ORF sequence belonging to the GH7 family was obtained. 15 ORFs belonging to the GH9 family, and 12 ORFs belonging to the GH48 Family were obtained. 13 cellobiohydrolase gene ORFs belonging to the other GH families (GH10, GH12, and GH26) were obtained in total. Primers were designed for all of these ORFs having been predicted as cellobiohydrolase genes, including no-full-length sequences, and these genes were cloned from the hot spring soil metagenome DNA by PCR.

Note that, cellulase enzyme liquids for biofuel now available for practical use are Novozyme CELLIC (registered trademark) CTec2, and Genencor Accellerase (registered trademark) TRIO, which are all based on enzymes secreted by a wood-decay fungus *Trichoderma reesei*. The main components of the glycoside hydrolases (GH) secreted from this filamentous fungus are cellobiohydrolases CBHI and CBHII, which respectively belong to the GH7 family and the GH6 family.

<5> Open Reading Frames OJ1-1 and OJ1-2

The open reading frame OJ1-1 included 548 amino acids, and encoded a multi-domain enzyme having a cellulose-binding module CBM3 (149 bp)-linker (111 bp)-GH6 catalytic domain. However, the latter half of the catalytic domain lacked the termination codon and was not in full-length. Moreover, this cellulose-binding module sequence is a novel CBM3 sequence showing 63% amino acid sequence identity with the cellulose-binding module CBM3 (SEQ ID NO: 16) of a cellobiohydrolase of a thermophilic aerobic bacterium *Caldibacillus cellulovorans* (Genbank: AAF22273.1). The cellobiohydrolase catalytic domain of OJ1-1 showed 58% amino acid sequence identity with a cellulose 1,4-β-cellobiosidase of *Amycolatopsis mediterranei* U32 (Genbank: ADJ46954.1), and showed 48% amino acid sequence identity with a β-1,4-cellobiohydrolase of a thermophilic actinobacterium *Thermobifida fusca* YX, which has a strong cellulase enzyme (Genbank: AAA62211.1).

One gene clone (OJ1-1-11) was obtained from OJ1-1 by PCR cloning. OJ1-1-11 encodes a polypeptide including 548 amino acids, in which 32 amino acids (M1-A32) from methionine (M) (position 1) of the initiation codon to alanine at position 32 is a secretion signal (signal P 4.0), 148 amino acids (T35-P183) from threonine at position 35 to proline at position 182 is a cellulose-binding module CBM3, 112 amino acids (S183-T294) from serine (S) at position 183 to threonine at position 294 is a linker sequence, and 254 amino acids from histidine (H) at position 295 to the end shows a partial amino acid sequence of a cellobiohydrolase catalytic domain belonging to the GH6 family. However, in the following Example 1 <10>, the full length of the pertinent gene clone was expressed by *E. coli* and the PSA and CMC degradation activities were assayed, where no hydrolysis activity to any substrate was observed.

The open reading frame OJ1-2 included 247 amino acids, and was a nucleotide sequence that encodes a polypeptide consisting of only the GH6 catalytic domain. Since the OJ1-2 lacks both the initiation codon and the termination codon, and the cellobiohydrolase of the GH16 family usually includes 400 or more amino acids, OJ1-2 is a non-full length sequence. The amino acid sequence predicted by OJ1-2 is a sequence 100% identical with the amino acid sequence of AR19G-12, from which OJ1-2 is thought to be a gene identical with AR19G-12, being a partial sequence of AR19G-12. The catalytic domain of the gene clone obtained from OJ1-2 by PCR cloning was incorporated in a transformation vector, and expressed by *E. coli*, in which no enzymatic activity to any substrate of PSA and CMC was obtained.

<6> Open Reading Frames AR19G-166 and AR19G-12

The open reading frame AR19G-166 encoded a polypeptide including of 474 amino acids (SEQ ID NO: 9), but was a non-full-length sequence which lacked the initiation codon, and consisted of only a partial sequence of a linker and the GH6 catalytic domain. The GH6 catalytic domain of AR19G-166 showed 66% amino acid sequence identity with a glycoside hydrolase of a mesophilic aerobic bacterium in the phylum Chloroflexi, *Herpetosiphon aurantiacus* DSM 785 (Genbank: ABX04776.1). Two gene clones (AR19G-166-RA and AR19G-166-QV) were obtained from AR19G-166 by PCR cloning using a forward primer composed of the nucleotide sequence represented by SEQ ID NO: 14 (5'-CACCATGTrGGACAATCCATTCATCGGAG-3': 7 nucleotides (CACCATG) were added to the 5'-end side of the nucleotide sequence represented by SEQ ID NO: 12. In the added sequence, ATG on the 3' side is an initiation codon, and CACC on the 5' side is a sequence for insertion into a vector), and a reverse primer composed of the nucleotide sequence represented by SEQ ID NO: 13 (5'-TTAGGGTTGGATCGGCGGATAG-3'). AR19G-166-RA and AR19G-166-QV were only different in two amino acids at position 299 and position 351. In AR19G-166-RA, the amino acid at position 299 was arginine and the amino acid at position 351 was alanine (SEQ ID NO: 1). In AR19G-166-QV, the amino acid at position 299 was glutamine and the amino acid at position 351 was valine (SEQ ID NO: 3).

The open reading frame AR19G-12 encoded a polypeptide including 459 amino acids (SEQ ID NO: 10), but was a non-full-length sequence which lacked the initiation codon, and consisted of only a partial sequence of a linker and the GH6 catalytic domain, similarly to AR19G-166. The GH6 catalytic domain of AR19G-12 showed 64% amino acid sequence identity with a family 6 glycoside hydrolase of *Herpetosiphon aurantiacus* DSM 785 (Genbank: ABX04776.1). However, the catalytic domain of the gene clone obtained from AR19G-12 by PCR was incorporated in a transformation vector, and expressed by *E. coli*, in which no enzymatic activity to any substrate of PSA and CMC was obtained.

<Phylogenetic Analysis>

Unlike genes cloned from cultured and isolated bacterial bodies, the origins of the genes cloned from metagenomic analysis are unknown. It is not known whether the four open reading frames (AR19G-166, AR19G-12 (OJ1-2), and OJ1-1) belonging to the GH6 family obtained from the high temperature soil metagenome originated from prokaryotes such as bacteria or archaea (ancient bacteria), or originated from eukaryotes such as filamentous fungi or mushrooms. Therefore, a phylogenetic analysis was made with a multiple alignment of the amino acid sequences of catalytic domains and a molecular phylogenetic tree, to predict the origins of these open reading frames.

Figure 1:
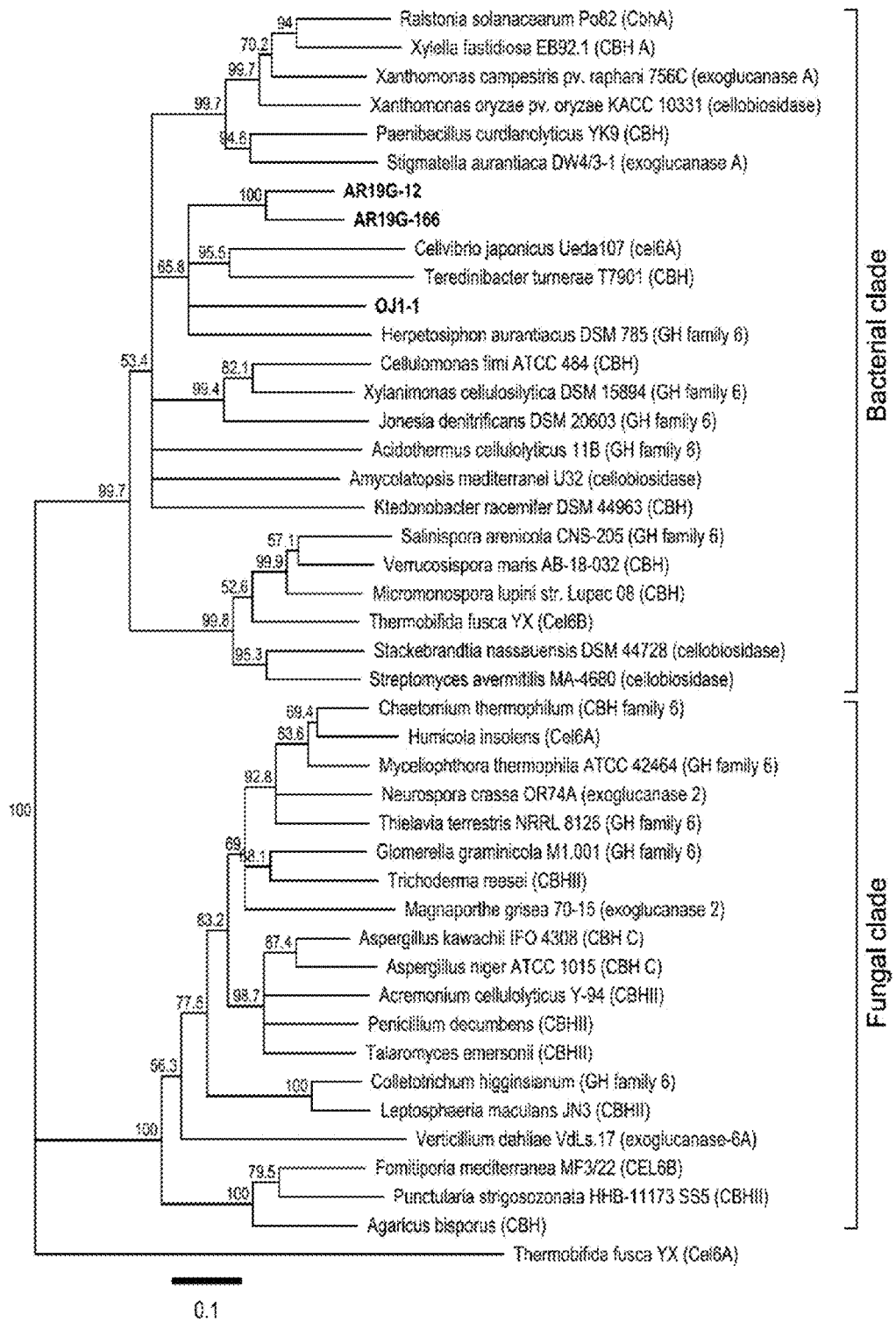
FIG. 1 is a rooted molecular phylogenetic tree of amino acid sequences predicted by four open reading frames (AR19G-166, AR19G-12 (OJ1-2), and OJ1-1) belonging to the GH6 family obtained from a metagenomic analysis in Example 1. OJ1-2 is suggested to be an identical gene to AR19G-12 and is a partial sequence of AR19G-12 because the amino acid sequence is100% homologous (identical) with AR19G-12.

FIG. 1 is a rooted molecular phylogenetic tree of exo-type glycoside hydrolases belonging to the GH6 family (cellobiohydrolase, glycoside hydrolase, exoglucanase, and cellobiosidase). The amino acid sequences predicted by the open reading frames (AR19G-166, AR19G-12 (OJ1-2), and OJ1-1), and the amino acid sequence of the catalytic domain of a thermophilic actinobacterium *Thermobifida fusca* YX Cel6B (Genbank: AAA62211.1), which has a cellulose degradation ability, were subjected to a BLASTP homology search in the Genbank. By so doing, 21 types of sequences of family 6 exo-type glycoside hydrolases were obtained. Next, the amino acid sequence of the catalytic domain of a thermophilic filamentous fungus *Humicola insolens* Cel6A (PDB: 1 VBW) was also subjected to a homology search in the same manner. By so doing, 19 types of sequences were obtained. These 21 bacterial sequences and 19 filamentous fungal sequences, and the amino acid sequences predicted by the open reading frames (AR19G-166, AR19G-12 (OJ1-2), and OJ1-1) hit by the homology search were subjected to a multiple alignment using the Geneious Pro 5.6.5 (Cost Matrix=Blosum80; Gap open penalty=12; Gap extension penalty=3; Alignment type=Global alignment with free end gaps). Then, a phylogenic tree was made by the neighbor-joining method. The endoglucanase belonging to the GH6 family of *Thermobifida fusca* YX Cel6A (Genbank: AAC06388.1) was set as the outgroup. The bootstrap probability was calculated based on 1,000 replicates, and represented by % at each branching point of the phylogenic tree. In FIG. 1, the scale bar on the bottom represents the genetic distance (the mean number of amino acid substitutions/site). Moreover, regarding the enzyme nomenclature shown in the brackets, the term "CBH" is an abbreviation of cellobiohydrolase, and the term "GH" is an abbreviation of glycoside hydrolase.

The bacterial and filamentous fungal family 6 glycoside hydrolases used as the reference of the phylogenic tree are as follows (the number in the brackets shows the accession number of Genbank, Protein Data bank (PDB), or EMBL-Bank). The filamentous fungal family 6 glycoside hydrolases are: *Acremonium cellulolyticus* Y-94 cellobiohydrolase II (Genbank: BAA74458.1); *Agaricus bisporus* cellobiohydrolase (Genbank: AAA50608.1); *Aspergillus kawachii* IFO 4308 1,4-beta-D-glucan cellobiohydrolase C (Genbank: GAA89571.1); *Aspergillus niger* ATCC 1015 1,4-beta-D-glucan cellobiohydrolase C (Genbank: EHA25828.1); *Chaetomium thermophilum* cellobiohydrolase family 6 (Genbank: AAW64927.1); *Colletotrichum higginsianum* glucoside hydrolase family 6 (Genbank: CCF33252.1); *Fomitiporia mediterranea* MF3/22 cellulase CEL6B (Genbank: EJD02201.1); *Glomerella graminicola* M1.001 glucosyl hydrolase family 6 (Genbank: EFQ25807.1); *Humicola insolens* Cel6A (PDB:1BVW); *Leptosphaeria maculans* JN3 cellobiohydrolase II(EMBL-Bank: CBX97039.1); *Magnaporthe grisea* 70-15 exoglucanase 2 (Genbank: EHA57773.1); *Myceliophthora thermophila* ATCC 42464 glucoside hydrolase family 6 (Genbank: AEO55787.1); *Neurospora crassa* OR74A exoglucanase 2 (Genbank: EAA31534.1); *Penicillium decumbens* cellobiohydrolase II (Genbank: ADX86895.1); *Punctularia strigosozonata* HHB-11173 SS5 cellobiohydrolase II (Genbank: EIN07098.1); *Talaromyces emersonii* cellobiohydrolase II (Genbank: AAL33604.4); *Thielavia terrestris* NRRL 8126 glucoside hydrolase family 6 (Genbank: AEO062210.1); *Trichoderma reesei* cellobiohydrolase II (Genbank: AAA34210.1); and *Verticillium dahliae* VdLs.17 exoglucanase-6A (Genbank: EGY16046.1).

The bacterial family 6 glycoside hydrolases are: *Acidothennus cellulolyticus* 11B glucoside hydrolase family 6 (Genbank: ABK52388.1); *Amycolatopsis mediterranei* U32 1,4-beta-cellobiosidase (Genbank: ADJ46954.1); *Cellulomonas fimi* ATCC 484 1,4-beta-cellobiohydrolase (Genbank: AEE46055.1); *Cellvibrio japonicus* Ueda 107 cellobiohydrolase cel6A (Genbank: ACE85978.1); *Herpetosiphon aurantiacus* DSM 785 glucoside hydrolase family 6 (Genbank: ABX04776.1); *Jonesia denitrificans* DSM 20603 glucoside hydrolase family 6 (Genbank: ACV08399.1); *Ktedonobacter racemifer* DSM 44963 1,4-beta-cellobiohydrolase (Genbank: EFH85864.1); *Micromonospora lupini* str. Lupac 08 1,4-beta-cellobiohydrolase (Genbank: CCH20969.1); *Paenibacillus curdlanolyticus* YK9 1,4-beta-cellobiohydrolase (Genbank: EFM08880.1); *Ralstonia solanacearumn* Po82 cellobiohydrolase A (Genbank: AEG71050.1); *Salinispora arenicola* CNS-205 glucoside hydrolase family 6 (Genbank: ABV99773.1); *Stackebrandtia nassauensis* DSM 44728 1,4-beta-cellobiosidase (Genbank: ADD42622.1); *Stigmatella aurantiaca* DW4/3-1 exoglucanase A (Genbank: EAU67050.1); *Streptomyces avermitilis* MA-4680 1,4-beta-cellobiosidase (Genbank: BAC69564.1); *Teredinibacter tumerae* T7901 cellobiohydrolase (Genbank: ACR12723.1); *Thermobifida fusca* YX cellobiohydrolase Cel6B (Genbank: AAA62211.1); *Verrucosispora maris* AB-18-032 1,4-beta-cellobiohydrolase (Genbank: AEB46944.1); *Xanthomonas campestris* pv. *raphani* 756C exoglucanase A (Genbank: AEL08359.1); *Xanthomonas oryzae* pv. *oryzae* KACC 10331 1,4-beta-cellobiosidase (Genbank: AAW77289.1); *Xylanimonas cellulosilytica* DSM 15894 glucoside hydrolase family 6 (Genbank: ACZ30181.1); and *Xylella fastidiosa* Ann-1 cellobiohydrolase A (Genbank: EGO081204.1).

The exo-type glycoside hydrolases belonging to the GH16 family were classified into two clades having a large genetic distance between each other, that is, a bacteria-derived clade and a filamentous fungi-derived clade. In FIG. 1, all in the bottom clade are filamentous fungal family 6 glycoside hydrolases, while all in the top clade are bacterial family 6 glycoside hydrolases. All the open reading frames AR19G-166, AR19G-12, and OJ1-1 are located in the bacterial clade, and constitute one clade with the family 6 glycoside hydrolase of *Herpetosiphon aurantiacus* DSM 785, the cellobiohydrolase cel6A of a gram-negative and wood-degradative bacterium *Cellvibrio japonicus*, and the cellobiohydrolase of a marine γ proteobacterium *Teredinibacter turnerae*.

As shown in FIG. 1, it was found that the four open reading frames (AR19G-166, AR19G-12 (OJ1-2), and OJ1-1) belonging to the GH16 family obtained from the meta-genomic analysis are well apart from the cellobiohydrolase genes of a thermophilic filamentous fungus *Acremonium cellulolyticus*, *Chaetomium thermophilum*, and a wood-decay fungus *Hypocerea jecorina* (*Trichoderma reesei*) in the genetic distance, and these four open reading frames are closely related to the cellobiohydrolase of a thermophilic actinobacterium *Thermobifida fusca* YX as a bacterium, and the family 6 glycoside hydrolase of *Herpetosiphon aurantiacus* DSM 785. From these results, these four open reading frames belonging to the GH6 family are predicted to be cellobiohydrolase genes of bacteria. OJ1-1 has a bacteria-specific cellulose-binding module CBM3, which strongly supports this prediction.

<7> Amino Acid Sequence Alignment

The family 6 glycoside hydrolase of *Herpetosiphon aurantiacus* DSM 785 showing high amino acid sequence identity with AR19G-166-RA and AR19G-166-QV includes 1128 amino acids. This gene is a multi-domain gene including, starting with a transport signal sequence including 29 amino acids from position 1 to position 29, a cellulose-binding module CBM2 including 100 amino acids from position 37 to position 136, a GH6 catalytic domain including 370 amino acids from position 241 to position 611, and furthermore, another GH16 catalytic domain including 370 amino acids from position 713 to position 1082. Both of these GH6 catalytic domains shown by Pfam include 370 amino acid residues, which is shorter than bacterial GH6 catalytic domains, for example, the catalytic domain of *Thermobifida fusca* YX Cel6B including 423 amino acid residues, by 50 amino acid residues or more. Thus, it was considered that they cannot cover the actual catalytic domain. Therefore, the GH6 catalytic domain of *Herpetosiphon aurantiacus* DSM 785 homologous with *Thermobifida fusca* YX Cel6B was searched by BLASTP, which resulted in that, as shown in FIG. 2A, the first GH6 catalytic domain included 428 amino acid residues from valine (V) at position 230 to glutamine (Q) at position 657.

In addition, although the GH6 catalytic domain of OJ1-1 is not in full-length, this partial sequence showed 57% amino acid sequence identity with the GH6 catalytic domain of AR19G-166, and showed only 25% sequence identity with the family 6CBH (TrCBHII) of a filamentous fungus *Trichoderma reesei*.

In the open reading frame AR19G-166, 47 amino acid residues exist in front of the GH6 catalytic domain sequence. Since this amino acid sequence has many times repetition of proline (P) and threonine (T), it was thought to be a part of a linker. Accordingly, the AR19G-166 was suggested to be a multi-domain gene having a cellulose-binding module CBM on the upstream of the cellobiohydrolase catalytic domain via a linker sequence, similarly to OJ1-1.

Figure 2A:
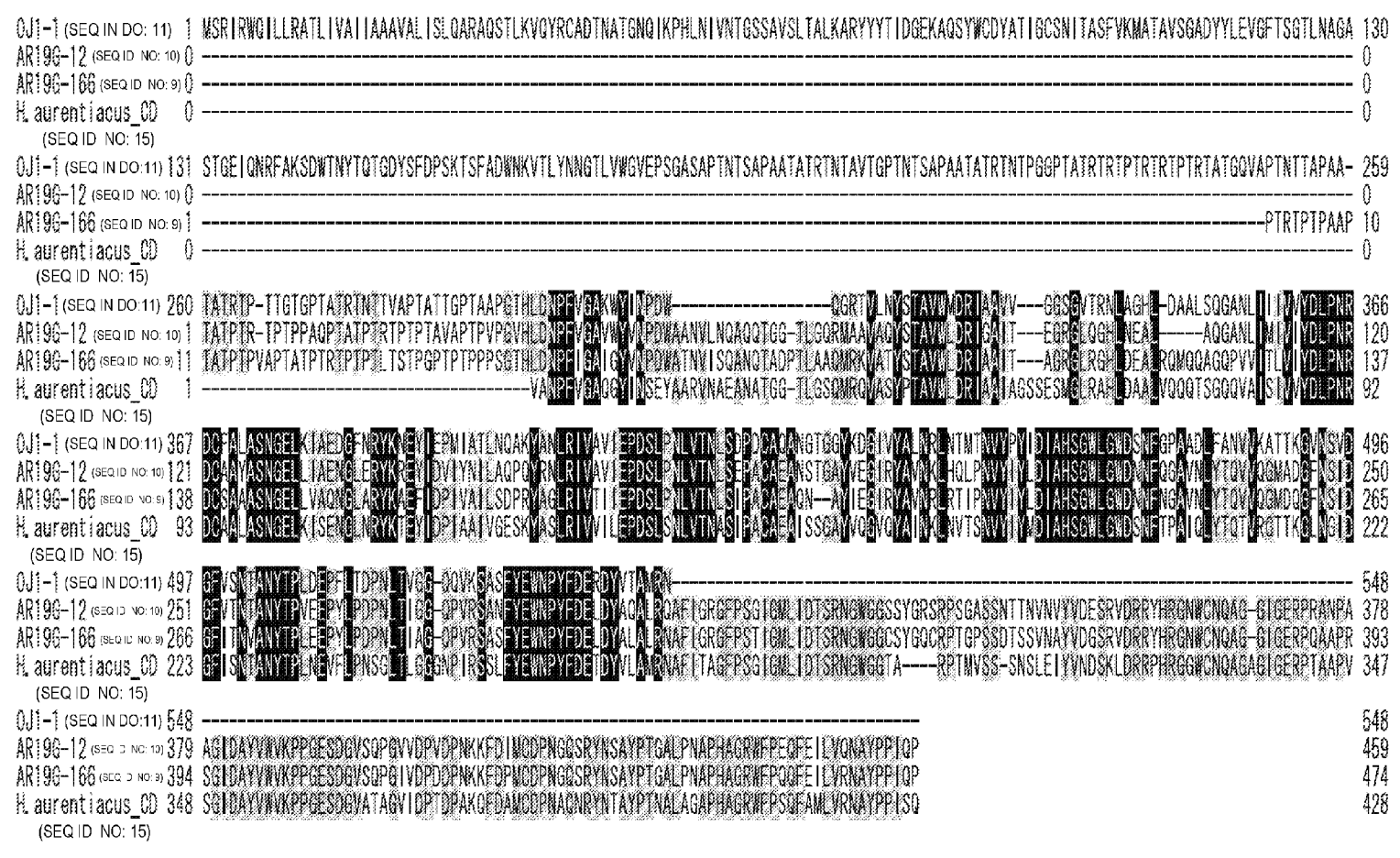
Figure 2B:
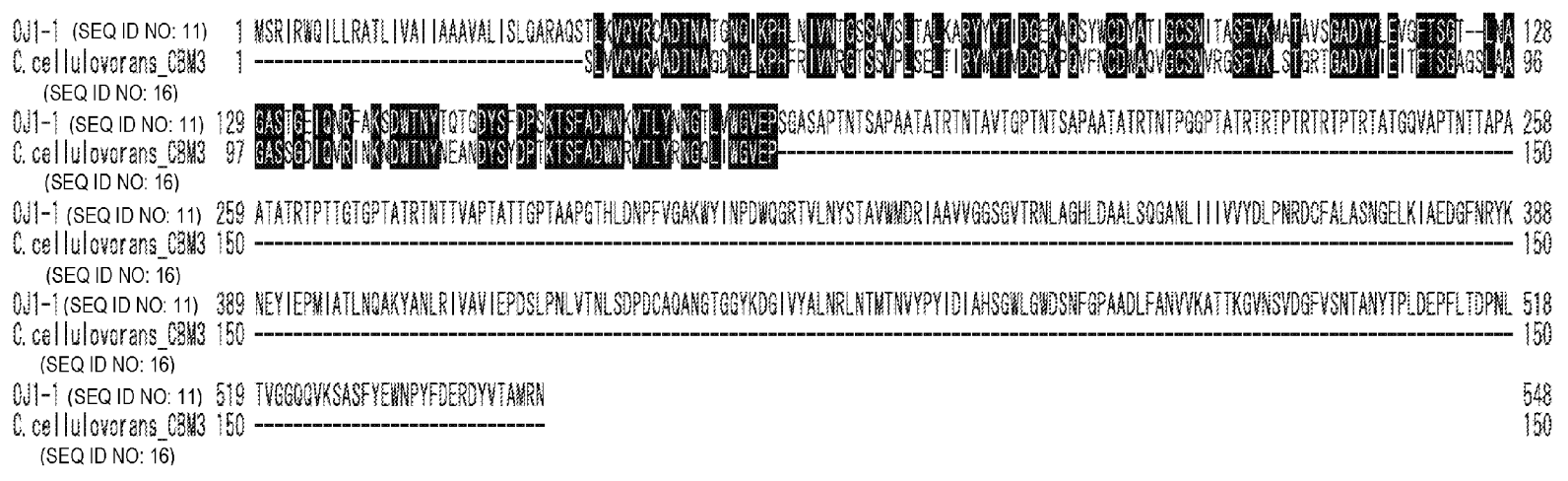

FIG. 2A shows an alignment of the amino acid sequences of polypeptides including the amino acid sequences predicted by the open reading frames (AR19G-166, AR19G-12, and OJ1-1), and the family 6 glycoside hydrolase of *Herpetosiphon aurantiacus* DSM 785. Moreover, FIG. 2B shows an alignment of the amino acid sequence predicted by the open reading frame OJ1-1, and the amino acid sequence of the cellulose-binding module CBM3 of a thermophilic aerobic bacterium *Caldibacillus cellulovorans* (Genbank: AAF22273.1). In FIGS. 2A and 2B, the black/white inverted amino acids denote domains where amino acid residues are preserved throughout all of these amino acid sequences, and the shaded amino acids denote domains where amino acid residues are preserved in most of these amino acid sequences although there are some mutations in some parts of these amino acid sequences.

FIG. 3A shows a schematic diagram of the amino acids of the polypeptides including the amino acid sequences predicted by the open reading frames (AR19G-166, AR19G-12, and OJ1-1) and the CBH gene of *Herpetosiphon aurantiacus* DSM 785. Moreover, FIG. 3B shows a schematic diagram of the amino acid sequence predicted by the open reading frame OJ1-1 and the amino acid of the cellulose-binding module CBM3 of a thermophilic aerobic bacterium *Caldibacillus cellulovorans*. In FIGS. 3A and 3B, the terms "Catalytic domain (partial)" and "Linker (partial)" respectively mean only a part of each domain.

<8> Gene Cloning

The cellobiohydrolase candidate genes obtained by PCR cloning were amplified by PCR using a hot spring soil DNA that had been amplified by the genome DNA amplification kit (GenomiPhi V2 DNA Amplification Kit, manufactured by GE Healthcare), as a template. The amplified PCR products were inserted in the pET101/D-TOPO vector of Champion pET Directional TOPO (registered trademark) Expression Kits (manufactured by Invitrogen), and transfected in One Shot TOP10 strain. Positive clones were selected by colony PCR, and then cultured in a LB liquid medium containing 100 mg/L ampicillin at a temperature of 37° C. and 200 rpm for 17 to 20 hours, followed by the preparation of plasmids using the miniprep kit (Wizard (registered trademark) plus SV Minipreps DNA Purification System, manufactured by Promega). The prepared plasmids were sequenced by using the 3730 DNA Analyzer sequencer of Life Technologies.

<9> Gene Expression and Purification of Cellobiohydrolase Enzymatic Protein

After the sequencing, the plasmids having the target gene were introduced in *E. coli* for protein expression by a heat shock method. The BL21 Star (DE3) strain furnished in the Champion™ pET Directional TOPO (registered trademark) Expression Kits (manufactured by Invitrogen) or the Rosetta-gamiB (DE3) pLysS strain (manufactured by Merck) was used as the competent cell for the transformation. *E. coli* having the target gene was inoculated in a LB medium containing 100 mg/L ampicillin and cultured to about $OD_{600}$=0.2 to 0.8, which was then added with IPTG (isopropyl-β-D(−)-thiogalactopyranoside), and additionally cultured for 5 to 20 hours. By so doing, the expression induction of the target protein was carried out. After the culture, *E. coli* was recovered by centrifugation, to which 50 mM Tris-HCl buffer (pH8) of 1/10-fold volume of the culture liquid was added and suspended. Thereafter, ten cycles of 30 seconds disrupting and 30 seconds halting processes were repeated by using an ultrasonic disrupter, BioRuptor UCD-200T (manufactured by Cosmo Bio Co. Ltd.). By so doing, the crude extract of the gene recombinant *E. coli* containing the target protein was obtained. The crude extract of the gene recombinant *E. coli* was filtrated through a filter (pore side φ=0.45 µm, manufactured by Millipore), and the yielded filtrate was used as a gene recombinant *E. coli* homogenate supernatant.

The gene recombinant *E. coli* homogenate supernatant was filled in an ion-exchange column HiTrap Q HP (manufactured by GE Healthcare) equilibrated with 50 mM Tris-HCl buffer (pH18.0), by which proteins were fractionated with 0 to 50% concentration gradient with 50 mM Tris-HCl buffer (pH8.0) containing 1M NaCl using a middle-to-high pressure liquid chromatography system AKTA design (manufactured by GE Healthcare). The fractions exhibiting cellobiohydrolase activity were all mixed and then subjected to solution exchange into 50 mM Tris-HCl buffer (pH8.0) containing 750 mM ammonium sulfate using a centrifugal ultrafiltration membrane VIVASPIN 20 (manufactured by Sartorius stedim). The fractions with cellobiohydrolase activity after the solution exchange were filled in a hydrophobic interaction separation column HiTrap Phennyl HP (manufactured by GE Healthcare) equilibrated with the same solution, by which proteins were fractionated with 100 to 0% concentration gradient with 50 mM Tris-HCl buffer (pH8.0). The fractions exhibiting cellobiohydrolase activity were all mixed and then enriched by using the VIVASPIN 20 until the liquid volume reached to about 8 mL. The enriched sample was added to a gel filtration column Hiload 26/60 superdex 200 µg (manufactured by GE Healthcare) equilibrated with 50 mM Tris-HCl buffer (pH8.0) containing 150 mM NaCl, and fractionated by flowing the same buffer of 1 to 1.5 fold volume of the column volume at a flow rate of 2 to 3 mL/min. The fractions exhibiting cellobiohydrolase activity were all mixed and then subjected to solution exchange into 50 mM Tris-HCl buffer (pH8.0) and enriched. By so doing, a purified enzyme having the final concentration of about 1 mg/mL was obtained.

The gene recombinant *E. coli* homogenate supernatant and the purified cellobiohydrolase enzymatic protein were checked by SDS-PAGE analysis and Western blotting.

The SDS electrophoresis of the gene recombinant *E. coli* homogenate supernatant and the purified enzyme were respectively conducted by using a 4-20% gradient mini gel and a 10% mini gel (manufactured by ATTO). The supernatant and the purified enzyme were mixed with Tris-SDS βME treatment solution (manufactured by Cosmo Bio Co. Ltd.) at 1:1, and then treated at a temperature of 100° C. for 10 minutes. 5 μL of the gene recombinant *E. coli* homogenate supernatant and 0.5 μL of the purified enzyme per each sample were respectively migrated. After the migration, the immobilized gel was stained with Coomassie Brilliant Blue R250 (manufactured by Merck) to visualize the protein bands.

Regarding the Western blotting of the gene recombinant *E. coli* homogenate supernatant and the purified enzyme. SDS electrophoresis was conducted by using a 10% mini gel (manufactured by ATTO), and then the proteins were transferred onto a polyvinylidene fluoride membrane (manufactured by ATTO) by using a transfer apparatus Trans-Blot SD (manufactured by BioRad). The proteins on the membrane were reacted with 1000-fold diluted rabbit primary antibodies. The rabbit primary antibodies were produced by synthesizing a polypeptide including 20 amino acid residues from positions 384 to 403 encoded by AR19G-166-QV (CDPNGQSRYNSAYPTGALPN), and carrying out an affinity purification of the serum from an immunized rabbit (manufactured by Operon Biotechnologies). The detection of the primary antibody bound to the protein was conducted by using the Fast Western Blotting kit (manufactured by Pierce), and the detection of chemiluminescent signals was conducted by using an imaging apparatus Ez-Capture MG (manufactured by ATTO).

FIG. 4 shows the SDS-PAGE analysis result (FIG. 4(A)) and the Western blot analysis result (FIG. 4(B)) of the enzymatic proteins obtained by expressing AR19G-166-RA and AR19G-166-QV in *E. coli*. The lane 1 is a molecular weight marker for proteins, the lanes 2 and 3 show the electrophoresis patterns of the AR19G-166-RA and AR19G-166-QV gene recombinant *E. coli* homogenate supernatants, and the lanes 4 and 5 show the electrophoresis patterns of the purified AR19G-166-RA protein and AR19G-166-QV protein.

In other words, in FIGS. 4(A) and (B), the lane representations are:
Lane 1: molecular weight marker for proteins;
Lane 2: AR19G-166-RA gene recombinant *E. coli* homogenate supernatant;
Lane 3: AR19G-166-QV gene recombinant *E. coli* homogenate supernatant;
Lane 4: purified AR19G-166-RA protein; and
Lane 5: purified A AR19G-166-QV protein.

The expression of cellobiohydrolase gene is very poor, in general. For example, when the cellobiohydrolase gene is expressed by *E. coli* as a host, the concerned gene is rarely expressed whether the gene is derived from a filamentous fungus or a bacterium. However, both the PCR cloned AR19G-166-RA and AR19G-166-QV were well expressed in *E. coli*. In the SDS-PAGE analysis of the AR19G-166-RA and AR19G-166-QV gene recombinant *E. coli* homogenate supernatants, strong bands were found (lanes 2 and 3 in FIG. 4(A)) at a molecular weight of 46.7 kDa, which were expected from the amino acid sequences (SEQ ID NOs: 1 and 3). After the purification of these proteins, single bands corresponding to the above-mentioned bands were found (lanes 4 and 5 in FIG. 4(A)) in both cases of AR19G-166-RA and AR19G-166-QV. In the Western blotting using antibodies for the polypeptide including 20 amino acid residues from positions 384 to 403 of AR19G-166, single bands of the enzymatic protein were detected at 46.7 kDa in both cases of the gene recombinant *E. coli* homogenate supernatants (lanes 2 and 3 in FIG. 4(B)) and the purified enzyme (lanes 4 and 5 in FIG. 4(B)).

<10> Measurement of Cellobiohydrolase Activity Using PSA as Substrate (PSA Hydrolysis Activity)

Phosphoric acid swollen Avicel (PSA) was used as a substrate in the measurement of the cellobiohydrolase activity. PSA was prepared by once dissolving an Avicel powder (fine crystalline cellulose powder, manufactured by Merck) with a phosphoric acid solution, then precipitating it by adding sterile distilled water, and thereafter washing the same until the pH1 reached 5 or higher. Note that, PSA used for all the following experiments was prepared by this method.

The activity of the gene recombinant *E. coli* homogenate supernatant and the enzyme sample in the middle of purification was measured by reacting a mixture solution including 50 μL of 1 mass % PSA-containing 200 mM acetic acid buffer (pH5.5) with 50 μL of either the gene recombinant *E. coli* homogenate supernatant or the enzyme sample in the middle of purification at a temperature of 30 to 100° C. for 20 minutes.

In all the measurements, a mixture solution prepared by adding 50 mM Tris-HCl buffer (pH8.0) instead of the gene recombinant *E. coli* homogenate supernatant and reacting under the same conditions was used as the control lot. Moreover, the substrate solution and the enzyme were respectively and separately kept at retained reaction temperatures for 5 minutes, and then mixed. This timing was set to the initiation of the reaction. In the reaction, every mixture solution was agitated by using the Eppendorf's Thermomixer (1400 rpm) so as to avoid the precipitation of insoluble substrates. After the completion of the reaction, the same volume of a 3,5-dinitrosalicylic acid reagent (DNS solution) was added. The mixture was treated by heating at a temperature of 100° C. for 5 minutes, cooled down for 5 minutes, and then centrifuged. By so doing, the supernatant was obtained. The absorbance at 540 nm was measured by using a spectrophotometer, and the amount of reduced sugar in the supernatant was calculated by using a calibration curve formed for glucose. The amount of reduced sugar yielded by the enzymatic hydrolysis was obtained by the difference from the control lot. The enzymatic activity for yielding 1 μmol of reduced sugar within 1 minute was set to be 1 U, and the value obtained by dividing it by the protein mass was set to be the specific activity (U/mg).

As a result, among the 44 cellobiohydrolase candidates obtained by PCR cloning, only the polypeptide encoded by the open reading frame AR19G-166 of CBH gene belonging to the GH6 family exhibited PSA hydrolysis activity. The two types of PCR clones obtained from AR19G-166 (AR19G-166-RA and AR19G-166-QV) both exhibited the PSA hydrolysis activities.

<11> Substrate Specificity of Cellobiohydrolase

The hydrolysis activities for various cellulose substrates and hemicellulose substrates were investigated with AR19G-166-RA and AR19G-166-QV which had been confirmed to have PSA hydrolysis activities. In the measurement, the purified enzymes (final concentration of about 1 mg/mL) obtained from the above-mentioned process <9> were used.

The substrate specificity of cellobiohydrolase AR19G-166 was measured by using PSA, an Avicel powder. CMC (carboxymethyl cellulose, manufactured by Sigma), xylan (derived from beechwood, manufactured by Sigma), lichenan (manufactured by MP Biomedicals), and laminarin (derived from *Laminaria digitata*, manufactured by Sigma). Specifically, the measurement was performed by preincubating a mixture solution composed of 50 μL of 200 mM acetic acid buffer (pH5.5), 40 μL of purified water, and 10 μL of purified enzyme at a temperature of 50° C. for 5 minutes, then additionally adding 100 μL of 1 mass % aqueous solution of each substrate thereto, and reacting the mixture at a temperature of 50° C. for 20 minutes (2 hours when the Avicel powder was a substrate). The amount of reduced sugar yielded by the enzymatic hydrolysis was obtained and the specific activity (U/mg) was calculated in the same manner as that of the above-mentioned process <10>. Each measurement was performed by three independent experiments, from which the mean value and the standard deviation were obtained. Furthermore, the relative activity value (%) of the specific activity for each substrate was calculated assuming that the specific activity for PSA was 100%. The results are shown in Table 2.

TABLE 2

Substrate specificity of AR19G-166-RA and AR19G-166-QV

| Substrate and concentration | AR19G-166-RA | | AR19G-166-QV | |
|---|---|---|---|---|
| | Specific activity (U/mg, mean ± s.e.) | Relative value (%) | Specific activity (U/mg, mean ± s.e.) | Relative value (%) |
| 0.5% PSA | 1.81 ± 0.10 | 100% | 1.39 ± 0.07 | 100% |
| 0.5% Avicel | 0.08 ± 0.05 | 4.4% | 0.10 ± 0.03 | 7.2% |
| 0.5% CMC | 0.00 ± 0.01 | 0.0% | 0.00 ± 0.00 | 0.0% |
| 0.5% Laminarin | 0.02 ± 0.01 | 1.1% | −0.02 ± 0.01 | −1.4% |
| 0.5% Lichenan | 0.27 ± 0.02 | 14.9% | 0.26 ± 0.02 | 18.7% |
| 0.5% Xylan | 0.01 ± 0.02 | 0.6% | 0.03 ± 0.02 | 2.1% |

As a result, AR19G-166-RA and AR19G-66-QV exhibited high hydrolysis activities for the water-soluble PSA. In addition, they also exhibited degradation activities for the lichenan including β-1,3 and β-1,4 linked glucans and the crystalline cellulose Avicel. On the other hand, they exhibited almost no degradation activities for CMC, laminarin including β-1,3 and β-1,6 linked glucans, and xylan. The enzyme substrate specificity, which exhibited the hydrolysis activity for the crystalline cellulose Avicel although it was very weak, as well as exhibiting no degradation activity for xylan, suggests that AR19G-166-RA and AR19G-166-QV are cellobiohydrolase belonging to the GH6 family.

<12> HPLC Analysis of PSA Degradation Product

The hydrolysis reaction products of a phosphoric acid swollen Avicel PSA as a substrate with the cellobiohydrolase AR19G-166-RA and the family 6CBH (TrCBHII) of a wood-decay filamentous fungus *T. reesei* were subjected to a componential analysis by means of high-performance liquid chromatography (HPLC). The hydrolysis reaction of PSA was respectively performed with AR19G-166-RA in a 0.1M acetic acid buffer (pH5.5) at a temperature of 70° C., and with TrCBHII in a 0.1M acetic acid buffer (pH4.0) at a temperature of 40° C. for 1 hour and 24 hours, followed by termination of the reaction by the addition of a 0.1M sodium carbonate solution. Each hydrolysis reaction product was centrifuged at a temperature of 4° C. and 12,000 rpm for 10 minutes, and the supernatant was filtrated through a tilter with a pore size of 0.2 μm, and supplied to HPLC analysis. The HPLC apparatus was Alliance e2695 (manufactured by Waters), and the RI detector (2414RI) was used for the detection of sugar. The HPLC apparatus was controlled and analyzed by an analysis software of the Empower version 3.0. The column was the HPLC Carbohydrate Analysis Column 300 mm×7.8 mm (manufactured by BIO-RAD), and the solvent was ultrapure water. 10 μL of the hydrolyzed sample was analyzed at a flow rate of 0.6 mL/min at a column temperature of 85° C. The calibration curve was formed by using standard substances (glucose, cellobiose, and cellotriose), with which sugars were quantified. The maximum concentrations of these samples of the calibration curve were 0.2 mass % for glucose, 0.4 mass % for cellobiose, and 0.5 mass % for cellotriose. After preparing dilution series, the calibration curve was formed by six points.

The measurement results of the componential analysis by HPLC are shown in FIGS. 5A and 5B. The PSA hydrolysis reaction product with AR19G-166-RA included mainly cellobiose (86.5%) with a small amount of cellotriose (13.5%) after 1 hour, and 86.2% of cellobiose and 13.0% of cellotriose, with a very small amount of glucose (0.7%) after 24 hours (FIG. 5A). On the other hand, the PSA hydrolysis reaction product with TrCBHII included mainly cellobiose (87.5%) with a small amount of cellotriose (12.5%), and 88.4% of cellobiose and 9.4% of cellotriose with a very small amount of glucose (2.2%) after 24 hours (FIG. 5B). The results of this HPLC analysis also suggest that AR19G-166 is a cellobiohydrolase.

<13> Temperature and pH Dependencies of Cellobiohydrolase Activity

The temperature dependency and the pH dependency of the PSA hydrolysis activities of AR19G-166-RA and AR19G-166-QV were investigated. In the measurement, the purified enzymes (final concentration of about 1 mg/mL) obtained from the above-mentioned process <9> were used.

The measurement of the PSA hydrolysis activity of the purified enzyme was conducted in the same manner as that of the above-mentioned process <10>, except for reacting a mixture solution composed of 100 μL of a 1 mass % PSA aqueous solution, 50 μL of McIlvaine buffer (pH3 to 8), 40 μL of purified water, and 10 μL of the purified enzyme, at a temperature of 30, 40, 50, 60, 65, 70, 75, 80, 85, 90, or 100° C. for 20 minutes, wherein the amount of reduced sugar yielded by the enzymatic hydrolysis was obtained, and the PSA hydrolysis activity (U/mg) was calculated in the same manner.

The measurement results are shown in FIGS. 6 and 7. FIGS. 6A and 6I are graphs showing the measurement results of the PSA hydrolysis activity at respective temperatures, wherein the horizontal axis represents the temperature. FIGS. 7A and 7B are graphs showing the measurement results of the PSA hydrolysis activity at respective pH values, wherein the horizontal axis represents the pH. The pH was plotted by the actual measurement values of the mixture solution containing the substrate, the buffer, and the enzyme.

The purified enzyme of AR19G-166-RA exhibited high PSA hydrolysis activity in a temperature range from 60 to 80° C. (FIG. 6A). The optimum temperature ($T_{opt}$) showing the highest activity was 70° C. at a pH of 4.5 and 75° C. at a pH of 5.0 to 6.0. When the enzymatic reaction temperature was set to 85° C. or higher, the PSA hydrolysis activity of the purified enzyme of AR19G-166-RA was rapidly decreased in all pH ranges. On the other hand, the purified enzyme of AR19G-166-QV exhibited lower PSA hydrolysis activity than that of AR19G-166-RA at a temperature of 65° C. or higher (FIG. 6B). The optimum temperature ($T_{opt}$) showing the highest activity was 70° C. at a pH of 4.5 to 5.5 and 75° C. at a pH of 6.0. The PSA hydrolysis activity of the purified enzyme of AR19G-166-RA was rapidly decreased in all pH ranges when the enzymatic reaction temperature was 80° C. or higher.

Moreover, the purified AR19G-166-RA exhibited the highest PSA hydrolysis activity within a range of the reaction temperature from 65 to 80° C. and a pH of 4 to 6 (FIG. 7A). The optimum pH varied depending on the reaction temperature, which was a pH of 4.6 (actual measurement value) at a temperature of 60 to 65° C., a pH of 5.2 to 5.3 (actual measurement value) at a temperature of 70 to 75° C. and a pH of 5.8 (actual measurement value) at a temperature of 80° C. A low level of PSA hydrolysis activity was observed in ranges of a pH of 3.2 to 4.5 and a pH of 7 to 8. On the other hand, the purified enzyme of AR19G-166-QV, similarly to AR19G-166-RA, exhibited the highest PSA hydrolysis activity within a range of pH4 to 6, and a low level of PSA hydrolysis activity in ranges of pH3.2 to 4.5 and pH7 to 8 (FIG. 7B).

<14> Thermostability (Half-Life Time of the Enzymatic Activity)

In order to investigate the thermostability of AR19G-166-RA and AR19G-166-QV, preincubation was conducted for 20 minutes to 1440 minutes, and the PSA hydrolysis activity of the enzymatic protein was measured at respective temperatures.

In the measurement, the purified enzymes (final concentration of about 1 mg/mL) obtained from the above-mentioned process <9> were used. The preincubation of each purified enzyme was carried out by keeping the temperature of a mixture solution (pH5.0) composed of 10 μL of the purified enzyme, 40 μL of purified water, and 50 μL of a 200 mM acetic acid buffer, at respective temperature of 50 to 80° C. for 0, 20, 40, 60, 120, 240, 480, 960, or 1440 minutes. The measurement of the PSA hydrolysis activity was conducted in the same manner as that of the above-mentioned process <10>, except for separately warming the preincubated mixture solution and a 1 mass % PSA aqueous solution respectively at a temperature of 50° C. for 5 minutes, then adding 100 μL of the PSA aqueous solution to the mixture solution, and reacting it for 20 minutes, wherein the amount of reduced sugar yielded by the enzymatic hydrolysis was obtained, and the PSA hydrolysis activity (U/mg) was calculated in the same manner.

The measurement results are shown in FIGS. 8A and 8B. The enzymatic activity was shown as the relative value (Relative activity %) assuming that the activity of the nontreated lot (without preincubation) was 100%. As shown by the broken and drop line of FIG. 8A, the preincubation time at which the enzymatic activity was reduced to 50% of that of the nontreated lot was set to the half-life $T_{half}$.

When the preincubation temperature was from 50 to 60° C. the purified AR19G-166-RA did not lose the PSA hydrolysis activity within the measurement time, and the half-life $T_{half}$ was 24 hours, which was the upper limit of the measurement, or longer. At a temperature of 70° C., the half-life $T_{half}$ was calculated to be 226 minutes from the approximate curve made by the exponent function represented by the bold line of FIG. 8A. At a temperature of 80° C., the enzymatic activity was immediately lost by the preincubation (FIG. 8A).

On the other hand, the thermostability of the purified AR19G-166-QV was much lower than that of AR19G-166-RA. When the preincubation temperature was 50° C., the PSA hydrolysis activity was hardly lost within the measurement time, and the half-life $T_{half}$ was 24 hours or longer. With the increase of the preincubation temperature, the half-life $T_{half}$ of the enzymatic activity was shortened, meaning 16 hours at 60° C., and much shortened at 70° C., meaning 40 minutes. At a temperature of 80° C., the enzymatic activity was immediately lost (FIG. 8B).

<15> Effect of Divalent Metal Ions on Thermostability

Generally, divalent metal ions are known to stabilize the structure of a protein by binding to the protein, thereby improving the thermostability. Each divalent metal ion (concentration of 1 mM) of calcium ($Ca^{2+}$), manganese ($Mn^{2+}$), cobalt ($Co^{2+}$), barium ($Ba^{2+}$), magnesium ($Mg^{2+}$), nickel ($Ni^{2+}$), divalent iron ($Fe^{2+}$), trivalent iron ($Fe^{3+}$), and zinc ($Zn^{2+}$) was administered in an enzyme-substrate (PSA) reaction solution to measure the effect on the PSA hydrolysis activity of the enzymatic protein. First, a mixture solution composed of 10 μL of the purified enzyme solution (concentration of 1 mg/mL), 40 μL of purified water or a 5 mM aqueous solution of a chloride of each divalent metal, and 50 μL of a 200 mM of acetic acid buffer (pH5.5) was preincubated at a temperature of 30° C. for 30 minutes. The measurement of the PSA hydrolysis activity was conducted in the same manner as that of the above-mentioned process <10>, except for separately warming the preincubated mixture solution and a 1 mass % PSA aqueous solution respectively at each temperature of 30 to 100° C. for 5 minutes, then adding 100 μL of the PSA aqueous solution to the mixture solution, and reacting it at each temperature for 20 minutes, wherein the amount of reduced sugar yielded by the enzymatic hydrolysis was obtained, and the PSA hydrolysis activity (U/mg) was calculated in the same manner.

As a result, the enzymatic activities of AR19G-166-RA and AR19G-166-QV were increased at a temperature of 85° C. or higher by the administration of calcium ion or cobalt ion of the final concentration of 1 mM, and the enzymatic activities were remarkably increased in a temperature range of 60 to 90° C. by the administration of manganese ion (not shown). The other divalent metal ions showed no effect ($Ba^{2+}$, $Mg^{2+}$, and $Ni^{2+}$), or rather worsened the enzymatic activities ($Fe^{2+}$, $Fe^{3+}$, and $Zn^{2+}$).

<16> Melting Temperature of the Enzymatic Protein

Another indicator associated with the thermostability of a protein is the thermal denaturation or melting temperature, $T_m$. The preincubation temperature at which the enzymatic activity is reduced to 50% of that of the nontreated lot by preliminary heating (preincubation) is equal to the $T_m$ of the protein, and can be obtained by measuring the enzymatic activity, as shown by the broken and drop line of FIG. 9A. The $T_m$ of AR19G-166-RA and AR19G-166-QV were obtained by this method.

A mixture solution including 10 μL of the purified enzyme solution (concentration of about 1 mg/mL), 40 μL of purified water or a 5 mM aqueous solution of a chloride of divalent metal ion ($CaCl_2$ or $MnCl_2$), and 50 μL of a 200 mM acetic acid buffer (pH5.0) was incubated at a temperature of 30° C. for 30 minutes, and thereafter preincubated at a temperature of 40 to 100° C. for 30 minutes. The measurement of the PSA hydrolysis activity was conducted in the same manner as that of the above-mentioned process <10>, except for separately warming the preincubated mixture solution and a 1 mass % PSA aqueous solution respectively at a temperature of 50° C. for 5 minutes, then adding 100 μL, of the PSA aqueous solution to the mixture solution, and reacting it at a temperature of 50° C. for 20 minutes, wherein the amount of reduced sugar yielded by the enzymatic hydrolysis was obtained, and the PSA hydrolysis activity (U/mg) was calculated in the same manner. For each preincubation temperature, the PSA hydrolysis activity value of the enzyme was measured three times, from which the mean value and the standard error were obtained. The data were normalized by assuming that the mean values of the hydrolysis activities of a low temperature region (40 to 65° C.) and the high temperature region (90 to 100° C.), at which the hydrolysis activity was saturated, were respectively 1 and 0.

The PSA hydrolysis activities of the AR19G-166-RA protein and the AR19G-166-QV protein at respective preincubation temperatures and the approximate curves by means of sigmoid function are shown in FIGS. 9A and 9B. From the approximate curve, the $T_m$ value of the enzymatic protein (that is, the preincubation temperature at the time when the normalized activity=0.5) was obtained. The $T_m$ values of the enzymatic proteins calculated from these approximate curves of the PSA hydrolysis activity data are shown in Table 3. In Table 3, the term "Control" shows the result of the reaction in which purified water was added instead of 5 mM of the aqueous solution of the chloride of divalent metal ion. The $T_m$ value of AR19G-166-RA was 76.4° C., while the $T_m$ value of AR19G-166-QV was 68.5° C., meaning that the $T_m$ value of AR19G-166-RA was higher than that of AR19G-166-QV by about 8° C. In addition, the $T_m$ of the AR19G-166-RA and AR19G-166-QV were respectively increased by 3.0° C. and 4.1° C. by the administration of manganese ion having the concentration of 1 mM. The $T_m$ value of AR19G-166-RA was slightly increased (by 0.7° C.), whereas the $T_m$ value of AR19G-166-QV was increased by 3.1° C., by the administration of calcium ion having the concentration of 1 mM.

TABLE 3

Melting temperature ($T_m$) of AR19G-166-RA and AR19G-166-QV

| Enzyme | $T_m$ (° C.) | | |
|---|---|---|---|
| | Control | +1 mM Ca$^{2+}$ | +1 mM Mn$^{2+}$ |
| AR19G-166-RA | 76.4 | 77.1 | 79.4 |
| AR19G-166-QV | 68.5 | 71.6 | 74.6 |

Example 21

When an arbitrarily gene is introduced in a eukaryotic organism such as a filamentous fungus or a plant as a host, the optimum temperature of the expressed protein generally increased by about 5 to 10° C. This is attributed to the posttranslational modification reaction to add sugars to proteins, which is called glycosylation. The glycosylated proteins become stable against heat. The AR19G-166 gene was introduced in a filamentous fungus Aspergillus oryzae, to verify the effect of glycosylation to the thermostability of the encoded enzymatic protein.

<1> Production of Aspergillus Transformant

An AR19G-166-RW mutant (amino acid sequence: SEQ ID NO: 5 and nucleotide sequence: SEQ ID NO: 6) and an AR19G-166-QW mutant (amino acid sequence: SEQ ID NO: 7 and nucleotide sequence: SEQ ID NO: 8) in which the amino acid residue at position 351 of AR19G-166-RA and AR19G-166-QV was substituted with tryptophan (W), were produced. The expression cassette including each of them was introduced in Aspergillus. By so doing. Aspergillus transformants to express AR19G-166-RW or AR19G-166-QW were produced.

These amino acid substitution mutants of the AR19G-166 gene were incorporated in a transformation vector to construct the expression vector. This vector was transfected in Aspergillus as a host. The Aspergillus transformant was produced by the contract protein expression service of Ozeki Co., Ltd. The Aspergillus transformation offered by this service features the homologous recombination method, in which the introduced gene is incorporated in a specific site of the chromosome. Thus, although the competence of a filamentous fungus is low, once it is incorporated in the chromosome, the introduced gene is stably retained and the protein encoded by the introduced gene can be stably generated. Moreover, since the secretion signal is added, the protein encoded by the introduced gene is secreted from the bacterial body into the culture solution.

<2> Enrichment of Protein Generated by Aspergillus Transformant

The thus obtained Aspergillus transformant was cultured, and thereafter the supernatant of the cultured solution was recovered. This culture supernatant was enriched into 1/10 volume by using a centrifugation type ultrafiltration membrane VIVASPIN 20 (manufactured by Sartorius stedim), and was subjected to solution exchange into 50 mM Tris-HCl buffer (pH8.0). This was used as the enriched supernatant.

5 µL of each enriched supernatant of the respective Aspergillus transformants and 5 µL of the AR19G-166-RA gene and AR19G-166-QV gene recombinant E. coli homogenate supernatants prepared in Example 1 were subjected to Western blot analysis. The Western blot analysis was conducted in the same manner as that of the process <9> of Example 1, and the result is shown in FIG. 10. From the enriched supernatants of the AR19G-166-RW-introduced Aspergillus transformant and the AR19G-166-QW-introduced Aspergillus transformant, very weak bands which correspond to the single bands of the AR19G-166 gene recombinant E. coli homogenate supernatant were observed (lanes 2 and 3 in FIG. 10) at 46.7kD, and furthermore, strong and broad bands appeared at 50 to 55 kDa (lanes 2 and 3 in FIG. 10). In this manner, the apparent molecular weights of most proteins encoded by the AR19G-166 gene expressed by Aspergillus as a host were increased by about 3 to 8 kDa. This increase of the molecular weight can be attributed to the glycosylation.

In other words, further to the above discussion and the explanations provided, it will be understood that in FIG. 10, each line shows the western blot analysis result of the following sample.

Lane 1: molecular weight marker for proteins;
Lane 2: AR19G-166-RA gene recombinant E. coli homogenate supernatant;
Lane 3: AR19G-166-QV gene recombinant E. coli homogenate supernatant;
Lane 4: enriched supernatant of AR19G-166-RW-introduced Aspergillus transformant; and
Lane 5: enriched supernatant of AR19G-166-QW-introduced Aspergillus transformant.

<3> Production of E. coli Transformant with AR19G-166-RW and AR19G-166-QW Genes and Purification of Cellobiohydrolase Enzymatic Protein Plasmids in which the mutants AR19G-166-RW and AR19G-166-QW had been inserted in the pET101/D-TOPO vector were produced in the same manner as that of the process <8> of Example 1. E. coli transformants in which these plasmids had been introduced in E. coli for protein expression were produced in the same manner as that of the process <9> of Example 1. The thus obtained E. coli transformants were subjected to the expression induction. After culturing, E. coli was recovered by centrifugation. The crude extract of the recombinant E. coli containing the target protein was obtained and filtrated. By so doing, the E. coli homogenate supernatant was obtained. Fractionation and purification were conducted by the ion-exchange column, the hydrophobic interaction separation column, and the gel filtration column, in the same manner as that of the process <9> of Example 1. By so doing, the purified enzyme having the final concentration of about 1 mg/mL was obtained.

<4> Temperature Dependency of Cellobiohydrolase Activity

The temperature dependencies of the PSA hydrolysis activities of AR19G-166-RW and AR19G-166-QW generated by the gene recombinant *Aspergillus* transformant and the gene recombinant *E. coli* were investigated. In the measurement, the enriched supernatants obtained in the above-mentioned process <2> and the purified enzymes obtained in the above-mentioned process <3> were used.

The measurement of the PSA hydrolysis activity at each temperature was conducted in the same manner as that of the above-mentioned process <13> of Example 1, except for using the enriched supernatants obtained in the above-mentioned process <2>, and setting the pH of the reaction solution at 5.5, wherein the amount of reduced sugar yielded by the enzymatic hydrolysis was obtained in the same manner. The PSA hydrolysis activities of the purified enzymes of AR19G-166-RW and AR19G-166-QW expressed by *E. coli* were calculated in the same manner as that of the process <10> of Example 1, meaning that the enzymatic activity for yielding 1 μmol of reduced sugar within 1 minute was set to be 1 U, and the value obtained by dividing it by the protein mass was set to be the specific activity (U/mg). On the other hand, the PSA hydrolysis activities of AR19G-166-RW and AR19G-166-QW generated by the *Aspergillus* transformant were calculated as the relative activity value (%) assuming that the amount of reduced sugar by AR19G-166-RW exhibiting the maximum hydrolysis activity at a temperature of 100° C. was 100%.

The calculated relative activity values (%) of the PSA hydrolysis activities at respective temperatures are shown in FIG. 11A. In FIG. 11A, the measurement results of the PSA hydrolysis activities (U/mg) of AR19G-166-RW and AR19G-166-QW expressed by *E. coli* having been measured in the process <13> of Example 1 are also shown (in the graph, respectively denoted by "RW by *E. coli*" and "QW by *E. coli*"). The optimum temperatures ($T_{opt}$) of AR19G-166-RW and AR19G-166-QW expressed by *E. coli* were respectively 80° C. and 75° C. On the other hand, the optimum temperatures of AR19G-166-RW and AR19G-166-QW expressed by *Aspergillus* (in the graph, respectively denoted by "RW by *A. oryzae*" and "QW by *A. oryzae*") were both 100° C. or higher. In this way, it was revealed that the molecular weight was increased by about 10%, and the optimum temperature was increased by 20 to 30° C. when expressing the AR19G-166 gene by *Aspergillus*. The AR19G-166 expressed by *Aspergillus* showed a higher optimum temperature by 30° C. or higher and better thermostability, than those of conventional thermophilic filamentous fungi-derived cellobiohydrolases.

From these results, it is apparent to be possible to obtain an enzyme having favorable cellobiohydrolase activity even at a temperature of 80° C. or higher, by expressing the thermostable cellobiohydrolase according to the present invention by an expression system of a eukaryotic organism such as a filamentous fungus. It becomes possible, by using such a thermostable cellobiohydrolase exhibiting high enzymatic activity even at a temperature of 80 to 100° C. together with other thermostable cellulases, to conduct the hydrolysis process of lignocellulose in high temperature conditions at 80° C. or higher.

<5> pH Dependency of Cellobiohydrolase Activity

The pH dependencies of the PSA hydrolysis activities of AR19G-166-RW and AR19G-166-QW generated by the *Aspergillus* transformant and the *E. coli* transformant were investigated. In the measurement, the enriched supernatants obtained in the above-mentioned process <2> and the purified enzymes obtained in the above-mentioned process <3> were used.

The measurement of the PSA hydrolysis activity at each pH was conducted in the same manner as that of the above-mentioned process <13> of Example 1, except for using the enriched supernatants obtained in the above-mentioned process <2>, wherein the amount of reduced sugar yielded by the enzymatic hydrolysis was obtained in the same manner. The AR19G-166-RW and AR19G-166-QW generated by the *E. coli* transformant were subjected to the PSA hydrolysis reaction respectively at a temperature of 80° C. and 75° C., and their PSA hydrolysis activities (U/mg) were calculated. The AR19G-166-RW and AR190-166-QW generated by the *Aspergillus* transformant were subjected to the PSA hydrolysis reaction at the temperature of 80° C., and their PSA hydrolysis activities at respective pH values were calculated as the relative activity value (%) assuming that the PSA hydrolysis activity exhibiting the maximum activity at a pH of 5.2 was 100%.

The calculated relative activity values (%) of the PSA hydrolysis activities at respective pH values are shown in FIG. 11B. In FIG. 11B, the measurement results of the PSA hydrolysis activities (U/mg) of AR19G-166-RW and AR19G-166-QW expressed by *E. coli* having been measured in the process <13> of Example 1 are also shown (in the graph, respectively denoted by "RW by *E. coli*" and "QW by *E. coli*"). The AR19G-166 enzymes expressed by *Aspergillus* (in the graph, respectively denoted by "RW by *A. oryzae*" and "QW by *A. oryzae*") showed broader pH specificity than that of the AR19G-166 enzymes expressed by *E. coli* (in the graph, denoted by "RW by *E. coli*" and "QW by *E. coli*"). The pH at which 50% activity of the maximum value is exhibited was in a range of 3.3 to 8.0 at a reaction temperature of 80° C. On the other hand, this pH range was from 4.5 to 6.8 in the case of the expression by *E. coli*.

Example 31

In general, protein production of a recombinant gene using a plant as a host offers a much higher expression level compared with bacterial expression systems such as *E. coli* or *Bacillus*, and filamentous fungal expression systems such as *Aspergillus*. In particular, chloroplast transformants accumulate a foreign protein at a ratio of 5 to 10 mass % relative to total soluble proteins (TSP) in their transformant leaves, and sometimes show very high accumulation of 40 mass % or greater relative to TSP. On the other hand, nuclear genome transformation accumulates a foreign protein at a ratio of about 1 mass % relative to TSP in the transformant tissue. In this manner, the production of a protein by a plant, and particularly the production of a foreign protein by a chloroplast transformant, offers significant economic merit compared with bacterial or filamentous fungal culture, which represent the conventional platforms for protein production. Accordingly, a tobacco chloroplast transformant was produced by inserting AR19G-166-RA and AR19G-166-QV in the chloroplast genome of tobacco.

<1> Production of Tobacco Chloroplast Transformants

The introduction region into the chloroplast genome, the 5'/3' expression regulatory region, and the selection marker gene and the like which constitute the chloroplast transformation construct were designed with reference to previously reported examples showing high expressions of foreign proteins (Daniell et al., Methods in Molecular Biology, 2005, Vol. 286, p. 111-138, Verma and Daniell, Plant Physiol., 2007, Vol. 145, p. 1129-1143).

First, the cassette vectors pNtaGL and pNtaGLPL for the tobacco chloroplast transformation having the structures shown in FIG. 12A were produced. These vectors are vectors for introducing a target gene by means of homologous recombination into the trnI-trnA intergenic region in the inverted repeat sequence within the tobacco chloroplast genome. The vectors have an expression cassette of the aadA (aminoglucoside 3'-adenylyltransferase) gene as a selection marker to be indicated by spectinomycin resistance, and have an expression cassette introduction site (ClaI-BsiWI site) for the target gene downstream of the aadA gene expression cassette. A tobacco-derived 16S ribosome RNA gene promoter (Prrn) is inserted in the pNtaGL vector as an expression regulatory region of the aadA gene, whereas the pNtaGLPL vector does not include a promoter region, and the expression of the aadA gene is dependent on the endogenous promoter upstream of the homologous recombination region.

FIG. 12B shows the expression cassettes for the target gene, pPXT and pPXTPL. Both cassettes are designed to insert the target gene in the BamHI site, and respectively have the Prrn promoter and the bacteriophage T7-derived gene 10 (T7g10) sequence, or only the T7g10 sequence, on the 5' side of the target gene. The T7g10 sequence is a sequence thought to be effective for high accumulation of a foreign protein in the chloroplast expression of the foreign gene. The 3'-UTR (TrbcL) of the tobacco chloroplast rbcL gene is arranged on the 3' side of the target gene in both cassettes, and in each case, can be introduced into the cassette vector pNtaGL or pNtaGLPL for the chloroplast transformation shown in FIG. 12A by using the ClaI site and the BsiWI site at the opposite ends of each cassette.

The PCR clones AR19G-166-RA and AR19G-166-QV were respectively amplified with primers having a BamHI linker, and the resulted amplification products were inserted in the BamHI site of the expression cassette pPXT or pPXTPL. The expression cassette pPXT in which the AR19G-166-QV had been inserted was incorporated into pNtaGL utilizing the ClaI site and the BsiWI site, thereby producing a chloroplast transformation construct pNtaGL-QV having a structure in which the aadA gene expression cassette and the AR19G-166-QV expression cassette were linked in tandem in the trnI-trnA intergenic region. The expression cassette pPXTPL in which the AR19G-166-RA had been inserted was incorporated into pNtaGLPL in a similar manner, thereby producing a chloroplast transformation construct pNtaGLPL-RA. FIG. 12C shows schematic illustrations of the structures of these chloroplast transformation constructs pNtaGL-QV and pNtaGLPL-RA. In FIG. 12C, "QV" means AR19G-166-QV and "RA" means AR19G-166-RA.

The transformation of tobacco chloroplast was conducted basically in accordance with the method of Daniell et al. (Daniell et al., Methods in Molecular Biology, 2005, Vol. 286, p. 111-138). Specifically, green leaves of tobacco (Nicotiana tabacum cv. SR-1) having been aseptically disseminated and grown in an MS plate medium (Murashige and Skoog (MS) medium (pH 5.8) containing 30 g/L sucrose solidified with 3 g/L gellan gum) were cut into 0.5 cm squares, and the cut leaves were arrayed in the center of a Petri dish filled with an RMOP medium (Svab et al., Proc. Natl. Acad. Sci. U.S.A., 1990, Vol. 87, p. 8526-8530) so that the adaxial sides of the leaves were in contact with the medium. After culturing for a day under conditions of a 16-hour light period and an 8-hour dark period, pNtaQV or pNtaRA, and a pNtaGL or pNtaGLPL vector as a control for the purposes of comparative analysis, were respectively introduced using a particle gun (PDS-1000He, zz About 100 mg of leaf pieces were collected from the spectinomycin-resistant shoots obtained through three or four repetitions of dedifferentiation and regeneration, and the DNAs were extracted from these leaf pieces. Using the DNA as a template, PCR were conducted using primers designed to specifically amplify the introduced sequences, thereby selecting individuals having each target sequence introduced in the trnI-trnA region of the tobacco chloroplast genome.

Individuals confirmed as having the introduced AR19G-166-RA or AR19G-166-QV and the corresponding vector control were transplanted in an MS medium containing 500 mg/L of spectinomycin to promote rooting and growth of the plant body. DNAs were extracted from the plants grown to about 10 cm height by using the DNeasy Plant Mini Kit (manufactured by QIAGEN), and the homoplasmy of the introduced gene were checked by Southern blotting. Specifically, first, 1 μg of each DNA extracted from leaves of the chloroplast transgenic tobacco or wild-type tobacco (WT (SR-1)) was digested with the restriction enzyme BglII. The BglII-digested DNAs were subjected to Southern blotting by using a probe including a nucleotide sequence identical to the upstream region of trnI of about 1 kb, and the probe was detected by chemiluminescence using the AlkPhos Direct of GE Healthcare. In theory, the probe should detect about 4.5 kb DNA fragments for the wild-type tobacco, 7.1 kb DNA fragments for the pNtaGL-QV and pNtaGLPL-RA chloroplast transgenic tobacco, and 6.0 kb or 5.9 kb DNA fragments for the pNtaGL or pNtaGLPL vector chloroplast transgenic tobacco. The results of Southern hybridization of two lines of chloroplast transgenic tobacco obtained by the introduction of pNtaGL-QV (QV-2 and QV-17), and three lines of chloroplast transgenic tobacco obtained by the introduction of pNtaGLPL-RA (RA-6-2-1, RA-6-2-2 and RA-6-2-3), are shown in FIGS. 13A and 13B respectively. Further, the results of Southern hybridization of chloroplast transgenic tobacco obtained by the introduction of pNtaGL and pNtaGLPL vectors are shown in FIG. 13C. In all cases, only the 7.1 kb band, the 6.0 kb band or the 5.9 kb band derived from the recombinant chloroplast was detected, with no detection of the approximately 4.5 kb band derived from the wild-type chloroplast, and therefore these lines were confirmed to be homoplasmic chloroplast transformants in which all the chloroplasts were of the recombinant types.

The homoplasmic chloroplast transformants were grown further, transplanted to a culture soil in an 18 cm pot at the time when they had about seven leaves, and then cultivated in a greenhouse for transgenic plants. The chloroplast transformants containing the introduced AR19G-166-QV and AR19G-166-RA respectively did not show any morphological abnormality during the subsequent growth, and developed seeds. The phenotype analyses of the $T_1$ plants revealed that although the growth were slightly slower than that of the wild-type and the vector control-introduced chloroplast transformants, no morphological abnormity were found, and the amounts of biomass in the flowering period were similar to that of the vector controls. FIG. 14A is a photograph showing the flowering period of an AR19G-166-QV-introduced chloroplast transgenic tobacco plant ($T_1$ generation) and a vector control (pNtaGL), and similarly, FIG. 14B is a photograph showing the flowering period of an AR19G-166-RA tobacco plant ($T_1$ generation) and a vector control (pNtaGLPL).

In other words, it will be understood that in FIGS. 14A and 14B, the legends are as follows.
"QV" of FIG. 14A shows an AR19G-166-QV-introduced chloroplast transgenic tobacco plant
(T1 generation);
"pNtaGL" of FIG. 14A shows a vector control;
"RA" of FIG. 14B shows an AR19G-166-RA tobacco plant (T1 generation); and
"pNtaGLPL" of FIG. 14B shows a vector control.

<2> Extraction of Cellobiohydrolase Enzymatic Protein from Chloroplast Transgenic Tobacco Extraction of cellobiohydrolase enzymatic protein was performed by selecting one line of each of the AR19G-166-QV and AR19G-166-RA-introduced chloroplast transgenic tobacco plants, and then conducting extraction from 3 individuals of each line in the manner described below. Three leaves were taken from the central region of the chloroplast transgenic tobacco plant during the flowering period, and 5 to 10 leaf pieces of about 100 mg were cut from each leaf. The leaf pieces were placed in a 2 mL sample tube containing three tungsten beads with a diameter of 3 mm (manufactured by QIAGEN), and in this state, the sample tube was placed in liquid nitrogen and frozen. The frozen leaf pieces were crushed using a mixer mill MM400 (manufactured by Retsch) at 30 Hz for 90 seconds, and a suspension was prepared by adding a 50 mM acetic acid buffer (pH 5.5) containing 1 volume % of a protease inhibitor (manufactured by Sigma) in an amount equal to 10 times the weight of the leaf pieces. Following thorough mixing of the suspension, a centrifugal separation was performed, thus preparing a soluble protein extract containing the enzymatic protein (AR19G-166-QV or AR19G-166-RA). In the case of the AR19G-166-RA extract, the extract was concentrated 5 to 10-fold using a centrifugal ultrafiltration membrane VIVASPIN 20 (manufactured by Sartorius Stedim). Further, using the same procedure, soluble protein extracts were also prepared from pNtaGL or pNtaGLPL vector-introduced chloroplast transgenic tobacco plants as controls for the purpose of comparative analysis.

The soluble protein extracts were checked by SDS-PAGE analysis and Western blot analysis. The SDS electrophoresis and the Western blotting were performed using a Mini Protean TGX Stain-Free gel (manufactured by Bio-Rad). Each of the extracts and purified enzymes was mixed with a Tris-SDS β-ME treatment solution (manufactured by Cosmo Bio Co. Ltd.) at 1:1, and then treated at a temperature of 100° C. for 10 minutes. Five μL of the AR19G-166-Qv, 10 μL of the AR19G-166-RA and the control individual, and 0.2 μg of the purified enzyme respectively were migrated. Following the migration, the protein bands were detected by CBB staining. The Western blotting was performed in the same manner as that described for Example 1 <9>.

FIG. 15A to FIG. 15D show the results of SDS-PAGE analysis (FIG. 15A) and Western blot analysis (FIG. 15B) of soluble protein extracts obtained from the chloroplast transgenic tobacco plant obtained by the introduction of AR19G-166-QV and the chloroplast transgenic tobacco plant obtained by the introduction of pNtaGL, and the results of SDS-PAGE analysis (FIG. 15C) and Western blot analysis (FIG. 15D) of soluble protein extracts obtained from the chloroplast transgenic tobacco plant obtained by the introduction of AR19G-166-RA and the chloroplast transgenic tobacco plant obtained by the introduction of pNtaGLPL. In each of FIG. 15A to FIG. 15D, lane 1 is a molecular weight marker for proteins, lane 2 is the purified enzymatic protein, lanes 3 to 5 are soluble protein extracts obtained from 3 individual chloroplast transgenic tobacco plants into which AR19G-166-QV or AR19G-166-RA has been introduced, and lanes 6 to 8 are soluble protein extracts obtained from 3 individual chloroplast transgenic tobacco plants into which pNtaGL or pNtaGLPL has been introduced.

In other words, in FIGS. 15A and 15B, the lane representations are:
Lane 1: molecular weight marker for proteins;
Lane 2: purified enzymatic protein;
Lane 3: soluble protein extract obtained from chloroplast transgenic tobacco plant into which AR19G-166-QV has been introduced;
Lane 4: soluble protein extract obtained from chloroplast transgenic tobacco plant into which AR19G-166-QV has been introduced;
Lane 5: soluble protein extract obtained from chloroplast transgenic tobacco plant into which AR19G-166-QV has been introduced;
Lane 6: soluble protein extract obtained from chloroplast transgenic tobacco plant into which pNtaGL has been introduced;
Lane 7: soluble protein extract obtained from chloroplast transgenic tobacco plant into which pNtaGL has been introduced; and
Lane 8: soluble protein extract obtained from chloroplast transgenic tobacco plant into which pNtaGL has been introduced.

Further, in FIGS. 15C and 15D, the lane representations are:
Lane 1: molecular weight marker for proteins;
Lane 2: purified enzymatic protein;
Lane 3: soluble protein extract obtained from chloroplast transgenic tobacco plant into which AR19G-166-RA has been introduced;
Lane 4: soluble protein extract obtained from chloroplast transgenic tobacco plant into which AR19G-166-RA has been introduced;
Lane 5: soluble protein extract obtained from chloroplast transgenic tobacco plant into which AR19G-166-RA has been introduced;
Lane 6: soluble protein extract obtained from chloroplast transgenic tobacco plant into which pNtaGLPL has been introduced;
Lane 7: soluble protein extract obtained from chloroplast transgenic tobacco plant into which pNtaGLPL has been introduced; and
Lane 8: soluble protein extract obtained from chloroplast transgenic tobacco plant into which pNtaGLPL has been introduced.

The AR19G-166-QV and AR19G-166-RA enzymatic proteins were both expressed in the tobacco chloroplast. In the SDS-PAGE analysis of the soluble protein extracts of the AR19G-166-QV and AR19G-166-RA chloroplast transgenic tobacco plants, bands were detected (in lanes 3 to 5 of FIG. 15A and FIG. 15C) in a position corresponding with the respective purified enzymatic protein (lane 2 of FIG. 15A and FIG. 15C). On the other hand, no such bands were detected in the control individuals having introduced pNtaGL or pNtaGLPL (lanes 6 to 8 of FIG. 15A and FIG. 15C).

Western blotting was performed using an antibody against a polypeptide including 20 amino acid residues from positions 384 to 403 of AR19G-166, and in the soluble protein extracts of both the AR19G-166-QV chloroplast transgenic tobacco plants (lanes 3 to 5 of FIG. 15B) and the AR19G-

166-RA chloroplast transgenic tobacco plants (lanes 3 to 5 of FIG. 15D), bands were detected in a position corresponding with the respective purified enzymatic protein (lane 2 of FIG. 15B and FIG. 15D). Further, in the AR19G-166-QV and the AR19G-166-RA, bands were also observed in a position of lower molecular weight than the enzymatic protein. It is thought that this band is probably due to mixing of an enzymatic protein resulting from digestion of a portion of the enzymatic protein within the plant, or an enzymatic protein of incomplete expression. On the other hand, in the control individuals having introduced pNtaGL or pNtaGLPL (lanes 6 to 8 of FIG. 15B and FIG. 15D), absolutely no bands were detected.

<3> Temperature Dependency of Cellobiohydrolase Activity

The temperature dependency of the PSA hydrolysis activities of AR19G-166-QV and AR19G-166-RA produced by chloroplast transgenic tobacco was investigated. In the measurements, the soluble protein extracts obtained above were used.

The measurement of the PSA hydrolysis activity at each temperature was conducted using the soluble protein extracts obtained above, in the same manner as that described in Example 1 <10>, and the amount of reduced sugar produced by the enzymatic hydrolysis was determined.

The PSA hydrolysis activities at various temperatures of the AR19G-166-QV protein and the AR19G-166-RA protein expressed in the tobacco chloroplast are shown in FIG. 16A and FIG. 16B respectively. In FIG. 16A and FIG. 16B, the enzymatic activities across a temperature range from 30° C. to 100° C. are represented by the amount of reduced sugar. The results revealed that the AR19G-166-QV and the AR19G-166-RA expressed in tobacco chloroplast exhibited similar temperature dependency of the PSA hydrolysis activity to that of the AR19G-166-QV and the AR19G-166-RA expressed in E. coli, confirming normal protein function. Although the results varied slightly for each individual, the tobacco chloroplast-expressed AR19G-166-QV (FIG. 16A) exhibited an optimum temperature ($T_{opt}$) of 70 to 75° C., and displayed thermostability substantially similar to that of the AR19G-166-QV expressed in E. coli. Similarly, in the case of the tobacco chloroplast-expressed AR19G-166-RA (FIG. 16B), although the results varied slightly for each individual, the optimum temperature ($T_{opt}$) was 75 to 80° C. and displayed thermostability substantially similar to that of the AR19G-166-RA expressed in E. coli. In contrast, in the control individuals containing introduced pNtaGL or pNta-GLPL, no PSA hydrolysis activity was observed.

Example 4

When an arbitrary gene is introduced into a eukaryote such as a filamentous fungus or a plant as a host, the optimum temperature of the expressed protein generally increases by about 5 to 10° C. This is attributed to the posttranslational modification reaction to add sugars to proteins, which is called glycosylation. The glycosylated proteins become stable relative to heat. In the amino acid residue sequence of the AR19G-166-RA gene and the AR19G-166-QV gene, the N-linked glycosylation motif Asn-Xaa-Ser/Thr exists in four locations. When gene expression is performed using a eukaryote as a host, there is a possibility that glycosylation may occur at these motifs, meaning an improvement in the thermostability can be expected. The AR19G-166-RA gene and the AR19G-166-QV gene were introduced into Arabidopsis thaliana, which is a plant of the Brassicaceae family, to verify the effect of glycosylation on the thermostability of the encoded enzymatic protein.

<1> Production of Arabidopsis thaliana Transformant

PCR was conducted using the AR19G-166-RA gene and the AR19G-166-QV gene as templates, which were incorporated into an apoplast accumulation type plant expression vector plG121 Bar. Using a freezing and thawing method, the expression vector was introduced into Agrobacterium tumefaciens. Specifically, about 1 μg of the plasmid (expression vector) was added to a competent cell of the EHA105 strain of the Agrobacterium dissolved in ice, and following gentle mixing, the liquid was frozen instantaneously using liquid nitrogen. Subsequently, thawing was performed by warming at a temperature of 37° C. for 4 minutes, 0.5 mL of a SOC medium was added, and cultivation was performed at a temperature of 28° C. for 1 to 3 hours. The thus obtained culture solution was applied to an LB agar medium containing 50 mg/L of kanamycin and 10 mg/L of PPT (phosphinothricin), and by performing standing culture for 2 days in an incubator at 28° C., a transformed Agrobacterium was obtained. Following liquid culturing of the transformed Agrobacterium, the plasmid was extracted, and sequencing was performed using a 3730 DNA Analyzer Sequencer (manufactured by Life Technologies).

Next, using an Arabidopsis thaliana plant that had been grown for about 2 months at 22° C. using a 24-hour light period and the transformed Agrobacterium that had been cultured using the LB agar medium containing 50 mg/L of kanamycin and 10 mg/L of PPT, a transformed Arabidopsis thaliana was produced.

First, an Agrobacterium culture solution having OD600=about 1 was harvested and suspended in a solution containing 5% sucrose and 0.05% Silwet. Subsequently, the Arabidopsis thaliana plant was dipped in the Agrobacterium suspension for several seconds to infect the seeds. Following maturing of the seeds, the seeds were collected, and transformant selection was performed using a 1/2 MS medium containing 50 mg/L of kanamycin and 10 mg/L of PPT, thus obtaining 6 individuals of AR19G-166-RA cellobiohydrolase transgenic Arabidopsis thaliana, and 4 individuals of AR19G-166-QV cellobiohydrolase transgenic Arabidopsis thaliana. Two of these individuals, Arabi_RA4 and Arabi_QV4 were investigated for cellobiohydrolase enzymatic activity.

<2> Extraction and Enzymatic Activity Assay of Cellobiohydrolase Enzymatic Protein Produced by Arabidopsis thaliana Transformant Extraction of the protein was performed by grinding 100 mg of leaves from the transformed Arabidopsis thaliana individual under liquid nitrogen using a mortar and pestle, subsequently adding a 20 mM acetic acid buffer (pH5.5) containing 1 mL of a 1 volume % Protease Inhibitor Cocktail (manufactured by Sigma-Aldrich), and mixing thoroughly. The resulting mixture was transferred to a 2 mL microtube and subjected to centrifugal separation for 10 minutes at 15,000 rpm and a temperature of 4° C., and the supernatant was collected as a crude enzyme extract. A crude enzyme extract prepared in a similar manner using a wild-type Arabidopsis thaliana was used as a control (untransformed lot).

For individuals of the Arabidopsis thaliana transformants Arabi_RA4 and Arabi_QV4 and the control (untransformed), Western blot analyses were performed using the crude enzyme extracts to confirm the cellobiohydrolase recombinant gene expression. The Western blot analyses were performed in the same manner as that described in Example 1 <9>, and the results are shown in FIG. 17. In FIG. 17, lane 1 is a molecular weight marker for proteins, lane 2 is the crude enzyme extract from the leaves of the AR19G-166-RA transgenic *Arabidopsis thaliana* (Arabi_RA4), lane 3 is the crude enzyme extract from the leaves of the AR19G-166-QV transgenic *Arabidopsis thaliana* (Arabi_QV4), and lane 4 is the crude enzyme extract from the leaves of the wild-type *Arabidopsis thaliana* (WT).

The crude enzyme extracts of the *Arabidopsis thaliana* transformant containing the introduced AR19G-166-RA (Arabi_RA4) and the *Arabidopsis thaliana* transformant containing the introduced AR19G-166-QV (Arabi_QV4) displayed strong bands at 53.9 kDa and 52.1 kDa respectively. The molecular weight of the enzymatic protein of the transformant Arabi_RA4 was slightly larger than that of the transformant Arabi_QV4 (lanes 2 and 3 of FIG. 17). The size of the protein when produced in *E. coli* is 46.7 kDa, indicating that the apparent molecular weights of the proteins encoded by the AR19G-166-RA gene and the AR19G-166-QV gene expressed using *Arabidopsis thaliana* as a host increased by 7.2 kDa and 5.4 kDa respectively. These increases in molecular weight are due to glycosylation, and it is thought that the difference in the molecular weights of the expressed enzymatic proteins in the transformants Arabi_RA4 and Arabi_QV4 is due to a difference in the degree of glycosylation.

<3> Temperature Dependency of Cellobiohydrolase Activity of *Arabidopsis thaliana* Expressed AR19G-166 Proteins The temperature dependency of the PSA hydrolysis activities of the AR19G-166-RA enzymatic protein and the AR19G-166-QV enzymatic protein produced by the above-mentioned gene transgenic *Arabidopsis thaliana* transformants was investigated. In the measurements, the crude enzyme solutions obtained above in <2> were used, and testing was performed in the same manner as Example 1 <10> to determine the amount of reduced sugar produced by the enzymatic hydrolysis.

The calculated PSA hydrolysis activities (amounts of reduced sugar) at various measured temperatures are shown in FIG. 18. In FIG. 18, the cellobiohydrolase activity of a wild-type *Arabidopsis thaliana* (WT) was measured and plotted for the purposes of comparison.

For the AR19G-166-RA enzymatic protein expressed using *Arabidopsis thaliana* as the host, the temperature at which the highest enzymatic activity was observed was 100° C., which was the upper limit of the measurements, and it is assumed that the optimum temperature is 100° C. or higher. On the other hand, the optimum temperature for the AR190-166-QV enzymatic protein was 90° C. In this manner, when the AR19G-166 gene is expressed in the nuclear genome system of *Arabidopsis thaliana*, the molecular weight increases about 10%, and the optimum temperature increases by 15 to 30° C. The *Arabidopsis thaliana* expressed AR190-166-RA exhibits particularly superior thermostability, and has an optimum temperature that is 30° C. or more higher than a conventional thermostable cellobiohydrolase derived from a thermophilic filamentous fungus.

Based on these results, it is clear that by expressing the thermostable cellobiohydrolase according to the present invention in the nuclear genome expression system of a plant or a eukaryote such as a filamentous fungus, an enzyme having a high level of cellobiohydrolase activity even at 80° C. or higher can be obtained. By using the ultra thermostable cellobiohydrolase of the present invention, which exhibits high enzymatic activity in the temperature range from 80 to 100° C., in combination with a similarly thermostable endoglucanase, xylanase or β-glucosidase or the like, hydrolysis treatment of lignocellulose can be performed under high-temperature conditions of 80° C. or higher.

Example 5

Actinobacteria of the genus *Streptomyces* are known to produce useful antibiotics and bioactive substances, and are widely used in industry. Large scale expression systems for foreign genes using the substance production capabilities of these bacteria are now being developed, and a number of successful examples have been reported (Patent Documents 3, 4 and 5, and Non-Patent Documents 9, 10 and 11). In particular, it has been reported that because actinobacteria have a genome with a high GC content, the expression of genes having a high GC content, which has proven problematic in *E. coli*, tends to occur favorably (Non-Patent Document 11), and that the expression of a heteroprotein can be achieved at an extremely high level approaching 40% of the actinobacterium cell-free extract (Non-Patent Document 9). The expression of protein in an actinobacterium into which the AR19G-166-RA gene had been introduced was investigated as a potential means of inexpensive and large scale production of the thermostable cellobiohydrolase according to the present invention.

<1> Production of Actinobacterium Having Introduced AR19G-166-RA Gene

Using AR19-G-166-RA genes cloned with the pET101/D-TOPO vector (manufactured by Life Technologies) as a template, the genes were transferred to an actinobacterium expression vector pHSA81 (Patent Document 4) by PCR, and then transfected in the *Streptomyces lividans* TK24 strain. The TK24 strain is available from John Innes Centre (Norwich Research Park, Norwich, NR4 7UH, UK) or the like.

The above-mentioned transfection was conducted in accordance with a method (protoplast polyethylene glycol fusion method) disclosed in "Genetic manipulation of *Streptomyces*: a laboratory manual". Following transfection, positive clones were selected by colony PCR, and following shaking culture in YEME medium (yeast extract: 0.3%, bacto-peptone: 0.5%, malt extract: 0.3%, glucose: 1%, sucrose: 34%. $MgCl_2$: 5 mM, glycine: 0.5%), the recombinant plasmid was extracted, and sequencing was performed using a 3730 DNA Analyzer Sequencer (manufactured by Life Technologies).

<2> Expression of AR19G-166-RA Protein in Actinobacterium

The obtained transformant was inoculated in a YEME medium containing 5 µg/mL of thiostrepton, subjected to shaking culture at 28° C. for 5 days, and then collected by centrifugal separation. Following washing of the bacterium in a 50 mM Tris-HCl buffer (pH 8.0), an amount of the same buffer equal to 1/10 th of the volume of the culture solution was added and suspended. Subsequently, a process comprising 30 seconds disruption using a BioRuptor UCD-200T (manufactured by Cosmo Bio Co. Ltd.) and 30 seconds rest was repeated 10 times, and following subsequent centrifuging, SDS-PAGE analysis was performed using the supernatant (cell-free extract). The results are shown in FIG. 19. Lane 1 in FIG. 19 is a molecular weight marker for proteins, lane 2 is the AR19G-166-RA purified protein (indicated by the arrow) expressed in *E. coli*, and lane 3 is the cell-free extract of the AR19G-166-RA gene recombinant actinobacterium *Streptomyces lividans*. In FIG. 19, a strong expression of the target protein was confirmed at the anticipated size (46.7 kDa) (lane 3 in FIG. 19).

<3> Measurement of Enzymatic Activity of Actinobacterium-Expressed AR19G-166-RA Protein Measurement of the cellobiohydrolase activity was conducted using the cell-free extract of the AR19G-166-RA gene recombinant actinobacterium. The activity measurement was performed by reacting a mixture containing a 50 µL sample of the cell-free extract and 50 µL of a 200 mM acetic acid buffer (pH 5.5) containing 1 mass % of phosphoric acid swollen Avicel (PSA) at a temperature of 30 to 100° C. for 20 minutes.

The substrate solution and the enzyme were held separately at the reaction temperature for 5 minutes, and were then mixed to initiate the reaction. During the reaction, all of the mixed solutions were agitated using a Thermomixer manufactured by the Eppendorf (1400 rpm) so as to avoid the precipitation of insoluble substrates. In all of the measurements, a mixed solution obtained by reacting only 50 µL of the 200 mM acetic acid buffer (pH 5.5) containing 1 mass % of phosphoric acid swollen Avicel (PSA) at each temperature, and then adding a 50 µL sample of the cell-free extract following halting of the reaction was used as a control lot. Following completion of the reaction, an equal volume of a 3,5-dinitrosalicylic acid reagent (DNS solution) was added, a heat treatment was performed at 100° C. for 5 minutes, and after cooling for 5 minutes, the mixture was centrifuged to obtain a supernatant. The absorbance of the supernatant at 540 nm was measured using a spectrophotometer, the amount of reduced sugar in the supernatant was calculated by using a calibration curve prepared for glucose, and the difference from the value for the control lot was used to determine the amount of reduced sugar produced by the enzymatic hydrolysis. Each measurement was performed using three independent samples, and the average value and the standard error were determined. The results are shown in FIG. 20. In FIG. 20, three measurements were performed for each data point, and the average value and the standard error were plotted against the temperature.

The enzymatic activity for producing 1 µmol of reduced sugar within 1 minute was deemed 1 U, and when the value obtained by dividing the result by the mass of the enzymatic protein was deemed the specific activity (U/mg), a specific activity at 80° C. of 3.02 was obtained. As illustrated above, the AR19G-166-RA cellobiohydrolase enzyme also exhibited favorable expression and activity in an actinobacterium, and it was clear that such actinobacteria could also be used as a gene introduction host for the present invention.

Example 6

Among cellulases, there are enzymes which not only have a catalytic domain that hydrolyzes cellulose, but also have a module with a cellulose binding function (CBM, carbohydrate-binding module). The CBM does not itself have degradation activity, but does have an unassisted cellulose binding function. Known functions of CBMs include increasing the concentration of catalytic domains attributable to the CBM in the vicinity of the substrate by adsorbing to the insoluble substrate, thereby increasing the cellulose degradation rate, and severing hydrogen bonding between cellulose chains through CBM binding, thereby destroying crystal structures (Non-Patent Documents 12 and 13). Further, if the CBM is removed from CBH which degrades crystalline cellulose, then although the reactivity relative to soluble substrates does not change, the degradation activity and affinity relative to crystalline cellulose decrease dramatically, and therefore it is thought that CBM is a domain that is required for the enzyme to act upon crystalline cellulose (Non-Patent Document 14). On the other hand, it has also been reported that by adding CBM to a type of endoglucanase which originally has no CBM, the affinity and degradation activity relative to crystalline cellulose can be improved (Non-Patent Document 5).

In order to further enhance the cellulose degradation activity of the thermostable cellobiohydrolase according to the present invention, a gene prepared by adding CBM to AR19G-166-RA was produced, and the effect of adding CBM on the cellulose degradation activity of the encoded enzymatic protein was investigated.

<1> Production of CBM-Added AR19G-166-RA Gene

The CBM sequence and the linker sequence used the sequence of the open reading frame OJ1-1 shown in Example 1 <5>. The linker sequence of the open reading frame OJ1-1 was added to the C-end side of the AR19G-166-RA gene, adding the CBM3 sequence of the open reading frame OJ1-1 to the C-end side. The nucleotide sequence of the entire length of the CBM-added AR19G-166-RA gene was optimized for the codon usage frequency of E. coli and synthesized artificially. The amino acid sequence of the added linker and CBM3 gene is represented by SEQ ID NO: 17 and the nucleotide sequence is represented by SEQ ID NO: 18, whereas the amino acid sequence of the entire length of the CBM-added AR19G-166-RA gene optimized for the codon usage frequency of E. coli is represented by SEQ ID NO: 19 and the nucleotide sequence is represented by SEQ ID NO: 20. The 3 nucleotides TAA from position 808 to position 810 of SEQ ID NO: 18, and the 3 nucleotides TAA from position 2092 to position 2094 of SEQ ID NO: 20 are both stop codons.

The gene synthesized in the manner described above was incorporated in the Expression Vector pLEAD (manufactured by NIPPON GENE Co., Ltd.), a transformation was performed with the JM109 strain, and sequencing was performed using a 3730 DNA Analyzer Sequencer manufactured by Life Technologies.

<2> Expression of CBM-Added AR19G-166-RA Protein

Following sequencing, an E. coli clone retaining the plasmid having the target gene was inoculated in 5 mL of an LB medium containing 100 mg/L of ampicillin, and shaking culture was performed at 37° C. for 20 hours. After culturing, the E. coli was collected by centrifugal separation, and an amount of a 50 mM Tris-HCl buffer (pH 8) equal to ¹/₁₀th of the volume of the culture solution was added and suspended. Subsequently, a process comprising 30 seconds disruption using a BioRuptor UCD-200T (manufactured by Cosmo Bio Co. Ltd.) and 30 seconds rest was repeated 10 times, and centrifuging was then performed to obtain a supernatant (E. coli crude extract). A portion of the E. coli crude extract was migrated by SDS-PAGE, and an expression of the target protein was confirmed at the anticipated size. Following confirmation of the protein expression, an E. coli solution that had been cultured overnight at 37° C. was used as the preculture solution, and the main culturing was performed in a 100-fold amount of an LB medium containing 100 mg/L of ampicillin.

<3> Purification of CBM-Added AR19G-166-RA Protein

Following culturing, centrifugal separation was performed to collect the E. coli, and an amount of a 50 mM Tris-HCl buffer (pH 8) equal to ¹/₁₀th of the volume of the culture solution was added and suspended. Subsequently, a process comprising 5 minutes disruption using an ultrasonic disruption apparatus Astrason 3000 (manufactured by Misonix, Inc.) and 5 minutes rest was repeated 7 to 8 times, yielding a crude extract of a gene recombinant *E. coli* containing the target protein. The gene recombinant *E. coli* crude extract was filtered through a filter (pore size φ=0.45 μm, manufactured by Millipore), and the thus obtained filtrate was used as a gene recombinant *E. coli* homogenate supernatant.

The gene recombinant *E. coli* homogenate supernatant was poured into an ion-exchange column HiTrap Q HP (manufactured by GE Healthcare) equilibrated with 50 mM Tris-HCl buffer (pH 8.0), and using a middle-to-high pressure liquid chromatography system AKTA design (manufactured by GE Healthcare), the proteins were fractionated with a 0 to 50% concentration gradient using a 50 mM Tris-HCl buffer (pH 8.0) containing 1M of NaCl. The fractions exhibiting cellobiohydrolase activity were mixed together, subsequently subjected to solution exchange and enrichment into a 1 mM phosphoric acid buffer (pH 6.8) using a centrifugal ultrafiltration membrane VIVASPIN 20 (manufactured by Sartorius Stedim), and then passed through a hydroxyapatite column CHT5-1 (manufactured by Bio-Rad) equilibrated with the same buffer to fractionate the proteins with a 0 to 100% concentration gradient using a 400 mM phosphoric acid buffer (pH 6.8). The fractions exhibiting cellobiohydrolase activity were mixed together, and then enriched using the VIVASPIN 20 until the liquid volume reached about 8 mL. The enriched sample was added to a gel filtration column Hliload 26/60 superdex 200 μg (manufactured by GE Healthcare) equilibrated with a 50 mM Tris-HCl buffer (pH 8.0) containing 150 mM of NaCl, and was fractionated by passing an amount of the same buffer equal to 1 to 1.5 times the column volume through the column at a flow rate of 2 to 3 mL/min. The fractions exhibiting cellobiohydrolase activity were mixed together, subsequently subjected to solution exchange and enrichment into a 50 mM phosphoric acid buffer (pH 6) using the VIVASPIN 20, and then passed through an ion-exchange column HiTrap SP HP (manufactured by GE Healthcare) equilibrated with the same buffer to fractionate the proteins with a 0 to 50% concentration gradient using a 50 mM phosphoric acid buffer (pH 6) containing 1M of NaCl. The fractions exhibiting cellobiohydrolase activity were mixed together, and then subjected to solution exchange into a 50 mM Tris-HCl buffer (pH 8.0) and enriched, thus obtaining a purified enzyme with a final concentration of about 1 mg/mL.

The gene recombinant *E. coli* homogenate supernatant and the purified CBM-added AR19G-166-RA protein were checked by SDS-PAGE analysis and Western blot analysis. With the exception of using Mini Protean TGX Stain-Free gel (manufactured by Bio-Rad), the SDS-PAGE analysis and the Western blot analysis were performed in the same manner as Example 1 <9>, and 10 μL of the gene recombinant *E. coli* homogenate supernatant and 0.5 μg of the purified enzyme respectively were migrated. In the SDS-PAGE analysis, the protein bands were detected using a Gel Doc EZ Imager (manufactured by Bio-Rad).

FIG. 21A and FIG. 21B show the results of the SDS-PAGE analysis (FIG. 21A) and the Western blot analysis (FIG. 21B) of the enzymatic protein obtained by expressing the CBM-added AR19G-166-RA protein in *E. coli*. In FIG. 21A and FIG. 21B, lane 1 is a molecular weight marker for proteins, lane 2is the gene recombinant *E. coli* homogenate supernatant, lane 3 is the purified CBM-added AR19G-166-RA protein, and lane 4is the electrophoretic pattern of the cellobiohydrolase enzymatic protein purified in Example 1<9>.

In other words, in FIGS. 21A and 21B, the lane representations are:
Lane 1: molecular weight marker for proteins;
Lane 2: gene recombinant *E. coli* homogenate supernatant;
Lane 3: purified CBM-added AR19G-166-RA protein; and
Lane 4: cellobiohydrolase enzymatic protein purified in Example 1<9>.

The CBM-added AR19G-166-RA protein was expressed in *E. coli*. In the SDS-PAGE analysis of the gene recombinant *E. coli* homogenate supernatant, a band was confirmed near the molecular weight of 74.5 kDa predicted from the amino acid sequence (SEQ ID NO: 19) (lane 2 of FIG. 21A). When this protein was purified, a strong band corresponding with the above band was observed, but a weak band was also confirmed near a molecular weight of 60 kDa (lane 3 of FIG. 21A). Western blot analysis was performed using an antibody against a polypeptide including 20 amino acid residues from positions 384 to 403 of AR19G-166, and in the gene recombinant *E. coli* homogenate supernatant (lane 2 of FIG. 21B), an enzymatic protein band was detected near the molecular weight of 74.5 kDa. Further, a band was also detected near the molecular weight of 60 kDa, but it is thought that this band is probably due to mixing of an enzymatic protein resulting from digestion of a portion of the enzymatic protein within the cells of the *E. coli*, or an enzymatic protein of incomplete expression. In a similar manner, in the purified enzyme (lane 3 of FIG. 21B), a strong band was detected for the enzymatic protein near the molecular weight of 74.5 kDa, and a weak band was detected near the molecular weight of 60 kDa, but the main constituent protein was confirmed as being the above-mentioned enzymatic protein.

<4> Activity of CBM-Added AR19G-166-RA Protein

The temperature dependency of the PSA and Avicel hydrolysis activity of the CBM-added AR19G-166-RA protein was investigated. In the measurements, the purified enzyme obtained above (final concentration: about 1 mg/mL) was used.

Measurement of the hydrolysis activity of the purified enzyme relative to PSA and Avicel was conducted in the same manner as that described in Example 1 <10>, with the exception of reacting a mixed solution including 100 μL of a 1 mass % substrate aqueous solution, 50 μL of a 200 mM acetic acid buffer (pH 5.5), 40 μL of pure water or a 10 mM aqueous solution of $CaCl_2$, and 10 μL of the purified enzyme for 20 minutes at a temperature of 50, 60, 70, 75, 80, 85, 90 or 99° C., and the amount of reduced sugar produced by the enzymatic hydrolysis was determined to calculate the hydrolysis activity (U/mg).

The PSA hydrolysis activity and the Avicel degradation activity of the CBM-added AR19G-166-RA protein at various temperatures are shown in FIG. 22A and FIG. 22B respectively. The results revealed that for the PSA hydrolysis activity, no effects of the CBM addition were apparent, regardless of the presence or absence of calcium ions, and the hydrolysis activity actually decreased relative to that of the lone AR19G-166-RA protein (FIG. 22A). However, in the case of the Avicel degradation activity, a dramatic increase in the degradation activity was observed across a broad temperature range from 50° C. to 85° C. in the presence of calcium ions (FIG. 22B). On the other hand, in the absence of calcium ions, no increase in the Avicel degradation activity was observed at temperatures of 70° C. or higher. This indicates that the calcium ions contribute to the thermostability of CBM.

Based on these results it is clear that by adding CBM to the thermostable cellobiohydrolase according to the present invention, the hydrolysis activity relative to crystalline cellulose can be increased, at least in the presence of calcium ions.

INDUSTRIAL APPLICABILITY

The thermostable cellobiohydrolase according to the present invention has cellobiohydrolase activity at least at a temperature of 75° C. and a pH of 5.5, and thus is suitable for the hydrolysis process of a cellulose-containing biomass under a high temperature condition of 75° C. or higher. For this reason, the thermostable cellobiohydrolase, a polynucleotide used for the production thereof, an expression vector incorporated with the polynucleotide, and a transformant introduced with the expression vector, are applicable, for example, to the field of energy production from a cellulose-containing biomass.

---

SEQUENCE LISTING

```
<160> NUMBER OF SEQ ID NOS: 20

<210> SEQ ID NO 1
<211> LENGTH: 427
<212> TYPE: PRT
<213> ORGANISM: Unknown
<220> FEATURE:
<223> OTHER INFORMATION: Amino acid sequence of AR19G-166-RA; obtained
      from genome DNA of microbial groups from high temperature hot
      spring soils collected from five locations in Japan; has homology
      with an amino acid sequence of a glycoside hydrolase belonging to
      GH6 family

<400> SEQUENCE: 1

Leu Asp Asn Pro Phe Ile Gly Ala Ile Gly Tyr Val Asn Pro Asp Trp
 1               5                  10                  15

Ala Thr Asn Val Ile Ser Gln Ala Asn Gln Thr Ala Asp Pro Thr Leu
            20                  25                  30

Ala Ala Gln Met Arg Lys Val Ala Thr Tyr Ser Thr Ala Val Trp Leu
        35                  40                  45

Asp Arg Ile Ala Ala Ile Thr Ala Gly Arg Gly Leu Arg Gly His Leu
    50                  55                  60

Asp Glu Ala Leu Arg Gln Met Gln Gln Ala Gly Gln Pro Val Val Ile
65                  70                  75                  80

Thr Leu Val Ile Tyr Asp Leu Pro Asn Arg Asp Cys Ser Ala Ala Ala
                85                  90                  95

Ser Asn Gly Glu Leu Leu Val Ala Gln Asn Gly Leu Ala Arg Tyr Lys
            100                 105                 110

Ala Glu Phe Ile Asp Pro Ile Val Ala Ile Leu Ser Asp Pro Arg Tyr
        115                 120                 125

Ala Gly Leu Arg Ile Val Thr Ile Ile Glu Pro Asp Ser Leu Pro Asn
    130                 135                 140

Leu Val Thr Asn Leu Ser Ile Pro Ala Cys Ala Glu Ala Gln Asn Ala
145                 150                 155                 160

Tyr Ile Glu Gly Ile Arg Tyr Ala Val Asn Arg Leu Arg Thr Ile Pro
                165                 170                 175

Asn Val Tyr Ile Tyr Leu Asp Ile Ala His Ser Gly Trp Leu Gly Trp
            180                 185                 190

Asp Asn Asn Phe Asn Gly Ala Val Asn Leu Tyr Thr Gln Val Val Gln
        195                 200                 205

Gly Met Asp Gln Gly Phe Asn Ser Ile Asp Gly Phe Ile Thr Asn Val
    210                 215                 220

Ala Asn Tyr Thr Pro Leu Glu Glu Pro Tyr Leu Pro Asp Pro Asn Leu
225                 230                 235                 240

Thr Ile Ala Gly Gln Pro Val Arg Ser Ala Ser Phe Tyr Glu Trp Asn
                245                 250                 255

Pro Tyr Phe Asp Glu Leu Asp Tyr Ala Leu Ala Leu Arg Asn Ala Phe
            260                 265                 270
```

```
Ile Gly Arg Gly Phe Pro Ser Thr Ile Gly Met Leu Ile Asp Thr Ser
            275                 280                 285

Arg Asn Gly Trp Gly Cys Ser Tyr Gly Arg Cys Arg Pro Thr Gly
        290                 295                 300

Pro Ser Ser Asp Thr Ser Ser Val Asn Ala Tyr Val Asp Gly Ser Arg
305                 310                 315                 320

Val Asp Arg Arg Tyr His Arg Gly Asn Trp Cys Asn Gln Ala Gly Gly
                325                 330                 335

Ile Gly Glu Arg Pro Gln Ala Ala Pro Arg Ser Gly Ile Asp Ala Tyr
            340                 345                 350

Val Trp Val Lys Pro Pro Gly Glu Ser Asp Gly Val Ser Gln Pro Gly
        355                 360                 365

Ile Val Asp Pro Asp Pro Asn Lys Lys Phe Asp Pro Met Cys Asp
            370                 375                 380

Pro Asn Gly Gln Ser Arg Tyr Asn Ser Ala Tyr Pro Thr Gly Ala Leu
385                 390                 395                 400

Pro Asn Ala Pro His Ala Gly Arg Trp Phe Gln Gln Phe Glu Ile
                405                 410                 415

Leu Val Arg Asn Ala Tyr Pro Pro Ile Gln Pro
            420                 425
```

<210> SEQ ID NO 2
<211> LENGTH: 1284
<212> TYPE: DNA
<213> ORGANISM: Unknown
<220> FEATURE:
<223> OTHER INFORMATION: Nucleotide sequence of AR19G-166-RA; present in natural; obtained from genome DNA of microbial groups from high temperature hot spring soils collected from five locations in Japan

<400> SEQUENCE: 2

```
ttggacaatc cattcatcgg agccatcgga tacgtgaatc cggactgggc aaccaatgtg    60
atcagccaag cgaaccaaac ggctgatcca accttggcgg ctcaaatgcg taaggtggcc   120
acctactcca cagctgtctg gttggatcgt atcgccgcca tcaccgctgg ccgcggattg   180
cgcgggcatt tggatgaagc actacgccaa atgcagcaag ctggccagcc ggttgtgatc   240
acccttgtga tctatgatct gccaaatcga gattgctctg ctgctgcctc caatggcgaa   300
ttactggtcg cccagaatgg actggcccgc tacaaagcgg agttcatcga tcccatcgta   360
gccattctct cagatccccg atatgccggg ctacgcatcg tcaccatcat cgaaccggac   420
tccttaccca acctggtcac gaacctcagc atcccggcat gcgcagaagc tcagaatgca   480
tatatcgaag ggatccgcta tgcggtgaac cggctgcgga caattcccaa cgtctacatc   540
tatctggata tcgcccactc aggctggttg gctgggata taactttaa tggggcagta   600 aatctctaca cccaagttgt gcaaggaatg gatcaagggt ttaacagtat cgatggattc   660
atcaccaacg ttgccaacta tacccccctc gaagaaccct atttgcccga tcccaacctg   720
accatcgctg gcaacccgt tcgctctgcc agcttctacg aatggaaccc ctactttgat   780
gagctggatt acgctctggc tctgcgcaac gctttatcg gacgaggctt ccccagcacc   840
attgggatgc tcatcgatac cagccgaaac gggtggggcg atgcagcta tgggcgatgc   900 aggcccacgg gtcccagttc agataccagc agcgtgaatg cctacgtgga cggctcgcga   960
gtagaccgac gctatcatcg gggcaactgg tgtaaccagg cgggtgggat cggcgagcgc  1020
cctcaggccg caccgcggtc cggtatcgac gcctacgtgt gggtgaaacc acctggggag  1080
```

-continued

```
tccgatgggg tcagccaacc cgggatcgtc gatcccgacg atcccaacaa gaagttcgat    1140
cctatgtgtg atcccaacgg acagagccgg tataactccg catacccaac tggggctctg    1200
cccaacgcgc ccacgctggg cggtggttc ccgcagcagt tcgaaatcct ggtgcggaac     1260
gcctatccgc cgatccaacc ctaa                                           1284
```

<210> SEQ ID NO 3
<211> LENGTH: 427
<212> TYPE: PRT
<213> ORGANISM: Unknown
<220> FEATURE:
<223> OTHER INFORMATION: Amino acid sequence of AR19G-166-QV; obtained
      from genome DNA of microbial groups from high temperature hot
      spring soils collected from five locations in Japan; has homology
      with an amino acid sequence of a glycoside hydrolase belonging to
      GH6 family

<400> SEQUENCE: 3

```
Leu Asp Asn Pro Phe Ile Gly Ala Ile Gly Tyr Val Asn Pro Asp Trp
  1               5                  10                  15

Ala Thr Asn Val Ile Ser Gln Ala Asn Gln Thr Ala Asp Pro Thr Leu
                 20                  25                  30

Ala Ala Gln Met Arg Lys Val Ala Thr Tyr Ser Thr Ala Val Trp Leu
             35                  40                  45

Asp Arg Ile Ala Ala Ile Thr Ala Gly Arg Gly Leu Arg Gly His Leu
         50                  55                  60

Asp Glu Ala Leu Arg Gln Met Gln Gln Ala Gly Gln Pro Val Val Ile
 65                  70                  75                  80

Thr Leu Val Ile Tyr Asp Leu Pro Asn Arg Asp Cys Ser Ala Ala Ala
                 85                  90                  95

Ser Asn Gly Glu Leu Leu Val Ala Gln Asn Gly Leu Ala Arg Tyr Lys
            100                 105                 110

Ala Glu Phe Ile Asp Pro Ile Val Ala Ile Leu Ser Asp Pro Arg Tyr
        115                 120                 125

Ala Gly Leu Arg Ile Val Thr Ile Ile Glu Pro Asp Ser Leu Pro Asn
    130                 135                 140

Leu Val Thr Asn Leu Ser Ile Pro Ala Cys Ala Glu Ala Gln Asn Ala
145                 150                 155                 160

Tyr Ile Glu Gly Ile Arg Tyr Ala Val Asn Arg Leu Arg Thr Ile Pro
                165                 170                 175

Asn Val Tyr Ile Tyr Leu Asp Ile Ala His Ser Gly Trp Leu Gly Trp
            180                 185                 190

Asp Asn Asn Phe Asn Gly Ala Val Asn Leu Tyr Thr Gln Val Val Gln
        195                 200                 205

Gly Met Asp Gln Gly Phe Asn Ser Ile Asp Gly Phe Ile Thr Asn Val
    210                 215                 220

Ala Asn Tyr Thr Pro Leu Glu Glu Pro Tyr Leu Pro Asp Pro Asn Leu
225                 230                 235                 240

Thr Ile Ala Gly Gln Pro Val Arg Ser Ala Ser Phe Tyr Glu Trp Asn
                245                 250                 255

Pro Tyr Phe Asp Glu Leu Asp Tyr Ala Leu Ala Leu Arg Asn Ala Phe
            260                 265                 270

Ile Gly Arg Gly Phe Pro Ser Thr Ile Gly Met Leu Ile Asp Thr Ser
        275                 280                 285

Arg Asn Gly Trp Gly Gly Cys Ser Tyr Gly Gln Cys Arg Pro Thr Gly
    290                 295                 300
```

```
Pro Ser Ser Asp Thr Ser Ser Val Asn Ala Tyr Val Asp Gly Ser Arg
305                 310                 315                 320

Val Asp Arg Arg Tyr His Arg Gly Asn Trp Cys Asn Gln Ala Gly Gly
                325                 330                 335

Ile Gly Glu Arg Pro Gln Ala Ala Pro Arg Ser Gly Ile Asp Val Tyr
            340                 345                 350

Val Trp Val Lys Pro Pro Gly Glu Ser Asp Gly Val Ser Gln Pro Gly
        355                 360                 365

Ile Val Asp Pro Asp Pro Asn Lys Lys Phe Asp Pro Met Cys Asp
    370                 375                 380

Pro Asn Gly Gln Ser Arg Tyr Asn Ser Ala Tyr Pro Thr Gly Ala Leu
385                 390                 395                 400

Pro Asn Ala Pro His Ala Gly Arg Trp Phe Pro Gln Gln Phe Glu Ile
                405                 410                 415

Leu Val Arg Asn Ala Tyr Pro Pro Ile Gln Pro
            420                 425
```

<210> SEQ ID NO 4
<211> LENGTH: 1284
<212> TYPE: DNA
<213> ORGANISM: Unknown
<220> FEATURE:
<223> OTHER INFORMATION: Nucleotide sequence of AR19G-166-QV; obtained
      from genome DNA of microbial groups from high temperature hot
      spring soils collected from five locations in Japan; has homology
      with an amino acid sequence of a glycoside hydrolase belonging to
      GH6 family

<400> SEQUENCE: 4

```
ttggacaatc cattcatcgg agccatcgga tacgtgaatc cggactgggc aaccaatgtg      60
atcagccaag cgaaccaaac ggctgatcca accttggcgg ctcaaatgcg taaggtggcc     120
acctactcca cagctgtctg gttggatcgt atcgccgcca tcaccgctgg ccgcggattg     180
cgcgggcatt tggatgaagc actacgccaa atgcagcaag ctggccagcc ggttgtgatc     240
acccttgtga tctatgatct gccaaatcga gattgctctg ctgctgcctc caatggcgaa     300
ttactggtcg cccagaatgg actggcccgc tacaaagcgg agttcatcga tcccatcgta     360
gccattctct cagatccccg atatgccggg ctacgcatcg tcaccatcat cgaaccggac     420
tccttaccca acctggtcac gaacctcagc atcccggcat gcgcagaagc tcagaatgca     480
tatatcgaag ggatccgcta tgcggtgaac cggctgcgga caattcccaa cgtctacatc     540
tatctggata tcgcccactc aggctggttg ggctgggata taactttaa tggggcagta     600 aatctctaca cccaagttgt gcaaggaatg gatcaagggt ttaacagtat cgatggattc     660
atcaccaacg ttgccaacta tacccccctc gaagaaccct atttgcccga tcccaacctg     720
accatcgctg gcaacccgt tcgctctgcc agcttctacg aatggaaccc ctactttgat     780
gagctggatt acgctctggc tctgcgcaac gcttttatcg gacgaggctt ccccagcacc     840
attgggatgc tcatcgatac cagccgaaac gggtggggcg gatgcagcta tgggcaatgc     900
aggcccacgg gtcccagttc agataccagc agcgtgaatg cctacgtgga cggctcgcga     960
gtagaccgac gctatcatcg gggcaactgg tgtaaccagg cggtgggat cggcgagcgc    1020 cctcaggccg caccgcggtc cggtatcgac gtctacgtgt gggtgaaacc acctggggag    1080
tccgatgggg tcagccaacc cgggatcgtc gatcccgacg atcccaacaa gaagttcgat    1140
cctatgtgtg atcccaacgg acagagccgg tataactccg catacccaac tggggctctg    1200
cccaacgcgc cccacgctgg gcggtggttc ccgcagcagt tcgaaatcct ggtgcggaac    1260
```

```
gcctatccgc cgatccaacc ctaa                                          1284
```

<210> SEQ ID NO 5
<211> LENGTH: 427
<212> TYPE: PRT
<213> ORGANISM: Unknown
<220> FEATURE:
<223> OTHER INFORMATION: Amino acid sequence of AR19G-166-RW; obtained
from genome DNA of microbial groups from high temperature hot
spring soils collected from five locations in Japan; has homology
with an amino acid sequence of a glycoside hydrolase belonging to
GH6 family

<400> SEQUENCE: 5

```
Leu Asp Asn Pro Phe Ile Gly Ala Ile Gly Tyr Val Asn Pro Asp Trp
 1               5                  10                  15

Ala Thr Asn Val Ile Ser Gln Ala Asn Gln Thr Ala Asp Pro Thr Leu
            20                  25                  30

Ala Ala Gln Met Arg Lys Val Ala Thr Tyr Ser Thr Ala Val Trp Leu
        35                  40                  45

Asp Arg Ile Ala Ala Ile Thr Ala Gly Arg Gly Leu Arg Gly His Leu
    50                  55                  60

Asp Glu Ala Leu Arg Gln Met Gln Gln Ala Gly Gln Pro Val Val Ile
 65                  70                  75                  80

Thr Leu Val Ile Tyr Asp Leu Pro Asn Arg Asp Cys Ser Ala Ala Ala
                 85                  90                  95

Ser Asn Gly Glu Leu Leu Val Ala Gln Asn Gly Leu Ala Arg Tyr Lys
            100                 105                 110

Ala Glu Phe Ile Asp Pro Ile Val Ala Ile Leu Ser Asp Pro Arg Tyr
        115                 120                 125

Ala Gly Leu Arg Ile Val Thr Ile Ile Glu Pro Asp Ser Leu Pro Asn
    130                 135                 140

Leu Val Thr Asn Leu Ser Ile Pro Ala Cys Ala Glu Ala Gln Asn Ala
145                 150                 155                 160

Tyr Ile Glu Gly Ile Arg Tyr Ala Val Asn Arg Leu Arg Thr Ile Pro
                165                 170                 175

Asn Val Tyr Ile Tyr Leu Asp Ile Ala His Ser Gly Trp Leu Gly Trp
            180                 185                 190

Asp Asn Asn Phe Asn Gly Ala Val Asn Leu Tyr Thr Gln Val Val Gln
        195                 200                 205

Gly Met Asp Gln Gly Phe Asn Ser Ile Asp Gly Phe Ile Thr Asn Val
    210                 215                 220

Ala Asn Tyr Thr Pro Leu Glu Glu Pro Tyr Leu Pro Asp Pro Asn Leu
225                 230                 235                 240

Thr Ile Ala Gly Gln Pro Val Arg Ser Ala Ser Phe Tyr Glu Trp Asn
                245                 250                 255

Pro Tyr Phe Asp Glu Leu Asp Tyr Ala Leu Ala Leu Arg Asn Ala Phe
            260                 265                 270

Ile Gly Arg Gly Phe Pro Ser Thr Ile Gly Met Leu Ile Asp Thr Ser
        275                 280                 285

Arg Asn Gly Trp Gly Gly Cys Ser Tyr Gly Arg Cys Arg Pro Thr Gly
    290                 295                 300

Pro Ser Ser Asp Thr Ser Ser Val Asn Ala Tyr Val Asp Gly Ser Arg
305                 310                 315                 320

Val Asp Arg Arg Tyr His Arg Gly Asn Trp Cys Asn Gln Ala Gly Gly
                325                 330                 335
```

Ile Gly Glu Arg Pro Gln Ala Ala Pro Arg Ser Gly Ile Asp Trp Tyr
                340                 345                 350

Val Trp Val Lys Pro Pro Gly Glu Ser Asp Gly Val Ser Gln Pro Gly
            355                 360                 365

Ile Val Asp Pro Asp Pro Asn Lys Lys Phe Asp Pro Met Cys Asp
370                 375                 380

Pro Asn Gly Gln Ser Arg Tyr Asn Ser Ala Tyr Pro Thr Gly Ala Leu
385                 390                 395                 400

Pro Asn Ala Pro His Ala Gly Arg Trp Phe Pro Gln Gln Phe Glu Ile
                405                 410                 415

Leu Val Arg Asn Ala Tyr Pro Pro Ile Gln Pro
            420                 425

<210> SEQ ID NO 6
<211> LENGTH: 1284
<212> TYPE: DNA
<213> ORGANISM: Unknown
<220> FEATURE:
<223> OTHER INFORMATION: Nucleotide sequence of AR19G-166-RW; present
      in natural; obtained from genome DNA of microbial groups from high
      temperature hot spring soils collected from five locations in
      Japan

<400> SEQUENCE: 6
ttggacaatc cattcatcgg agccatcgga tacgtgaatc cggactgggc aaccaatgtg      60
atcagccaag cgaaccaaac ggctgatcca accttggcgg ctcaaatgcg taaggtggcc     120
acctactcca cagctgtctg gttggatcgt atcgccgcca tcaccgctgg ccgcggattg     180
cgcgggcatt tggatgaagc actacgccaa atgcagcaag ctggccagcc ggttgtgatc     240
acccttgtga tctatgatct gccaaatcga gattgctctg ctgctgcctc caatggcgaa     300
ttactggtcg cccagaatgg actggcccgc tacaaagcgg agttcatcga tcccatcgta     360
gccattctct cagatccccg atatgccggg ctacgcatcg tcaccatcat cgaaccggac     420
tccttaccca acctggtcac gaacctcagc atcccggcat gcgcagaagc tcagaatgca     480
tatatcgaag ggatccgcta tgcggtgaac cggctgcgga caattcccaa cgtctacatc     540
tatctggata tcgcccactc aggctggttg ggctgggata taactttaa tggggcagta      600 aatctctaca cccaagttgt gcaaggaatg atcaagggt taacagtat cgatggattc       660 atcaccaacg ttgccaacta tacccccctc gaagaaccct atttgcccga tcccaacctg     720
accatcgctg gcaacccgt tcgctctgcc agcttctacg aatggaaccc ctactttgat      780
gagctggatt acgctctggc tctgcgcaac gcttttatcg acgaggctt ccccagcacc      840 attgggatgc tcatcgatac cagccgaaac gggtggggcg gatgcagcta tgggcgatgc     900
aggcccacgg gtcccagttc agataccagc agcgtgaatg cctacgtgga cggctcgcga     960
gtagaccgac gctatcatcg gggcaactgg tgtaaccagg cggtgggat cggcgagcgc     1020 cctcaggccg caccgcggtc cggtatcgac tggtacgtgt gggtgaaacc acctggggag    1080
tccgatgggg tcagccaacc cgggatcgtc gatcccgacg atcccaacaa gaagttcgat    1140
cctatgtgtg atcccaacgg acagagccgg tataactccg cataccccaac tggggctctg    1200 cccaacgcgc ccacgctggc ggtggttc ccgcagcagt tcgaaatcct ggtgcggaac       1260
gcctatccgc cgatccaacc ctaa                                           1284

<210> SEQ ID NO 7
<211> LENGTH: 427

<212> TYPE: PRT
<213> ORGANISM: Unknown
<220> FEATURE:
<223> OTHER INFORMATION: Amino acid sequence of AR19G-166-QW; obtained
      from genome DNA of microbial groups from high temperature hot
      spring soils collected from five locations in Japan; has homology
      with an amino acid sequence of a glycoside hydrolase belonging to
      GH6 family

<400> SEQUENCE: 7

```
Leu Asp Asn Pro Phe Ile Gly Ala Ile Gly Tyr Val Asn Pro Asp Trp
 1               5                  10                  15

Ala Thr Asn Val Ile Ser Gln Ala Asn Gln Thr Ala Asp Pro Thr Leu
            20                  25                  30

Ala Ala Gln Met Arg Lys Val Ala Thr Tyr Ser Thr Ala Val Trp Leu
        35                  40                  45

Asp Arg Ile Ala Ala Ile Thr Ala Gly Arg Gly Leu Arg Gly His Leu
 50                  55                  60

Asp Glu Ala Leu Arg Gln Met Gln Gln Ala Gly Gln Pro Val Val Ile
 65                  70                  75                  80

Thr Leu Val Ile Tyr Asp Leu Pro Asn Arg Asp Cys Ser Ala Ala Ala
            85                  90                  95

Ser Asn Gly Glu Leu Leu Val Ala Gln Asn Gly Leu Ala Arg Tyr Lys
            100                 105                 110

Ala Glu Phe Ile Asp Pro Ile Val Ala Ile Leu Ser Asp Pro Arg Tyr
        115                 120                 125

Ala Gly Leu Arg Ile Val Thr Ile Ile Glu Pro Asp Ser Leu Pro Asn
    130                 135                 140

Leu Val Thr Asn Leu Ser Ile Pro Ala Cys Ala Glu Ala Gln Asn Ala
145                 150                 155                 160

Tyr Ile Glu Gly Ile Arg Tyr Ala Val Asn Arg Leu Arg Thr Ile Pro
                165                 170                 175

Asn Val Tyr Ile Tyr Leu Asp Ile Ala His Ser Gly Trp Leu Gly Trp
            180                 185                 190

Asp Asn Asn Phe Asn Gly Ala Val Asn Leu Tyr Thr Gln Val Val Gln
        195                 200                 205

Gly Met Asp Gln Gly Phe Asn Ser Ile Asp Gly Phe Ile Thr Asn Val
    210                 215                 220

Ala Asn Tyr Thr Pro Leu Glu Glu Pro Tyr Leu Pro Asp Pro Asn Leu
225                 230                 235                 240

Thr Ile Ala Gly Gln Pro Val Arg Ser Ala Ser Phe Tyr Glu Trp Asn
                245                 250                 255

Pro Tyr Phe Asp Glu Leu Asp Tyr Ala Leu Ala Leu Arg Asn Ala Phe
            260                 265                 270

Ile Gly Arg Gly Phe Pro Ser Thr Ile Gly Met Leu Ile Asp Thr Ser
        275                 280                 285

Arg Asn Gly Trp Gly Gly Cys Ser Tyr Gly Gln Cys Arg Pro Thr Gly
    290                 295                 300

Pro Ser Ser Asp Thr Ser Ser Val Asn Ala Tyr Val Asp Gly Ser Arg
305                 310                 315                 320

Val Asp Arg Arg Tyr His Arg Gly Asn Trp Cys Asn Gln Ala Gly Gly
                325                 330                 335

Ile Gly Glu Arg Pro Gln Ala Ala Pro Arg Ser Gly Ile Asp Trp Tyr
        340                 345                 350

Val Trp Val Lys Pro Pro Gly Glu Ser Asp Gly Val Ser Gln Pro Gly
    355                 360                 365
```

Ile Val Asp Pro Asp Pro Asn Lys Lys Phe Asp Pro Met Cys Asp
        370                 375                 380

Pro Asn Gly Gln Ser Arg Tyr Asn Ser Ala Tyr Pro Thr Gly Ala Leu
385                 390                 395                 400

Pro Asn Ala Pro His Ala Gly Arg Trp Phe Pro Gln Gln Phe Glu Ile
                405                 410                 415

Leu Val Arg Asn Ala Tyr Pro Pro Ile Gln Pro
        420                 425

<210> SEQ ID NO 8
<211> LENGTH: 1284
<212> TYPE: DNA
<213> ORGANISM: Unknown
<220> FEATURE:
<223> OTHER INFORMATION: Nucleotide sequence of AR19G-166-QW; present
      in natural; obtained from genome DNA of microbial groups from high
      temperature hot spring soils collected from five locations in
      Japan

<400> SEQUENCE: 8
ttggacaatc cattcatcgg agccatcgga tacgtgaatc cggactgggc aaccaatgtg      60
atcagccaag cgaaccaaac ggctgatcca accttggcgg ctcaaatgcg taaggtggcc     120
acctactcca cagctgtctg gttggatcgt atcgccgcca tcaccgctgg ccgcggattg     180
cgcgggcatt tggatgaagc actacgccaa atgcagcaag ctggccagcc ggttgtgatc     240
acccttgtga tctatgatct gccaaatcga gattgctctg ctgctgcctc caatggcgaa     300
ttactggtcg cccagaatgg actggcccgc tacaaagcgg agttcatcga tcccatcgta     360
gccattctct cagatccccg atatgccggg ctacgcatcg tcaccatcat cgaaccggac     420
tccttaccca acctggtcac gaacctcagc atcccggcat gcgcagaagc tcagaatgca     480
tatatcgaag ggatccgcta tgcggtgaac cggctgcgga caattcccaa cgtctacatc     540
tatctggata tcgcccactc aggctggttg ggctgggata taactttaa tggggcagta     600 aatctctaca cccaagttgt gcaaggaatg gatcaagggt ttaacagtat cgatggattc     660
atcaccaacg ttgccaacta taccccctc gaagaaccct atttgcccga tcccaacctg     720
accatcgctg gcaacccgt tcgctctgcc agcttctacg aatggaaccc ctactttgat     780
gagctggatt acgctctggc tctgcgcaac gcttttatcg gacgaggctt ccccagcacc     840
attgggatgc tcatcgatac cagccgaaac gggtggggcg gatgcagcta tgggcaatgc     900
aggcccacgg gtcccagttc agataccagc agcgtgaatg cctacgtgga cggctcgcga     960
gtagaccgac gctatcatcg gggcaactgg tgtaaccagg cgggtgggat cggcgagcgc    1020
cctcaggccg caccgcggtc cggtatcgac tggtacgtgt gggtgaaacc acctggggag    1080
tccgatgggg tcagccaacc cgggatcgtc gatcccgacg atcccaacaa gaagttcgat    1140
cctatgtgtg atcccaacgg acagagccgg tataactccg catacccaac tggggctctg    1200
cccaacgcgc cccacgctgg gcggtggttc ccgcagcagt tcgaaatcct ggtgcggaac    1260
gcctatccgc cgatccaacc ctaa                                            1284

<210> SEQ ID NO 9
<211> LENGTH: 474
<212> TYPE: PRT
<213> ORGANISM: Unknown
<220> FEATURE:
<223> OTHER INFORMATION: Amino acid sequence of AR19G-166; obtained from
      genome DNA of microbial groups from high temperature hot spring
      soils collected from five locations in Japan; has homology with an amino acid sequence of a glycoside hydrolase belonging to GH6
family

<400> SEQUENCE: 9

```
Pro Thr Arg Thr Pro Thr Pro Ala Ala Pro Thr Ala Thr Pro Thr Pro
  1               5                  10                  15

Val Ala Pro Thr Ala Thr Pro Thr Arg Thr Pro Thr Pro Thr Leu Thr
                 20                  25                  30

Ser Thr Pro Gly Pro Thr Pro Thr Pro Pro Ser Gly Thr His Leu
             35                  40                  45

Asp Asn Pro Phe Ile Gly Ala Ile Gly Tyr Val Asn Pro Asp Trp Ala
         50                  55                  60

Thr Asn Val Ile Ser Gln Ala Asn Gln Thr Ala Asp Pro Thr Leu Ala
 65                  70                  75                  80

Ala Gln Met Arg Lys Val Ala Thr Tyr Ser Thr Ala Val Trp Leu Asp
                 85                  90                  95

Arg Ile Ala Ala Ile Thr Ala Gly Arg Gly Leu Arg Gly His Leu Asp
                100                 105                 110

Glu Ala Leu Arg Gln Met Gln Gln Ala Gly Gln Pro Val Val Ile Thr
                115                 120                 125

Leu Val Ile Tyr Asp Leu Pro Asn Arg Asp Cys Ser Ala Ala Ala Ser
            130                 135                 140

Asn Gly Glu Leu Leu Val Ala Gln Asn Gly Leu Ala Arg Tyr Lys Ala
145                 150                 155                 160

Glu Phe Ile Asp Pro Ile Val Ala Ile Leu Ser Asp Pro Arg Tyr Ala
                165                 170                 175

Gly Leu Arg Ile Val Thr Ile Ile Glu Pro Asp Ser Leu Pro Asn Leu
                180                 185                 190

Val Thr Asn Leu Ser Ile Pro Ala Cys Ala Glu Ala Gln Asn Ala Tyr
            195                 200                 205

Ile Glu Gly Ile Arg Tyr Ala Val Asn Arg Leu Arg Thr Ile Pro Asn
    210                 215                 220

Val Tyr Ile Tyr Leu Asp Ile Ala His Ser Gly Trp Leu Gly Trp Asp
225                 230                 235                 240

Asn Asn Phe Asn Gly Ala Val Asn Leu Tyr Thr Gln Val Val Gln Gly
                245                 250                 255

Met Asp Gln Gly Phe Asn Ser Ile Asp Gly Phe Ile Thr Asn Val Ala
            260                 265                 270

Asn Tyr Thr Pro Leu Glu Glu Pro Tyr Leu Pro Asp Pro Asn Leu Thr
    275                 280                 285

Ile Ala Gly Gln Pro Val Arg Ser Ala Ser Phe Tyr Glu Trp Asn Pro
290                 295                 300

Tyr Phe Asp Glu Leu Asp Tyr Ala Leu Ala Leu Arg Asn Ala Phe Ile
305                 310                 315                 320

Gly Arg Gly Phe Pro Ser Thr Ile Gly Met Leu Ile Asp Thr Ser Arg
                325                 330                 335

Asn Gly Trp Gly Gly Cys Ser Tyr Gly Gln Cys Arg Pro Thr Gly Pro
                340                 345                 350

Ser Ser Asp Thr Ser Ser Val Asn Ala Tyr Val Asp Gly Ser Arg Val
            355                 360                 365

Asp Arg Arg Tyr His Arg Gly Asn Trp Cys Asn Gln Ala Gly Gly Ile
    370                 375                 380

Gly Glu Arg Pro Gln Ala Ala Pro Arg Ser Gly Ile Asp Ala Tyr Val
385                 390                 395                 400
```

Trp Val Lys Pro Pro Gly Glu Ser Asp Gly Val Ser Gln Pro Gly Ile
                405                 410                 415

Val Asp Pro Asp Asp Pro Asn Lys Lys Phe Asp Pro Met Cys Asp Pro
            420                 425                 430

Asn Gly Gln Ser Arg Tyr Asn Ser Ala Tyr Pro Thr Gly Ala Leu Pro
        435                 440                 445

Asn Ala Pro His Ala Gly Arg Trp Phe Pro Gln Gln Phe Glu Ile Leu
    450                 455                 460

Val Arg Asn Ala Tyr Pro Pro Ile Gln Pro
465                 470

<210> SEQ ID NO 10
<211> LENGTH: 459
<212> TYPE: PRT
<213> ORGANISM: Unknown
<220> FEATURE:
<223> OTHER INFORMATION: Amino acid sequence encoded by an open reading
      frame AR19G-12; obtained from genome DNA of microbial groups from
      high temperature hot spring soils collected from five locations in
      Japan; has homology with an amino acid sequence of a glycoside
      hydrolase belonging to GH6 family

<400> SEQUENCE: 10

Thr Ala Thr Pro Thr Arg Thr Pro Thr Pro Pro Ala Gln Pro Thr Ala
  1               5                  10                  15

Thr Pro Thr Arg Thr Pro Thr Pro Thr Ala Val Ala Pro Thr Pro Val
                 20                  25                  30

Pro Gly Val His Leu Asp Asn Pro Phe Val Gly Ala Val Trp Tyr Val
             35                  40                  45

Asn Pro Asp Trp Ala Ala Asn Val Leu Asn Gln Ala Gln Gln Thr Gly
 50                  55                  60

Gly Thr Leu Gly Gln Arg Met Ala Ala Val Ala Gln Tyr Ser Thr Ala
 65                  70                  75                  80

Val Trp Leu Asp Arg Ile Gly Ala Ile Thr Glu Gly Arg Gly Leu Gln
                 85                  90                  95

Gly His Leu Asn Glu Ala Leu Ala Gln Gly Ala Asn Leu Ile Met Ile
            100                 105                 110

Val Ile Tyr Asp Leu Pro Asn Arg Asp Cys Ala Ala Tyr Ala Ser Asn
        115                 120                 125

Gly Glu Leu Leu Ile Ala Glu Asn Gly Leu Glu Arg Tyr Lys Arg Glu
    130                 135                 140

Tyr Ile Asp Val Ile Tyr Asn Ile Leu Ala Gln Pro Gln Tyr Arg Asn
145                 150                 155                 160

Leu Arg Ile Val Ala Val Ile Glu Pro Asp Ser Leu Pro Asn Leu Val
                165                 170                 175

Thr Asn Leu Ser Glu Pro Ala Cys Ala Glu Ala Asn Ser Thr Gly Ala
            180                 185                 190

Tyr Val Glu Gly Ile Arg Tyr Ala Val Asn Lys Leu His Gln Leu Pro
        195                 200                 205

Asn Val Tyr Ile Tyr Leu Asp Ile Ala His Ser Gly Trp Leu Gly Trp
    210                 215                 220

Asp Asn Asn Phe Gln Gly Ala Val Asn Leu Tyr Thr Gln Val Val Gln
225                 230                 235                 240

Gly Met Ala Asp Gly Phe Asn Ser Ile Asp Gly Phe Val Thr Asn Thr
                245                 250                 255

Ala Asn Tyr Thr Pro Val Glu Glu Pro Tyr Leu Pro Asp Pro Asn Leu

```
                260               265                270
Thr Ile Gly Gly Gln Pro Val Arg Ser Ala Asn Phe Tyr Glu Trp Asn
            275                 280                 285

Pro Tyr Phe Asp Glu Leu Asp Tyr Ala Gln Ala Leu Arg Gln Ala Phe
        290                 295                 300

Ile Gly Arg Gly Phe Pro Ser Gly Ile Gly Met Leu Ile Asp Thr Ser
305                 310                 315                 320

Arg Asn Gly Trp Gly Ser Ser Tyr Gly Arg Ser Arg Pro Ser Gly
            325                 330                 335

Ala Ser Ser Asn Thr Thr Asn Val Asn Val Tyr Val Asp Glu Ser Arg
            340                 345                 350

Val Asp Arg Arg Tyr His Arg Gly Asn Trp Cys Asn Gln Ala Gly Gly
            355                 360                 365

Ile Gly Glu Arg Pro Arg Ala Asn Pro Ala Ala Gly Ile Asp Ala Tyr
            370                 375                 380

Val Trp Val Lys Pro Pro Gly Glu Ser Asp Gly Val Ser Gln Pro Gly
385                 390                 395                 400

Val Val Asp Pro Val Asp Pro Asn Lys Lys Phe Asp Ile Met Cys Asp
            405                 410                 415

Pro Asn Gly Gln Ser Arg Tyr Asn Ser Ala Tyr Pro Thr Gly Ala Leu
            420                 425                 430

Pro Asn Ala Pro His Ala Gly Arg Trp Phe Pro Glu Gln Phe Glu Ile
            435                 440                 445

Leu Val Gln Asn Ala Tyr Pro Pro Ile Gln Pro
            450                 455
```

<210> SEQ ID NO 11
<211> LENGTH: 548
<212> TYPE: PRT
<213> ORGANISM: Unknown
<220> FEATURE:
<223> OTHER INFORMATION: Amino acid sequence encoded by open reading
    frame OJ1-1; obtained from genome DNA of microbial groups from
    high temperature hot spring soils collected from five locations
    in Japan; is a multi-domain enzyme

<400> SEQUENCE: 11

```
Met Ser Arg Ile Arg Trp Gln Ile Leu Leu Arg Ala Thr Leu Ile Val
  1               5                  10                  15

Ala Ile Ala Ala Ala Val Ala Leu Ile Ser Leu Gln Ala Arg Ala
            20                  25                  30

Gln Ser Thr Leu Lys Val Gln Tyr Arg Cys Ala Asp Thr Asn Ala Thr
            35                  40                  45

Gly Asn Gln Ile Lys Pro His Leu Asn Ile Val Asn Thr Gly Ser Ser
        50                  55                  60

Ala Val Ser Leu Thr Ala Leu Lys Ala Arg Tyr Tyr Thr Ile Asp
 65                 70                  75                  80

Gly Glu Lys Ala Gln Ser Tyr Trp Cys Asp Tyr Ala Thr Ile Gly Cys
                85                  90                  95

Ser Asn Ile Thr Ala Ser Phe Val Lys Met Ala Thr Ala Val Ser Gly
            100                 105                 110

Ala Asp Tyr Tyr Leu Glu Val Gly Phe Thr Ser Gly Thr Leu Asn Ala
            115                 120                 125

Gly Ala Ser Thr Gly Glu Ile Gln Asn Arg Phe Ala Lys Ser Asp Trp
        130                 135                 140

Thr Asn Tyr Thr Gln Thr Gly Asp Tyr Ser Phe Asp Pro Ser Lys Thr
```

```
            145                 150                 155                 160

Ser Phe Ala Asp Trp Asn Lys Val Thr Leu Tyr Asn Asn Gly Thr Leu
                        165                 170                 175

Val Trp Gly Val Glu Pro Ser Gly Ala Ser Ala Pro Thr Asn Thr Ser
                        180                 185                 190

Ala Pro Ala Ala Thr Ala Thr Arg Thr Asn Thr Ala Val Thr Gly Pro
                        195                 200                 205

Thr Asn Thr Ser Ala Pro Ala Ala Thr Ala Arg Thr Asn Thr Pro
                    210                 215                 220

Gly Gly Pro Thr Ala Thr Arg Thr Arg Thr Pro Thr Arg Thr Arg Thr
        225                 230                 235                 240

Pro Thr Arg Thr Ala Thr Gly Gln Val Ala Pro Thr Asn Thr Ala
                        245                 250                 255

Pro Ala Ala Thr Ala Thr Arg Thr Pro Thr Thr Gly Thr Gly Pro Thr
                        260                 265                 270

Ala Thr Arg Thr Asn Thr Thr Val Ala Pro Thr Ala Thr Gly Pro
                    275                 280                 285

Thr Ala Ala Pro Gly Thr His Leu Asp Asn Pro Phe Val Gly Ala Lys
                    290                 295                 300

Trp Tyr Ile Asn Pro Asp Trp Gln Gly Arg Thr Val Leu Asn Tyr Ser
        305                 310                 315                 320

Thr Ala Val Trp Met Asp Arg Ile Ala Ala Val Val Gly Gly Ser Gly
                        325                 330                 335

Val Thr Arg Asn Leu Ala Gly His Leu Asp Ala Ala Leu Ser Gln Gly
                        340                 345                 350

Ala Asn Leu Ile Ile Ile Val Val Tyr Asp Leu Pro Asn Arg Asp Cys
                    355                 360                 365

Phe Ala Leu Ala Ser Asn Gly Glu Leu Lys Ile Ala Glu Asp Gly Phe
                    370                 375                 380

Asn Arg Tyr Lys Asn Glu Tyr Ile Glu Pro Met Ile Ala Thr Leu Asn
        385                 390                 395                 400

Gln Ala Lys Tyr Ala Asn Leu Arg Ile Val Ala Val Ile Glu Pro Asp
                        405                 410                 415

Ser Leu Pro Asn Leu Val Thr Asn Leu Ser Asp Pro Asp Cys Ala Gln
                        420                 425                 430

Ala Asn Gly Thr Gly Tyr Lys Asp Gly Ile Val Tyr Ala Leu Asn
                    435                 440                 445

Arg Leu Asn Thr Met Thr Asn Val Tyr Pro Tyr Ile Asp Ile Ala His
        450                 455                 460

Ser Gly Trp Leu Gly Trp Asp Ser Asn Phe Gly Pro Ala Ala Asp Leu
        465                 470                 475                 480

Phe Ala Asn Val Val Lys Ala Thr Thr Lys Gly Val Asn Ser Val Asp
                        485                 490                 495

Gly Phe Val Ser Asn Thr Ala Asn Tyr Thr Pro Leu Asp Glu Pro Phe
                    500                 505                 510

Leu Thr Asp Pro Asn Leu Thr Val Gly Gly Gln Gln Val Lys Ser Ala
                    515                 520                 525

Ser Phe Tyr Glu Trp Asn Pro Tyr Phe Asp Glu Arg Asp Tyr Val Thr
                    530                 535                 540

Ala Met Arg Asn
        545

<210> SEQ ID NO 12
```

```
<211> LENGTH: 22
<212> TYPE: DNA
<213> ORGANISM: Artificial Sequence
<220> FEATURE:
<223> OTHER INFORMATION: Forward primer; has a nucleotide sequence which
      is homologous with a partial sequence including nucleotides at
      position 1 to 22 of the nucleotide sequence of SEQ ID NO: 2;
      primer for gene cloning

<400> SEQUENCE: 12
ttggacaatc cattcatcgg ag                                            22

<210> SEQ ID NO 13
<211> LENGTH: 22
<212> TYPE: DNA
<213> ORGANISM: Artificial Sequence
<220> FEATURE:
<223> OTHER INFORMATION: Reverse Primer; has a nucleotide sequence which
      is complementary with a partial sequence including nucleotides at
      position 1263 to 1284 of the nucleotide sequence of SEQ ID NO: 2;
      primer for gene cloning

<400> SEQUENCE: 13
ttagggttgg atcggcggat ag                                            22

<210> SEQ ID NO 14
<211> LENGTH: 29
<212> TYPE: DNA
<213> ORGANISM: Artificial Sequence
<220> FEATURE:
<223> OTHER INFORMATION: Forward primer in which 7 nucleotides (CACCATG)
      were added to the 5'-end side of the nucleotide sequence of SEQ ID
      NO: 12; primer for gene cloning

<400> SEQUENCE: 14
caccatgttg gacaatccat tcatcggag                                     29

<210> SEQ ID NO 15
<211> LENGTH: 428
<212> TYPE: PRT
<213> ORGANISM: Herpetosiphon aurantiacus DSM 785
<220> FEATURE:
<223> OTHER INFORMATION: Catalytic domain of glucosid hydrolase family
      6; present in natural; is an amino acid sequence of a glycoside
      hydrolase belonging to GH6 family of mesophilic aerobic bacterium
      in phylum Chloroflexi, Herpetosiphon aurantiacus DSM 785

<400> SEQUENCE: 15

Val Ala Asn Pro Phe Val Gly Ala Gln Gly Tyr Ile Asn Ser Glu Tyr
 1               5                  10                  15

Ala Ala Arg Val Asn Ala Glu Ala Asn Ala Thr Gly Gly Thr Leu Gly
             20                  25                  30

Ser Gln Met Arg Gln Val Ala Ser Tyr Pro Thr Ala Val Trp Leu Asp
         35                  40                  45

Arg Ile Ala Ala Ile Ala Gly Ser Ser Glu Ser Met Gly Leu Arg Ala
     50                  55                  60

His Leu Asp Ala Ala Leu Val Gln Gln Gln Thr Ser Gly Gln Gln Val
 65                  70                  75                  80

Ala Ile Ser Ile Val Val Tyr Asp Leu Pro Asn Arg Asp Cys Ala Ala
                 85                  90                  95

Leu Ala Ser Asn Gly Glu Leu Lys Ile Ser Glu Asn Gly Leu Asn Arg
            100                 105                 110

Tyr Lys Thr Glu Tyr Ile Asp Pro Ile Ala Ala Ile Val Gly Glu Ser
        115                 120                 125
```

```
Lys Tyr Ala Ser Leu Arg Ile Val Val Ile Leu Glu Pro Asp Ser Leu
    130                 135                 140

Ser Asn Leu Val Thr Asn Ala Ser Ile Pro Ala Cys Ala Glu Ala Ile
145                 150                 155                 160

Ser Ser Gly Ala Tyr Val Gln Gly Val Gln Tyr Ala Ile Asn Lys Leu
                165                 170                 175

Asn Val Thr Ser Asn Val Tyr Ile Tyr Met Asp Ile Ala His Ser Gly
            180                 185                 190

Trp Leu Gly Trp Asp Ser Asn Phe Thr Pro Ala Ile Gln Leu Tyr Thr
        195                 200                 205

Gln Thr Val Arg Gly Thr Thr Lys Gly Leu Asn Gly Ile Asp Gly Phe
    210                 215                 220

Ile Ser Asn Thr Ala Asn Tyr Thr Pro Leu Asn Glu Val Phe Leu Pro
225                 230                 235                 240

Asn Ser Gly Leu Thr Leu Gly Gly Asn Pro Ile Arg Ser Ser Leu
                245                 250                 255

Phe Tyr Glu Trp Asn Pro Tyr Phe Asp Glu Thr Asp Tyr Val Leu Ala
                260                 265                 270

Met Arg Asn Ala Phe Ile Thr Ala Gly Phe Pro Ser Gly Ile Gly Met
        275                 280                 285

Leu Ile Asp Thr Ser Arg Asn Gly Trp Gly Gly Thr Ala Arg Pro Thr
    290                 295                 300

Met Val Ser Ser Ser Asn Ser Leu Glu Ile Tyr Val Asn Asp Ser Lys
305                 310                 315                 320

Leu Asp Arg Arg Pro His Arg Gly Gly Trp Cys Asn Gln Ala Gly Ala
                325                 330                 335

Gly Ile Gly Glu Arg Pro Thr Ala Ala Pro Val Ser Gly Ile Asp Ala
                340                 345                 350

Tyr Val Trp Val Lys Pro Pro Gly Glu Ser Asp Gly Val Ala Thr Ala
        355                 360                 365

Gly Val Ile Asp Pro Thr Asp Pro Ala Lys Gln Phe Asp Ala Met Cys
    370                 375                 380

Asp Pro Asn Ala Gln Asn Arg Tyr Asn Thr Ala Tyr Pro Thr Asn Ala
385                 390                 395                 400

Leu Ala Gly Ala Pro His Ala Gly Arg Trp Phe Pro Ser Gln Phe Ala
                405                 410                 415

Met Leu Val Arg Asn Ala Tyr Pro Pro Ile Ser Gln
                420                 425

<210> SEQ ID NO 16
<211> LENGTH: 150
<212> TYPE: PRT
<213> ORGANISM: Caldibacillus cellulovorans
<220> FEATURE:
<223> OTHER INFORMATION: CBM3 of cellobiohydrolase; present in natural;
      an amino acid sequence of a cellulose-binding module CBM3 of a
      cellobiohydrolase of a thermophilic aerobic bacterium
      Caldibacillus cellulovorans

<400> SEQUENCE: 16

Ser Leu Val Val Gln Tyr Arg Ala Ala Asp Thr Asn Ala Gly Asp Asn
  1               5                  10                  15

Gln Leu Lys Pro His Phe Arg Ile Val Asn Arg Gly Thr Ser Ser Val
            20                  25                  30

Pro Leu Ser Glu Leu Thr Ile Arg Tyr Trp Tyr Thr Val Asp Gly Asp
        35                  40                  45
```

```
Lys Pro Gln Val Phe Asn Cys Asp Trp Ala Gln Val Gly Cys Ser Asn
         50                  55                  60

Val Arg Gly Ser Phe Val Lys Leu Ser Thr Gly Arg Thr Gly Ala Asp
 65                  70                  75                  80

Tyr Tyr Ile Glu Ile Thr Phe Thr Ser Gly Ala Gly Ser Leu Ala Ala
                 85                  90                  95

Gly Ala Ser Ser Gly Asp Ile Gln Val Arg Ile Asn Lys Asn Asp Trp
            100                 105                 110

Thr Asn Tyr Asn Glu Ala Asn Asp Tyr Ser Tyr Asp Pro Thr Lys Thr
                115                 120                 125

Ser Phe Ala Asp Trp Asn Arg Val Thr Leu Tyr Arg Asn Gly Gln Leu
        130                 135                 140

Ile Trp Gly Val Glu Pro
145                 150

<210> SEQ ID NO 17
<211> LENGTH: 269
<212> TYPE: PRT
<213> ORGANISM: Unknown
<220> FEATURE:
<223> OTHER INFORMATION: Amino acid sequence encoded by a linker and
      CBM3 sequence of open reading frame OJ1-1; artifically synthesized
      in order to examine an effect of CBM-added on cellulose hydrolysis
      activity of enzyme proteins

<400> SEQUENCE: 17

Ser Gly Ala Ser Ala Pro Thr Asn Thr Ser Ala Pro Ala Ala Thr Ala
  1               5                  10                  15

Thr Arg Thr Asn Thr Ala Val Thr Gly Pro Thr Asn Thr Ser Ala Pro
             20                  25                  30

Ala Ala Thr Ala Thr Arg Thr Asn Thr Pro Gly Gly Pro Thr Ala Thr
             35                  40                  45

Arg Thr Arg Thr Pro Thr Arg Thr Arg Thr Pro Thr Arg Thr Ala Thr
         50                  55                  60

Gly Gln Val Ala Pro Thr Asn Thr Ala Pro Ala Ala Thr Ala Thr
 65                  70                  75                  80

Arg Thr Pro Thr Thr Gly Thr Gly Pro Thr Ala Thr Arg Thr Asn Thr
                 85                  90                  95

Thr Val Ala Pro Thr Ala Thr Thr Gly Pro Thr Ala Ala Pro Gly Thr
            100                 105                 110

His Gln Ser Thr Leu Lys Val Gln Tyr Arg Cys Ala Asp Thr Asn Ala
                115                 120                 125

Thr Gly Asn Gln Ile Lys Pro His Leu Asn Ile Val Asn Thr Gly Ser
        130                 135                 140

Ser Ala Val Ser Leu Thr Ala Leu Lys Ala Arg Tyr Tyr Tyr Thr Ile
145                 150                 155                 160

Asp Gly Glu Lys Ala Gln Ser Tyr Trp Cys Asp Tyr Ala Thr Ile Gly
                165                 170                 175

Cys Ser Asn Ile Thr Ala Ser Phe Val Lys Met Ala Thr Ala Val Ser
                180                 185                 190

Gly Ala Asp Tyr Tyr Leu Glu Val Gly Phe Thr Ser Gly Thr Leu Asn
                195                 200                 205

Ala Gly Ala Ser Thr Gly Glu Ile Gln Asn Arg Phe Ala Lys Ser Asp
            210                 215                 220

Trp Thr Asn Tyr Thr Gln Thr Gly Asp Tyr Ser Phe Asp Pro Ser Lys
225                 230                 235                 240
```

Thr Ser Phe Ala Asp Trp Asn Lys Val Thr Leu Tyr Asn Asn Gly Thr
            245                 250                 255

Leu Val Trp Gly Val Glu Pro Ser Gly Ala Ser Ala Pro
        260                 265

<210> SEQ ID NO 18
<211> LENGTH: 810
<212> TYPE: DNA
<213> ORGANISM: Unknown
<220> FEATURE:
<223> OTHER INFORMATION: Nucleotide sequence of a Linker and CBM3
      sequence of open reading frame OJ1-1; artificially synthesized in
      order to examine an effect of CBM-added on cellulose hydrolysis
      activity of enzyme proteins

<400> SEQUENCE: 18
tccggtgcca gtgcgccgac caatacgtct gccctgctg cgactgcaac gcgcaccaac      60
acagccgtta cgggtccgac caacacgagt gcaccggccg ctacggcaac gcgtacgaac     120
actccgggtg accaaccgc aaccgcacg cgcacgccaa cccggacccg tacgccacg       180 cgcaccgcaa ccggtcaagt cgcaccaacg aataccactg cgccggcagc caccgccacg    240
cgcacaccga caactgggac cggtcctacc gccacacgca ccaacaccac cgttgcacca    300
actgccacga ccggcccgac cgctgcgccc ggcacacacc agtcaacgct gaaagtccag    360
tatcgttgcg ccgataccaa cgcaactggt aaccagatca aaccgcacct gaacattgtc    420
aacaccggta gttctgccgt atcgctcacc gctcttaaag cgcgctacta ctacaccatc    480
gatggcgaga agcgcaatc gtattggtgc gactatgcaa cgattggctg cagcaatatc     540
accgcctcgt tcgtgaaaat ggcgacagca gtaagcggcg ccgactatta cttggaagtg    600
ggctttacca gcggtactct gaatgcaggg gctagtacgg gtgaaatcca gaatcgcttt    660
gcgaaaagcg attggacgaa ctatacgcag acaggcgatt acagcttcga tcccagcaaa    720
accagctttg cagactggaa caaagtaacc ctgtacaaca cggcaccct ggtttggggc     780 gtggaaccaa gtggcgcgag tgctccataa                                     810

<210> SEQ ID NO 19
<211> LENGTH: 697
<212> TYPE: PRT
<213> ORGANISM: Unknown
<220> FEATURE:
<223> OTHER INFORMATION: Amino acid sequence of entire length of
      CBM-added AR19G-166-RA gene optimized for codon usage frequency
      of E. coli; artificially synthesized in order to examine an effect
      of CBM-added on cellulose hydrolysis activity of enzyme proteins

<400> SEQUENCE: 19

Met Leu Asp Asn Pro Phe Ile Gly Ala Ile Gly Tyr Val Asn Pro Asp
 1                5                  10                  15

Trp Ala Thr Asn Val Ile Ser Gln Ala Asn Gln Thr Ala Asp Pro Thr
                20                  25                  30

Leu Ala Ala Gln Met Arg Lys Val Ala Thr Tyr Ser Thr Ala Val Trp
            35                  40                  45

Leu Asp Arg Ile Ala Ala Ile Thr Ala Gly Arg Gly Leu Arg Gly His
        50                  55                  60

Leu Asp Glu Ala Leu Arg Gln Met Gln Gln Ala Gly Gln Pro Val Val
65                  70                  75                  80

Ile Thr Leu Val Ile Tyr Asp Leu Pro Asn Arg Asp Cys Ser Ala Ala
                85                  90                  95

Ala Ser Asn Gly Glu Leu Leu Val Ala Gln Asn Gly Leu Ala Arg Tyr

-continued

```
                100                 105                 110
Lys Ala Glu Phe Ile Asp Pro Ile Val Ala Ile Leu Ser Asp Pro Arg
            115                 120                 125

Tyr Ala Gly Leu Arg Ile Val Thr Ile Ile Glu Pro Asp Ser Leu Pro
        130                 135                 140

Asn Leu Val Thr Asn Leu Ser Ile Pro Ala Cys Ala Glu Ala Gln Asn
145                 150                 155                 160

Ala Tyr Ile Glu Gly Ile Arg Tyr Ala Val Asn Arg Leu Arg Thr Ile
                165                 170                 175

Pro Asn Val Tyr Ile Tyr Leu Asp Ile Ala His Ser Gly Trp Leu Gly
            180                 185                 190

Trp Asp Asn Asn Phe Asn Gly Ala Val Asn Leu Tyr Thr Gln Val Val
        195                 200                 205

Gln Gly Met Asp Gln Gly Phe Asn Ser Ile Asp Gly Phe Ile Thr Asn
    210                 215                 220

Val Ala Asn Tyr Thr Pro Leu Glu Gly Pro Tyr Leu Pro Asp Pro Asn
225                 230                 235                 240

Leu Thr Ile Ala Gly Gln Pro Val Arg Ser Ala Ser Phe Tyr Glu Trp
                245                 250                 255

Asn Pro Tyr Phe Asp Glu Leu Asp Tyr Ala Leu Ala Leu Arg Asn Ala
            260                 265                 270

Phe Ile Gly Arg Gly Phe Pro Ser Thr Ile Gly Met Leu Ile Asp Thr
        275                 280                 285

Ser Arg Asn Gly Trp Gly Gly Cys Ser Tyr Gly Arg Cys Arg Pro Thr
    290                 295                 300

Gly Pro Ser Ser Asp Thr Ser Ser Val Asn Ala Tyr Val Asp Gly Ser
305                 310                 315                 320

Arg Val Asp Arg Arg Tyr His Arg Gly Asn Trp Cys Asn Gln Ala Gly
                325                 330                 335

Gly Ile Gly Glu Arg Pro Gln Ala Ala Pro Arg Ser Gly Ile Asp Ala
        340                 345                 350

Tyr Val Trp Val Lys Pro Pro Gly Glu Ser Asp Gly Val Ser Gln Pro
    355                 360                 365

Gly Ile Val Asp Pro Asp Asp Pro Asn Lys Lys Phe Asp Pro Met Cys
370                 375                 380

Asp Pro Asn Gly Gln Ser Arg Tyr Asn Ser Ala Tyr Pro Thr Gly Ala
385                 390                 395                 400

Leu Pro Asn Ala Pro His Ala Gly Arg Trp Phe Pro Gln Gln Phe Glu
                405                 410                 415

Ile Leu Val Arg Asn Ala Tyr Pro Pro Ile Gln Pro Ser Gly Ala Ser
        420                 425                 430

Ala Pro Thr Asn Thr Ser Ala Pro Ala Ala Thr Ala Arg Thr Asn
    435                 440                 445

Thr Ala Val Thr Gly Pro Thr Asn Thr Ser Ala Pro Ala Ala Thr Ala
450                 455                 460

Thr Arg Thr Asn Thr Pro Gly Gly Pro Thr Ala Thr Arg Thr Arg Thr
465                 470                 475                 480

Pro Thr Arg Thr Arg Thr Pro Thr Arg Thr Ala Thr Gly Gln Val Ala
                485                 490                 495

Pro Thr Asn Thr Thr Ala Pro Ala Ala Thr Ala Arg Thr Pro Thr
        500                 505                 510

Thr Gly Thr Gly Pro Thr Ala Thr Arg Thr Asn Thr Thr Val Ala Pro
    515                 520                 525
```

```
Thr Ala Thr Thr Gly Pro Thr Ala Ala Pro Gly Thr His Gln Ser Thr
    530                 535                 540

Leu Lys Val Gln Tyr Arg Cys Ala Asp Thr Asn Ala Thr Gly Asn Gln
545                 550                 555                 560

Ile Lys Pro His Leu Asn Ile Val Asn Thr Gly Ser Ser Ala Val Ser
                565                 570                 575

Leu Thr Ala Leu Lys Ala Arg Tyr Tyr Tyr Thr Ile Asp Gly Glu Lys
            580                 585                 590

Ala Gln Ser Tyr Trp Cys Asp Tyr Ala Thr Ile Gly Cys Ser Asn Ile
        595                 600                 605

Thr Ala Ser Phe Val Lys Met Ala Thr Ala Val Ser Gly Ala Asp Tyr
    610                 615                 620

Tyr Leu Glu Val Gly Phe Thr Ser Gly Thr Leu Asn Ala Gly Ala Ser
625                 630                 635                 640

Thr Gly Glu Ile Gln Asn Arg Phe Ala Lys Ser Asp Trp Thr Asn Tyr
                645                 650                 655

Thr Gln Thr Gly Asp Tyr Ser Phe Asp Pro Ser Lys Thr Ser Phe Ala
            660                 665                 670

Asp Trp Asn Lys Val Thr Leu Tyr Asn Asn Gly Thr Leu Val Trp Gly
        675                 680                 685

Val Glu Pro Ser Gly Ala Ser Ala Pro
    690                 695
```

<210> SEQ ID NO 20
<211> LENGTH: 2094
<212> TYPE: DNA
<213> ORGANISM: Unknown
<220> FEATURE:
<223> OTHER INFORMATION: Nucleotide sequence of entire length of CBM
      added AR19G-166-RA gene optimized for codon usage frequency of
      E. coli; artificially synthesized in order to examine an effect of
      CBM-added on cellulose hydrolysis activity of enzyme proteins

<400> SEQUENCE: 20

```
atgctggata acccgtttat cggcgcgatt ggctatgtta atccggattg ggcgacaaac      60
gtgatttctc aggcgaatca gacggccgat ccaactctgg cggcccaaat gcgcaaagtg     120
gccacctata gcactgctgt atggcttgat cgtattgcgg caattactgc tggtcgcgga     180
ttgcgcggcc atcttgatga gcattgcgt cagatgcaac aggcgggtca accggttgtg     240
attaccctgg tcatctacga tctgccgaat cgcgattgtt cagcggcggc ctcgaatggt     300
gagttgctgt tgcccaaaa cgggttagct cgctataagg cggaattcat gacccgatc      360
gttgcgattc tgtccgatcc acgctatgct ggtttacgga ttgttaccat catcgaaccg     420
gattcactcc ctaatctggt taccaacctc tcaatccctg cctgtgccga agcacagaac     480
gcatatattg aaggcattcg ttatgccgtg aatcgcctgc gtaccattcc gaatgtgtac     540
atctatctgg atattgcgca tagcgggtgg cttggatggg acaataattt caacggtgcg     600
gtgaacctgt acactcaagt cgtacaggga atggatcagg gcttcaacag catcgatggt     660
tttatcacga atgttgccaa ttatacaccc ttagaagagc cctatctgcc cgatcctaac     720
ctcactattg cgggccaacc ggtccgttct gcttcctttt acgaatggaa tccgtatttt     780
gatgagctgg attacgcgtt agcgttacgg aacgcgttca ttggtcgcgg ctttccgtcc     840
actatcggga tgctgattga caccgtcgc aacgggtggg gaggctgttc ctatggacgg     900
tgccgtccga caggcccctc ctcagacacc tcgtctgtga acgcgtatgt cgatggtagc     960
```

```
cgtgtggatc gccgctatca ccgtgggaat tggtgcaatc aggcgggcgg tattggggaa    1020
cgtcctcaag cagctccgcg ttcggggatt gacgcgtatg tatgggtgaa accaccgggt    1080
gaaagcgacg gtgtctcgca gcctggcatt gtggacccgg acgacccgaa caagaagttt    1140
gaccctatgt gtgatccgaa cggccaatcc cggtacaatt ctgcttaccc gaccggcgcg    1200
ctgccaaatg cgccgcatgc gggccgttgg tttccgcagc agttcgagat cctggtgcgc    1260
aatgcctacc ctccgattca gccgtccggt gccagtgcgc cgaccaatac gtctgcccct    1320
gctgcgactg caacgcgcac caacacagcc gttacgggtc cgaccaacac gagtgcaccg    1380
gccgctacgg caacgcgtac gaacactccg ggtggaccaa ccgcaacccg cacgcgcacg    1440
ccaacccgga cccgtacgcc cacgcgcacc gcaaccggtc aagtcgcacc aacgaatacc    1500
actgcgccgg cagccaccgc cacgcgcaca ccgacaactg ggaccggtcc taccgccaca    1560
cgcaccaaca ccaccgttgc accaactgcc acgaccggcc cgaccgctgc gcccggcaca    1620
caccagtcaa cgctgaaagt ccagtatcgt tgcgccgata ccaacgcaac tggtaaccag    1680
atcaaaccgc acctgaacat tgtcaacacc ggtagttctg ccgtatcgct caccgctctt    1740
aaagcgcgct actactacac catcgatggc gagaaagcgc aatcgtattg gtgcgactat    1800
gcaacgattg gctgcagcaa tatcaccgcc tcgttcgtga aaatggcgac agcagtaagc    1860
ggcgccgact attacttgga agtgggcttt accagcggta ctctgaatgc aggggctagt    1920
acgggtgaaa tccagaatcg ctttgcgaaa agcgattgga cgaactatac gcagacaggc    1980
gattacagct tcgatcccag caaaaccagc tttgcagact ggaacaaagt aaccctgtac    2040
aacaacggca ccctggtttg gggcgtggaa ccaagtggcg cgagtgctcc ataa           2094
```

The invention claimed is:

1. A thermostable cellobiohydrolase comprising a polypeptide consisting of the amino acid sequence set forth in SEQ ID NO: 1, and a cellulose binding molecule linked to the polypeptide.

2. A cellulase mixture, comprising the thermostable cellobiohydrolase according to claim 1 and at least one other cellulase.

3. The cellulase mixture according to claim 2, wherein said other cellulase is at least one cellulase selected from the group consisting of hemicellulase and endoglucanase.

* * * * *